(12) United States Patent
Hertel et al.

(10) Patent No.: US 6,512,001 B1
(45) Date of Patent: Jan. 28, 2003

(54) D-PROLINE DERIVATIVES

(75) Inventors: Cornelia Hertel, Münchenstein (CH); Torsten Hoffmann, Lörrach (DE); Roland Jakob-Roetne, Inzlingen (DE); Roger David Norcross, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 41 days.

(21) Appl. No.: 09/636,076

(22) Filed: Aug. 10, 2000

Related U.S. Application Data

(62) Division of application No. 09/505,375, filed on Feb. 16, 2000, which is a division of application No. 09/179,652, filed on Oct. 27, 1998.

(30) Foreign Application Priority Data

Oct. 31, 1997 (EP) .............................................. 97119031
Jul. 24, 1998 (EP) .............................................. 98113851

(51) Int. Cl.$^7$ .................. A61K 31/4025; C07D 207/08

(52) U.S. Cl. ....................... 514/422; 514/365; 548/204; 548/523; 548/524

(58) Field of Search ................................ 514/422, 365; 548/524, 204, 523

(56) References Cited

U.S. PATENT DOCUMENTS

| | | |
|---|---|---|
| 4,046,889 A | 9/1977 | Ondetti et al. |
| 4,105,776 A | 8/1978 | Ondetti et al. |
| 4,386,075 A | 5/1983 | Pfeiffer |
| 4,916,146 A | 4/1990 | Tanaka et al. |
| 4,999,417 A | 3/1991 | Domb |
| 5,071,844 A | 12/1991 | Alker et al. |
| 5,439,930 A | 8/1995 | Seredenin et al. |

FOREIGN PATENT DOCUMENTS

| | | |
|---|---|---|
| DE | 2 328 391 | 6/1973 |
| DE | 27 03 828 | 8/1977 |
| GB | 2 205 832 | 12/1988 |
| JP | 49-61136 | 6/1974 |
| JP | 53 108922 | 9/1978 |
| JP | 58-152851 | 9/1983 |
| JP | 58-189158 | 11/1983 |
| JP | 64-16761 | 1/1989 |
| JP | 1 230578 | 9/1989 |
| JP | 1 250370 | 10/1989 |
| JP | 2 157262 | 6/1990 |
| JP | 3 17079 | 1/1991 |
| JP | 7-89933 | 4/1995 |
| JP | 9-157251 | 6/1997 |
| WO | WO 95/14705 | 6/1995 |
| WO | WO 97/10225 | 3/1997 |
| WO | WO 97/21728 | 6/1997 |

OTHER PUBLICATIONS

Greene, "Protective Groups in Organic Synthesis" (1981) pp. 50–72.*
Bundgaard, Drugs of the Future, 16 (5):443–458 (1991).
Saab et al., Journal of Pharmaceutical Sciences, 79 (9):802–805 (Sep. 1990).
Lambert et al., Current Medicinal Chemistry, 1:376–391 (1995).
Saunders et al., Journal of Computer–Aided Molecular Design, 1:133–142 (1987).
Derwent Abstract No. 95–206892/199527 (Abstract of WO 95/14705) (1995).
Sutter et al., Helvetica Chimica Acta, 54 (7):2097–2107 (1971).
Patent Abstract of Japan vol. 096, No. 006, Publication No. 08040896 (1996).
Patent Abstract of Japan vol. 018, No. 290, Publication No. 06061099 (1994).
Tetrahedon Letters, 38(17) (1982) pp. 2725–2727 Columbo et al.
Tetrahedron Letters, 30(32) (1989) pp. 4227–4230, Waldmann et al.
New J. Chem. 15 (1991) pp. 379–384 LeMaire.
Chem. Pharm. Bull 43(12) (1995) pp. 2048–2053, Yoshikawa et al.
J. Med. Chem. 37 (1994) pp. 3677–3683 Baurer et al.
Tetrahedron Letters 31(9) (1990) pp. 1241–1244 Kronenthal et al.

(List continued on next page.)

Primary Examiner—Ceila Chang
Assistant Examiner—Sonya Wright
(74) Attorney, Agent, or Firm—George W. Johnston; John P. Parise

(57) ABSTRACT

New compounds have the formula:

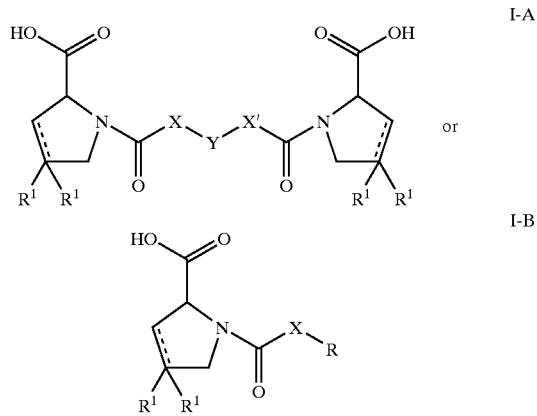

wherein R, $R^1$, X and Y have the meanings described herein. Methods are set forth for synthesizing these compounds and using these compounds to treat diseases associated with amyloidosis, such as Alzheimer's disease, maturity onset diabetes mellitus, familial amyloid polyneuropathy, scrapie, and Kreuzfeld-Jacob disease.

11 Claims, No Drawings

OTHER PUBLICATIONS

J. Pharm. Sot. Korea 31(1) (1987) pp. 1–9 Hoeji.
J. Med. Chem. 36 (1993) pp. 314–319, Shuman et al.
The Merck Index, Abstr. 1817 (1996).
J. Med. Chem. 31 (1988) pp. 875–885, Smith et al.

* cited by examiner

D-PROLINE DERIVATIVES

CROSS REFERENCE TO RELATED APPLICATIONS

This is a divisional of copending application(s) Ser. No. 09/505,375 filed Feb. 16, 2000 which is a divisional of Ser. No. 09/179,652 filed on Oct. 27, 1998.

BACKGROUND OF THE INVENTION

1. Field

The invention relates to D-prolines and their use in treating diseases associated with amyloidosis.

2. Description

The compounds (R)-1-[(R)-3-mercapto-2-methyl-propionyl]-pyrrolidine-2-carboxylic acid and (R)-1-[(S)-3-mercapto-2-methyl-propionyl]-pyrrolidine-2-carboxylic acid are disclosed in WO 97/10225 as having antibacterial activity against B. fragilis. These compounds are also disclosed in J. Comput. Aided Mol. Des., 1(2): 133–42 (1987) in a theoretical study of angiotensin-converting enzyme inhibitors. However, the use of these compounds for treating or preventing central and systemic amyloidosis was not known before the subject invention.

The subject invention provides unique D-proline derivatives that can be used to treat or prevent central and systemic amyloidosis. Amyloidosis is a disorder of protein metabolism in which normally soluble autologous proteins are deposited in tissues as abnormal insoluble fibrils that can cause structural and functional disruption. Disorders associated with amylodosis include Alzheimer's disease and maturity onset diabetes mellitus.

SUMMARY OF THE INVENTION

The invention relates to D-prolines of the formula:

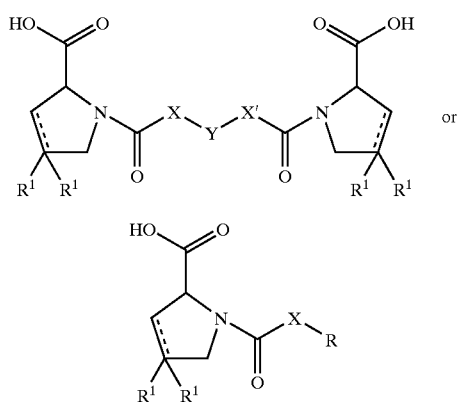

wherein
R is SH; benzyl; benzyl substituted by hydroxy or lower alkoxy; phenyl; phenyl substituted by hydroxy or lower alkoxy; or

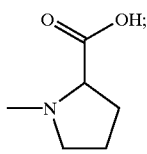

the group
$R^1$ is hydrogen or halogen;
X is $-(CH_2)_n-$; $-CH(R^2)(CH_2)_n-$; $-CH_2O(CH_2)_n-$; $-CH_2NH-$; benzyl; $-C(R^2)=CH-$; $-CH_2CH(OH)-$; or thiazol-2,5-diyl;
Y is $-S-S-$; $-(CH_2)_n-$; $-O-$; $-NH-$; $-N(R^2)-$; $-CH=CH-$; $-NHC(O)NH-$; $-N(R^2)C(O)N(R^2)-$; $-N[CH_2C_6H_3(OCH_3)_2]-$; $-N(CH_2C_5H_5)-$; $-N(CH_2C_6H_5)C(O)N(CH_2C_6H_5)-$; $-N(alkoxyalkyl)-$; $-N(cycloalkyl-methyl)-$; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenyl; 1,2-phenylen; 1,3-phenylen; 1,4-phenylen; 1,2-phenylen substituted by 1 to 4 substituents selected from the group consisting of halogen, lower alkyl, lower alkoxy, hydroxy, carboxy, $-COO$-lower alkyl, nitrilo, 5-tetrazol, (2-carboxylic acid-pyrrolidin-1-yl)-2-oxo-ethoxy, N-hydroxycarbamimidoyl, 5-oxo-[1,2,4]oxadiazolyl, 2-oxo-[1,2,3,5]oxathiadiazolyl, 5-thioxo-[1,2,4]oxadiazolyl, and 5-tert-butylsulfanyl-[1,2,4]oxadiazolyl; 1,3-phenylen substituted by 1 to 4 substituents selected from the group consisting of halogen, lower alkyl, lower alkoxy, hydroxy, carboxy, $-COO$-lower alkyl, nitrilo, 5-tetrazol, (2-carboxylic acid-pyrrolidin-1-yl)-2-oxo-ethoxy, N-hydroxycarbamimidoyl, 5-oxo-[1,2,4]oxadiazolyl, 2-oxo-[1,2,3,5]oxathiadiazolyl, 5-thioxo-[1,2,4]oxadiazolyl, and 5-tert-butylsulfanyl-[1,2,4]oxadiazolyl; and 1,4-phenylen substituted by 1 to 4 substituents selected from the group consisting of halogen, lower alkyl, lower alkoxy, hydroxy, carboxy, $-COO$-lower alkyl, nitrilo, 5-tetrazol, (2-carboxylic acid-pyrrolidin-1-yl)-2-oxo-ethoxy, N-hydroxycarbamimidoyl, 5-oxo-[1,2,4]oxadiazolyl, 2-oxo-[1,2,3,5]oxathiadiazolyl, 5-thioxo-[1,2,4]oxadiazolyl, and 5-tert-butylsulfanyl-[1,2,4]oxadiazolyl;
X' is $-(CH_2)_n-$; $-(CH_2)_nCH(R^2)-$; $-(CH_2)_nOCH_2-$; $-NHCH_2-$; benzyl; $-CH=C(R^2)-$; $-CH(OH)CH_2$; or thiazol-2,5-diyl;
$R^2$ is lower alkyl, lower alkoxy, or benzyl;
=== is a single or a double bond; and
n is 0–3,
and to pharmaceutically acceptable salts and mono- and diesters thereof, with the exception of (R)-1-[(R)-3-mercapto-2-methyl-propionyl]pyrrolidine-2-carboxylic acid and (R)-1-[(S)-3-mercapto-2-methyl-propionyl]pyrrolidine-2-carboxylic acid.

A method of using these compounds for treating diseases associated with amyloidosis by administering to a subject in need of such treatment an effective amount of one of the above-identified compounds or (R)-1-[(R)-3-mercapto-2-methyl-propionyl]pyrrolidine-2-carboxylic acid or (R)-1-[(S)-3-mercapto-2-methyl-propionyl]pyrrolidine-2-carboxylic acid is also provided.

DETAILED DESCRIPTION OF THE INVENTION

The invention will now be described in terms of its preferred embodiments. These embodiments are set forth to aid in understanding the invention but are not to be construed as limiting.

The invention provides compounds of the formulas:

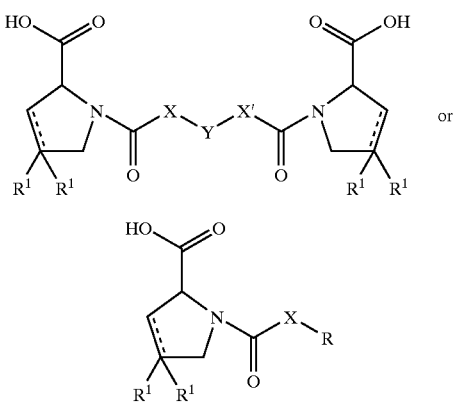

wherein
R is SH, benzyl or phenyl, optionally substituted by hydroxy or lower alkoxy or

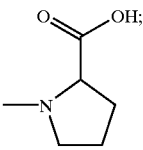

the group
$R^1$ is hydrogen or halogen;
X is $-(CH_2)_n-$; $-CH(R^2)(CH_2)_n-$; $-CH_2O(CH_2)_n-$; $-CH_2NH-$; benzyl, $-C(R^2)=CH-$; $-CH_2CH(OH)-$; or thiazol-2,5-diyl;
Y is $-S-S-$; $-(CH_2)_n-$; $-O-$; $-NH-$; $-N(R^2)-$; $-CH=CH-$; $-NHC(O)NH-$; $-N(R^2)C(O)N(R^2)-$; $-N[CH_2C_6H_3(OCH_3)_2]-$; $-N(CH_2C_6H_5)-$; $-N(CH_2C_6H_5)C(O)N(CH_2C_6H_5)-$; $-N(alkoxyalkyl)-$; $-N(cycloalkylmethyl)-$; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenyl; or 1,2-phenylen, 1,3-phenylen and 1,4-phenylen, wherein the phenylen groups are optionally substituted by 1–4 substituents, selected from halogen, lower alkyl, lower alkoxy, hydroxy, carboxy, $-COO-$lower alkyl, nitrilo, 5-tetrazol, (2-carboxylic acid-pyrrolidin-1-yl)-2-oxo-ethoxy, N-hydroxycarbamimidoyl, 5-oxo-[1,2,4]oxadiazolyl, 2-oxo-[1,2,3,5]oxathiadiazolyl, 5-thioxo-[1,2,4]oxadiazolyl and 5-tert-butylsulfanyl-[1,2,4]oxadiazolyl;
X' is $-(CH_2)_n-$; $-(CH_2)_nCH(R^2)-$; $-(CH_2)_nOCH_2-$; $-NHCH_2-$; benzyl, $-CH=C(R^2)-$; $-CH(OH)CH_2-$; or thiazol-2,5-diyl;
$R^2$ is lower alkyl, lower alkoxy or benzyl and
n is 0–3,
and pharmaceutically acceptable salts or mono- and diesters thereof, with the exception of (R)-1-[(R)- and (R)-1-[(S)-3-mercapto-2-methyl-propionyl]-pyrrolidine-2-carboxylic acid.

The compounds of formulas I-A or I-B may contain 4 or 2 asymmetric carbon atoms. Accordingly, the present invention includes all sterioisomeric forms of the compounds of formula I-A or I-B, including each of the individual enantiomers and mixtures thereof.

It has been surprisingly found that the D-prolines of formula I-A and I-B can be used in the treatment or prevention of all forms of central and systemic amyloidosis, which is a disorder of protein metabolism in which normally soluble autologous proteins are deposited in the tissues as abnormal insoluble fibrils, which cause structural and functional disruption. The most common disorders associated with amyloidosis are Alzheimer's disease (AD), maturity onset diabetes mellitus, or amyloidosis
as a significant cause of non-ischaemic heart failure,
as complication of long term haemodialysis in renal failure,
as complication of monoclonal gammopathies,
from chronic inflammatory disorders,
from chronic infections or
from certain types of cancer.

Furthermore, amyloidosis comprises many different diseases such as forms of hereditary amyloidosis most common familial amyloid polyneuropathy (FAP), scrapie and Kreuzfeld-Jakob disease.

The common pathological feature is extracellular deposition so called amyloid proteins in B-structured fibers and the same staining characteristics. Serum amyloid P component (SAP) is a normal plasma protein and the precursor of amyloid component, a universal constituent of the abnormal tissue deposits in amyloidosis. It is resistant to proteases and therefore plays a key role in the persistance of amyloid in vivo. For therapy pharmaceutically active compounds have to be found which would prevent the interaction of SAP with amyloid fibrils. This interaction has been demonstrated to be a protein fiber interaction, rather than an interaction with more general fiber components such as glycosaminoglycans. SAP consists as a pentamer of 5 identical non-covalently associated subunits. Two pentamers can non-covalently associate to a decamer with the two pentameric disk-like rings interacting face to face. SAP is a calcium-dependent ligand binding protein. It is produced and degraded exclusively in hepatocytes and extremely stabile outside the liver.

The participation of SAP in the pathogenesis of amyloidosis in vivo confirms that inhibition of binding to amyloid fibrils is an attractive therapeutic target in a range of serious human diseases.

Objects of the present invention are the aforementioned compounds of formula I-A and I-B and salts and esters thereof per se and as therapeutically active substances, their manufacture and their use for therapeutic purposes and, respectively, for the production of corresponding medicaments as well as medicaments containing a compound of formula I-A and I-B or a salt thereof and the production of such medicaments for said purpose.

The term "lower alkyl" denotes straight-chain or branched-chain saturated hydrocarbon residues, preferably with 1–4 C atoms, such as methyl, ethyl, propyl, isopropyl, n-butyl, 2-butyl, isobutyl and t-butyl.

"Halogen" denotes chlorine, iodine, fluorine and bromine.

Compounds of formula I-A and I-B can form salts with metals e.g. alkali metal salts such as sodium or potassium salts or alkaline earth metal salts such as calcium or magnesium salts, with organic bases, e.g. salts with amines such as N-ethylpiperidine, procaine or dibenzylamine, or salts with basic amino acids such as salts with arginine or lysine. These salts can be formed and isolated by methods well known in the art.

The compounds can also be used in the ester form, such esters being aliphatic or aromatic, such as, for example alkyl and phenolic esters. The most preferred esters are alkyl esters derived from $C_{1-4}$ alkanols, especially methyl and ethyl esters. The compounds of formulas I-A and I-B can also be used in form of their prodrugs at either one or both carbonyl functions. Examples are esters, intramolecular esters, phosphate esters, double esters, glycolamide esters, glyceride conjugates, dihydropyridine derivatives or 8-(hydroxymethyl)-1-naphthylmethyidisulfide esters. The prodrugs may add to the value of the present compounds advantages in absorption, pharmacokinetics in distribution and transport to the brain. (WO 9514705; H. Bundgaard et al., *Drugs of the Future*, 16: 443 (1991); A. N. Saab et al., *Pharmaceutical Science*, 79:802 (1990); D. M. Lambert et al., *Current Medical Chemistry*, 1:376 (1995).

Preferred are compounds of formula I-A. Especially preferred compounds of formula I-A in the scope of the present invention are those in which X is $CH(R^2)(CH_2)_n$— and wherein $R^2$ is methyl or methoxy and, n is 0 or 1.

The following are examples of such compounds:
- (R)-1-[(S)-3-[(S)-3-[(R)-2-Carboxy-pyrrolidin-1-yl]-2-methyl-3-oxopropyldisulfanyl]-2-methyl-propionyl]-pyrrolidine-2-carboxylic acid,
- (R)-1-[8-[(R)-2-Carboxy-pyrrolidin-1-yl)-2,7-dimethyl-8-oxo-octanoyl]-pyrrolidine-2-carboxylic acid,
- (R)-1-[8-[(R)-2-Carboxy-pyrrolidin-1-yl]-2,7-dimethoxy-8-oxo-octanoyl]-pyrrolidine-2-carboxylic acid and
- (R)-1-[6-[(R)-2-Carboxy-pyrrolidin-1-yl)-2,5-dimethyl-6-oxo-hexanoyl]-pyrrolidine-2-carboxylic acid (mixture of 3 diastereomers) Especially preferred are also compounds, in which X is —$(CH_2)_n$— and n is 0 or 1.

Such compounds are:
- (R)-1-[7-[(R)-2-Carboxy-pyrrolidin-1-yl]-7-oxo-heptanoyl]-pyrrolidine-2-carboxylic acid,
- (R)-1-[6-[(R)-2-Carboxy-pyrrolidin-1-yl]-6-oxo-hexanoyl]-pyrrolidine-2-carboxylic acid,
- (R)-1-[5-[(R)-2-Carboxy-pyrrolidin-1-yl]-5-oxo-pentanoyl]-pyrrolidine-2-carboxylic acid,
- (R)-1-[[4-[2-[(R)-2-Carboxy-pyrrolidin-1-yl]-2-oxo-ethyl]-phenyl]acetyl]-pyrrolidine-2-carboxylic acid,
- (R)-1-[[3-[2-[(R)-2-Carboxy-pyrrolidin-1-yl]-2-oxo-ethoxy]-ureido]-pyrrolidine-2-carboxylic acid,
- (R)-1-[[Benzyl-[2-[(R)-2-carboxy-pyrrolidin-1-yl]-2-oxo-ethyl]-amino]-acetyl]-pyrrolidine-2-carboxylic acid,
- (R)-1-[cis-4-[(R)-2-Carboxy-pyrrolidine-1-carbonyl]-cyclohexanecarbonyl]-pyrrolidine-2-carboxylic acid and
- (R)-1-[[3-[2-[(R)-2-Carboxy-pyrrolidin-1-yl]-2-oxo-ethyl]-phenyl]-acetyl]-pyrrolidine-2-carboxylic acid.

Preferred are further compounds of formula I-A, wherein X is —$CH_2O$—.

Examples of such compounds are the following:
- (R)-1-[[2-[2-[(R)-2-Carboxy-pyrrolidin-1-yl]-2-oxo-ethoxy]-phenoxy]-acetyl]-pyrrolidine-2-carboxylic acid,
- (R)-1-[[4-[2-[(R)-2-Carboxy-pyrrolidin-1-yl]-2-oxo-ethoxy]-phenoxy]-acetyl]-pyrrolidine-2-carboxylic acid,
- (R)-1-[[4-[2-[(R)-2-Carboxy-pyrrolidin-1-yl]-2-oxo-ethoxy]-2-methoxy-phenoxy]-acetyl]-pyrrolidine-2-carboxylic acid,
- (R)-1-[[3-[2-[(R)-2-Carboxy-pyrrolidin-1-yl]-2-oxo-ethoxy]-phenoxy]-acetyl]-pyrrolidine-2-carboxylic acid,
- (R)-1-[[3-[2-[(R)-2-Carboxy-pyrrolidin-1-yl]-2-oxo-ethoxy]-2-methyl-phenoxy]-acetyl]-pyrrolidine-2-carboxylic acid and
- (R)-1-[[5-[2-[(R)-2-Carboxy-pyrrolidin-1-yl]-2-oxo-ethoxy]-naphthalen-1-yloxy]-acetyl]-pyrrolidine-2-carboxylic acid.

Compounds in which X is —$CH_2NH$ are further preferred.

An example of such a compound is
- (R)-1-[[4-[2-[(R)-2-Carboxy-pyrrolidin-1-yl]-2-oxo-ethylamino]-phenylamino]-acetyl]-pyrrolidine-2-carboxylic acid.

Compounds, in which X is —$CH_2CH(OH)$— are further preferred.

Such a compound is, for example,
- (2E,4E)-(R)-1-[6-[(R)-2-Carboxy-pyrrolidin-1-yl]-2,5-dimethyl-6-oxo-hexa-2,4-dienoyl]-pyrrolidine-2-carboxylic acid.

The aforementioned compounds of formula I-A and I-B can be manufactured in accordance with the invention by a) converting a compound of formula

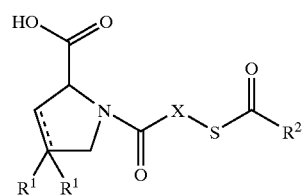

II into a compound of formula

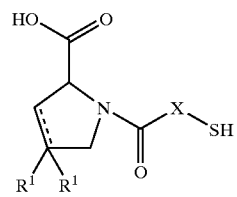

I-B-1 and then into a compound of formula

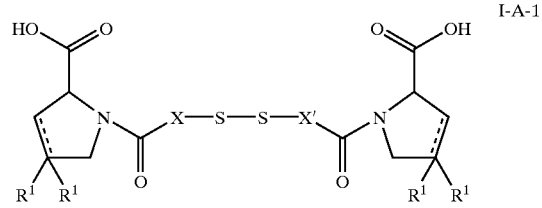

I-A-1 wherein $R^1$, X and X' have the significances given above and $R^2$ is lower alkyl, or b) treating a compound of formula

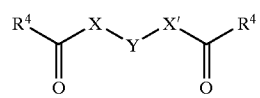

VIII with a compound of formula

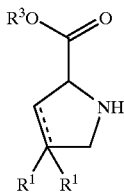

V to a compound of formula I-A by cleaving off the protecting group, wherein X, Y and X' have the significances given above and $R^4$ is hydroxy or halogen, or c) reacting a compound of formula

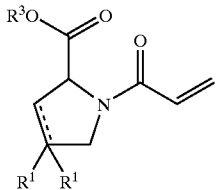

IX with an amine of formula $NH_2R^5$ and cleaving off the protecting group from a compound of formula

XI

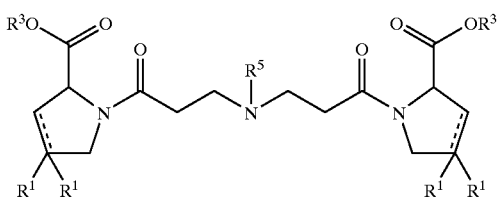

wherein $R^1$ and $R^3$ and described as above and $R^5$ is hydrogen, lower alkyl, lower alkoxy, benzyl, lower alkoxyalkyl, cycloalkyl-methyl or

—$CH_2C_6H_3(OCH_3)_2$, or d) reacting a compound of formula

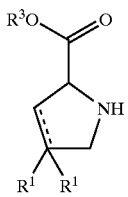

V with a compound of formula

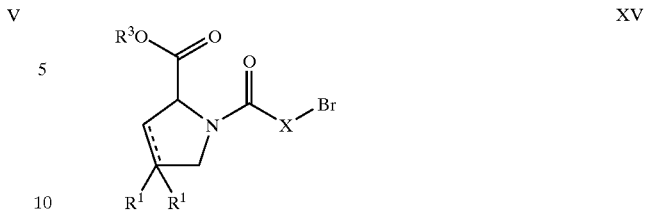

XV and cleaving off the protecting group of a compound of formula

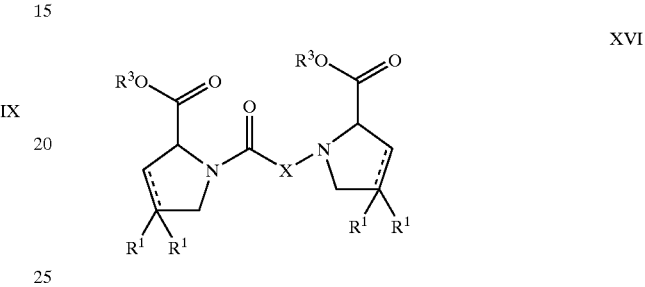

XVI wherein $R^1$, $R^3$ and X have the significances given above, or e) reacting a compound of formula

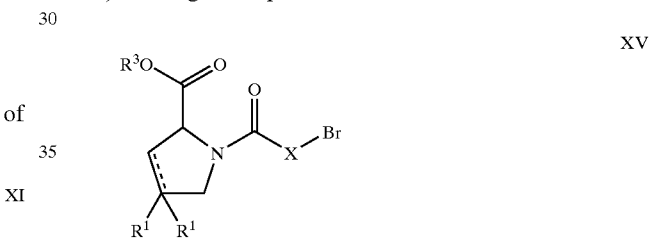

XV with a compound of formula

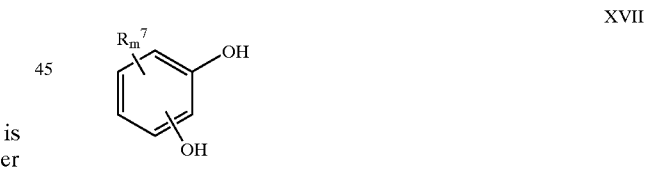

XVII and cleaving off the protecting group of compounds of formula

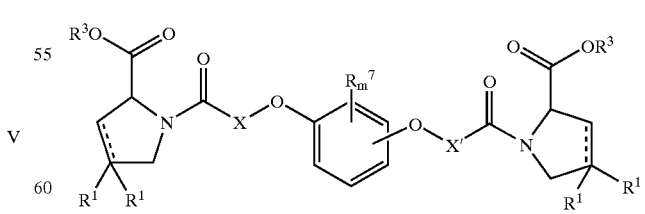

V wherein $R^1$, $R^3$ and X have the significances given above and $R^7$ is halogen, lower alkyl, lower alkoxy, hydroxy, carboxy, —COO-lower alkyl, nitrilo, 5-tetrazol, (2-carboxylic acid-pyrrolidin-1-yl)-2-oxo-ethoxy, N-hydroxycarbamimidoyl, 5-oxo-[1,2,4]oxadiazolyl, 2-oxo-[1,2,3,5]oxathiadiazolyl, 5-thioxo-[1,2,4]oxadiazolyl and 5-tert-butylsulfanyl-[1,2,4]oxadiazolyl, and m is 0–4, or f) cleaving off a protecting group from a compound of formulas

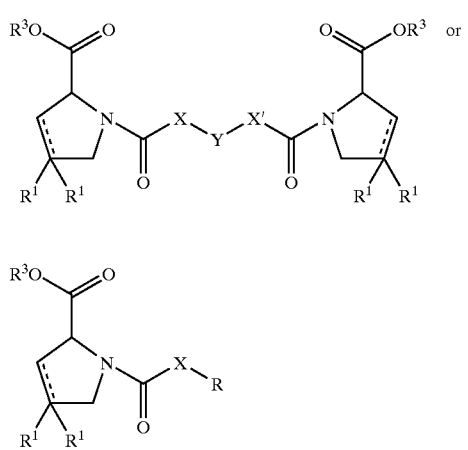

wherein R, $R^1$, X, Y and X' is as described as above and R is a protecting group,
to give a compound of formula I-A or I-B, and, if desired, converting a compound of formulas I-A and I-B into a pharmaceutically usable salt or into a mono- and diester.

In accordance with process variant (a) a compound of formula I-A-1 is obtained by converting a compound of formula II, for example 1-[(S)-3-acetyl-sulfanyl-2-methyl-propionyl]-(R)-pyrrolidine-2-carboxylic acid, into a compound of formula I-B-1 and then into a compound of formula I-A-1. The reaction is conveniently effected under inert atmosphere at room temperature in the presence of ammonia in a solvent, such as methanol. After stirring for about 2 hours the compound is separated and subsequently the reaction product can be worked-up to the desired pure product according to generally known methods.

The compounds of formula I-A-1 are obtained by stirring the above compound in a solution of $CuSO_4$ in water at room temperature.

The precise reaction conditions are described in more detail in the working Examples.

In accordance with reaction step (b) a protected D-proline is treated with a corresponding dicarboxylic acid or with a corresponding acetyl halide at 0° C. The following dicarboxylic acids are preferred: 2,4-dimethylglutaric acid, 2,3-dimethylsuccimic acid, cyclohexane-1,4-dicarboxylic acid, cyclohexane-1,3-dicarboxylic acid, cyclohexane-1,2-dicarboxylic acid, 1,4-phenylenediacetic acid, 1,3-phenylenediacetic acid, benzene-1,4-dioic acid, benzene-1,3-dioic acid, pyridine-2,6-dicarboxylic acid, thiophene-2,5-dicarboxylic acid, furan-2,5-dicarboxylic acid, adipic acid, 1,4-phenylenediacetic acid, 1,2-phenylenediacetic acid, (4-carboxymethyl-naphthylen-1-yl)acetic acid, (6)-carboxymethyl-pyridel-2-yl)acetic acid, (5-carboxymethyl-thiophen-2-yl acetic acid, 2,5-dimethoxy-hexanedioic acid, 2,5-dibenzyl-hex-3-enedioic acid or 2,5-diisopropyl-hex-3-enedioxic acid. A detailed procedure is described in the Examples in the General Procedure A.

The reaction step (c) describes the treatment of an amine, for example propylamine, cyclopropylmethylamine, methoxyethylamine, benzylamine or veratrylamine with a compound of formula IX. This reaction is carried out at a temperature between 20 and 80° C. in a solvent, such as acetonitrile.

In accordance with variant (d) a compound of formula I-B is prepared. To a compound of formula XV in dichloromethane at 0° C. is added a corresponding bromacetyl derivative, such as bromacetyl bromide, and a compound of formula V. The deprotection is than carried out by methods known in the art.

Compounds, in which Y is an optionally substituted 1,2-, 1,3- or 1,4-phenylen group, can be prepared in accordance with reaction variant (e). To a compound of formula XV a corresponding dihydroxy-derivative of formula XVII is added. The reaction is carried out in dimethylformamide at room temperature. Preferred are the following dihydroxy-derivatives: hydroquinone, tetrafluorohydroquinone, chorohydroquinone, methoxyhydroquinone, resorcinol, 2,6-dihydroxytoluene, 5-methoxyresorcinol, 3,5-dihydroxybenzoate, 3,5-dihydroxybenzonitrile, phloroglucinol, pyrogallol-1-methyl ether, 3-methylcatechol, tetrachlorocatechol, 2,6-dihydroxynaphthalene, 1,5-dihydroxynaphthalene, 2,3-dihydroxynaphthalene, 2,2'-dihydroxybiphenyl, 1,4-naphthoquinone or 2,7-dihydroxynaphthalene.

In accordance with process variant (f), a compound of formulas III or IV is deprotected to a compound of formula I-A or I-B. Suitable protecting groups and methods for their cleavage will be familiar to any person skilled in the art, although of course there can be used only those protecting groups which can be cleaved off by methods under the conditions of which other structural elements are not affected. The tert-butyl group and the benzyl group are preferred O-protecting groups. The process is carried out in conventional manner. For example, a compound of formula III can be dissolved in a suitable solvent or mixture of solvents such as ethanol and ethylacetate, and hydrogenated in the presence of Pd on carbon at room temperature and atmospheric pressure.

Pharmaceutically acceptable salts and esters can be manufactured according to methods which are known per se and familiar to any person skilled in the art.

In schemes 1–9 are described processes for preparation of compounds of formulas I-A and I-B, starting from known compounds or from compounds, which can be prepared in conventional manner.

The starting materials of formulas V, VI, VIII, IX, X, XII, XIV, XVII, XX and XXIV are commercial products or can be prepared according to methods known per se.

The preparation of compounds of formulas I-A and I-B are described in more detail in working Examples 1–104.

Scheme 1
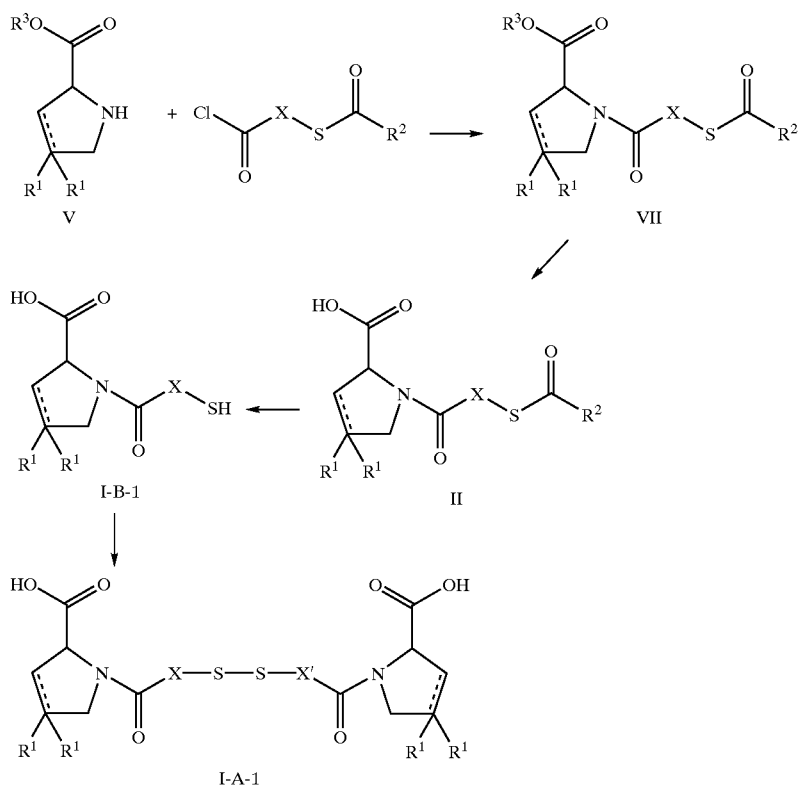
wherein $R^1$, X and X' have the significances given above, $R^2$ is lower alkyl and $R^3$ is a protecting group.
Scheme 2
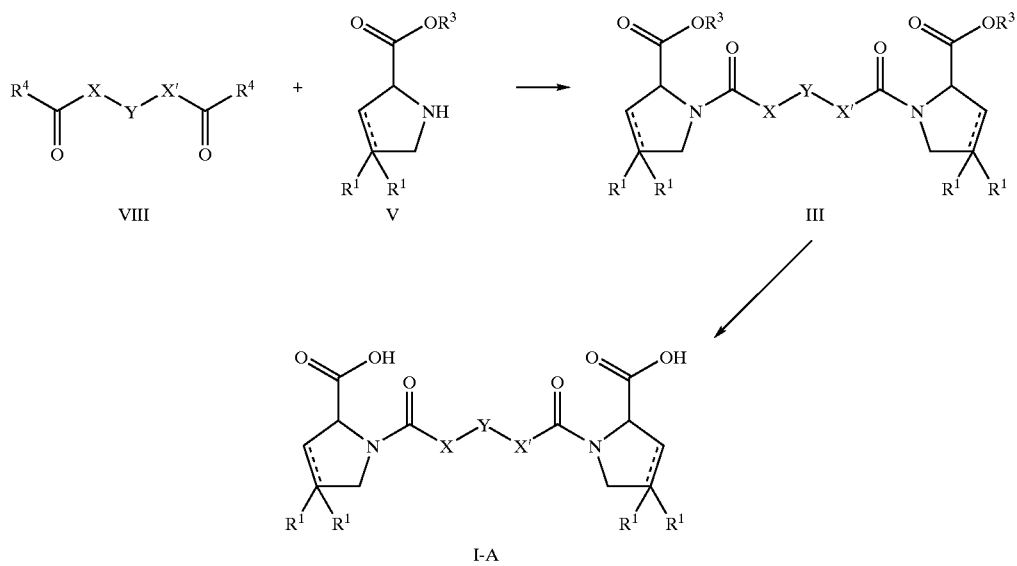

wherein X, Y and X' have the significances given above and R⁴ is hydroxy or halogen.
Scheme 3
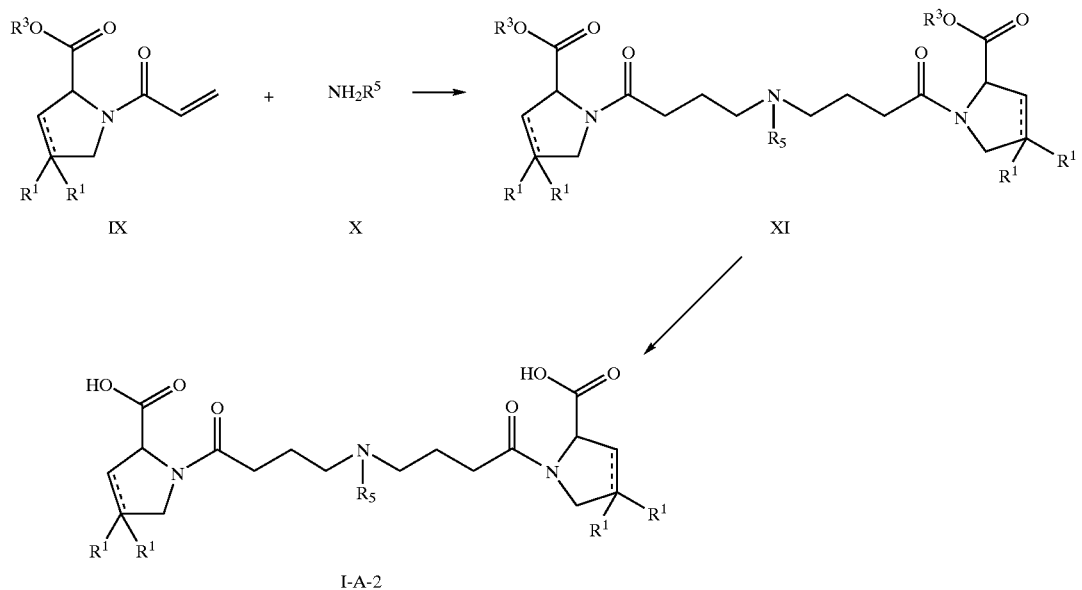
wherein $R^1$ and $R^3$ are described as above and $R^4$ is hydrogen, lower alkyl, lower alkoxy, benzyl, lower alkoxyalkyl, cycloalkyl-methyl or —CH₂C₆H₃(OCH₃)₂.
Scheme 4
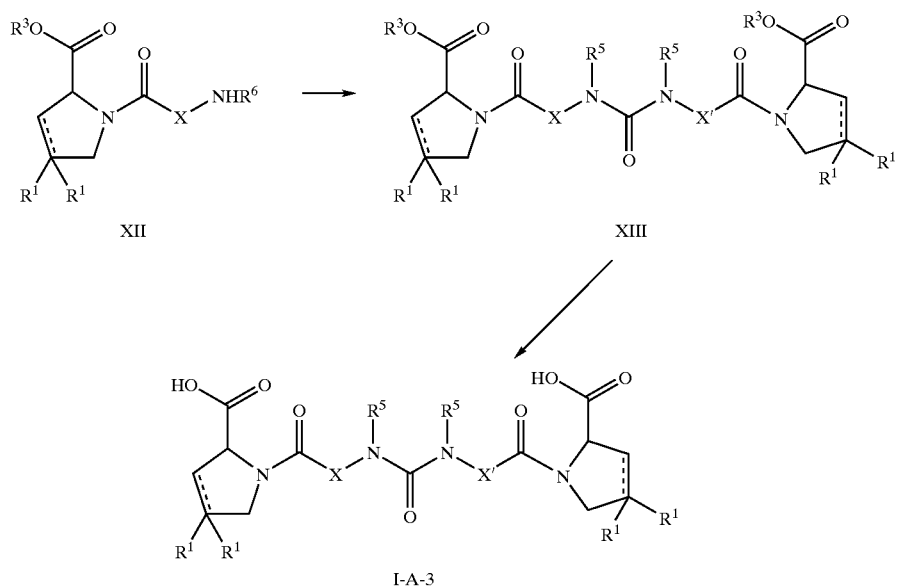

wherein $R^1$, $R^3$, X and X' have the significances given above and $R^6$ is hydrogen, lower alkyl, lower alkoxy, or benzyl.

Scheme 5

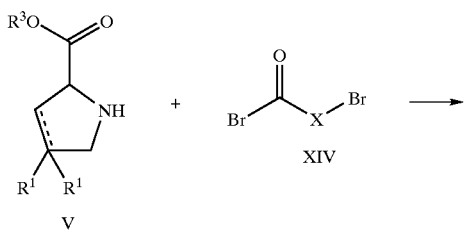

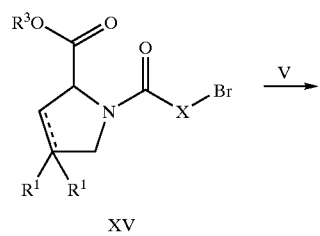

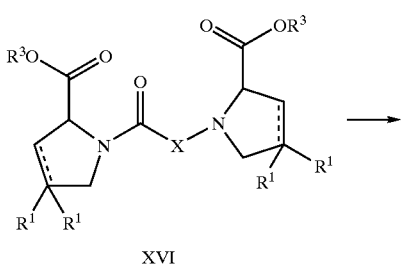

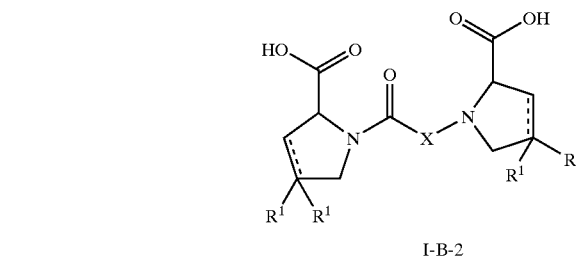

wherein $R^1$, $R^3$ and X have the significances given above.

Scheme 6

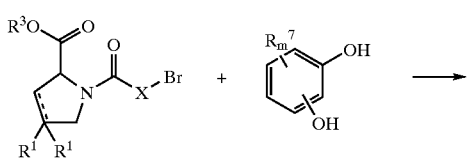

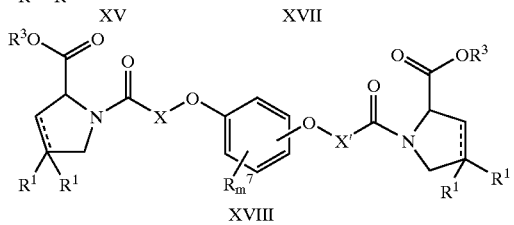

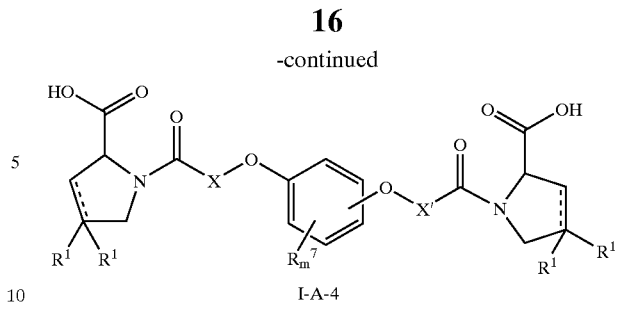

wherein $R^1$, $R^3$ and X have the significances given above and $R^7$ is halogen, lower alkyl, lower alkoxy, hydroxy, carboxy, —COO-lower alkyl, nitrilo, 5-tetrazol, (2-carboxylic acid-pyrrolidin-1-yl)-2-oxo-ethoxy, N-hydroxycarbamimidoyl, 5-oxo-[1,2,4]oxadiazolyl, 2-oxo-[1,2,3,5]oxathiadiazolyl, 5-thioxo-[1,2,4]oxadiazolyl and 5-tert-butylsulfanyl-[1,2,4]oxadiazolyl, and m is 0–4.

Scheme 7

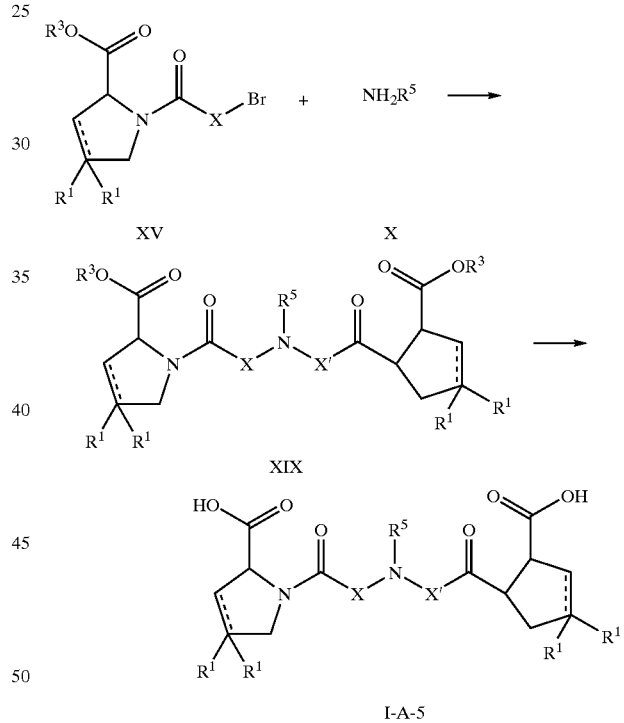

wherein $R^1$, $R^3$, $R^5$, X and X' have the significances given above.

Scheme 8

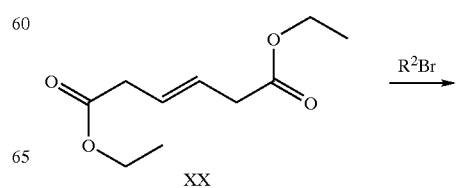

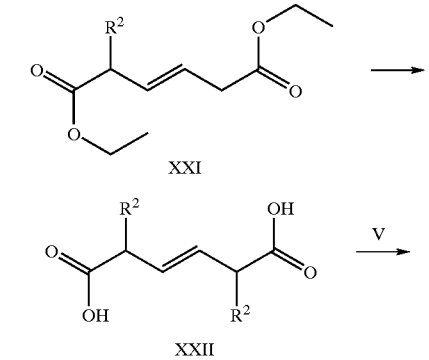
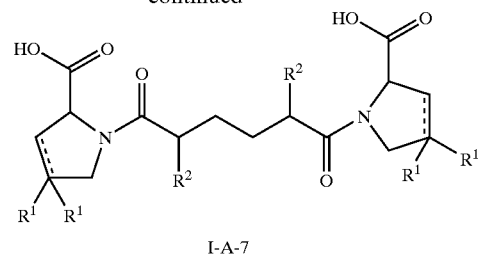
wherein $R^1$ and $R^2$ have the significances given above.
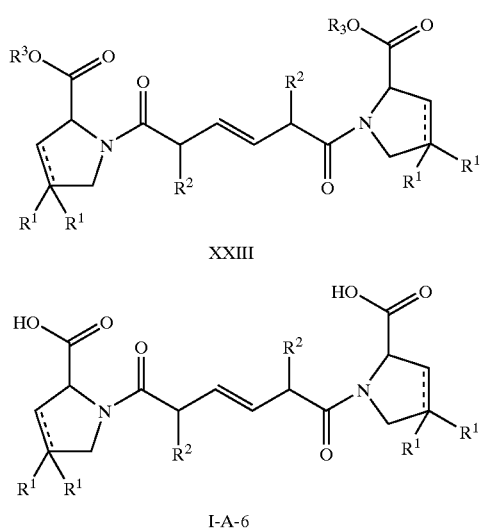
Scheme 9
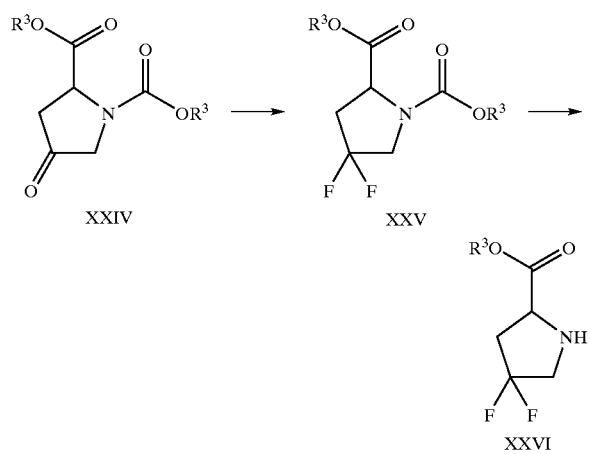
wherein $R^3$ has the significance given above.
The preparation of the following examples is described in more detail:
| | I-A | | | I-B | | |
|---|---|---|---|---|---|---|
| X | Y | X' | R | R¹ | Expl. | |
| —CH—CH₂— | —S—S— | —CH₂—CH— | — | H | 1d | |
| —CH—CH₂— | — | — | SH | H | 1c | |
| —CH—CH₂— | —S—S— | —CH₂—CH— | — | H | 2c | |
| —CH—CH₂— | — | — | SH | H | 2b | |
| —(CH₂)₂— | —S—S— | —(CH₂)₂— | — | H | 3 | |

-continued
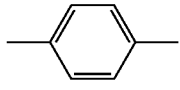
| X | Y | X' | R | R¹ | Expl. |
|---|---|---|---|---|---|
| —(CH₂)₃— | —CH₂— | —(CH₂)₃— | — | H | 4b |
| —CH(CH₃)CH₂— | —(CH₂)₂— | —CH₂CH(CH₃)— | — | H | 5 |
| CH(OCH₃)CH₂ | —(CH₂)₂— | —CH₂CH(OCH₃)— | — | H | 6b |
| —(CH₂)₂— | —CH₂— | —(CH₂)₂— | — | H | 7 |
| —CH₂— | —(CH₂)₂— | —CH₂— | — | H | 8b (R),(R) |
| —CH₂— | —CH₂— | —CH₂— | — | H | 9b |
| —CH₂— | a bond | —CH₂— | — | H | 10b |
| —CH₂O(CH₂)₂— | —O— | —(CH₂)₂OCH₂— | — | H | 11 |
| —(CH₂)₂— | 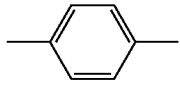 | —(CH₂)₂— | — | H | 12 |
| —CH₂— | 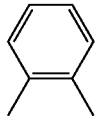 | —CH₂— | — | H | 13 (R),(R) |
| —CH₂O— | 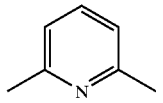 | —OCH₃— | — | H | 14b (R),(R) |
| —(CH₂)₂— | 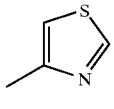 | —(CH₂)₂— | — | H | 15c |
| —(CH₂)₂— | —N[(CH₂)₂CH₃]— | —(CH₂)₂— | — | H | 16c |
| —CH₂— | —NHC(O)NH— | —CH₂— | — | H | 17c |
| —(CH₂)₃— | —(CH₂)₂— | —(CH₂)₃— | — | H | 18 |
| —(CH₂)₂— | —(CH₂)₂— | —(CH₂)₂— | — | H | 19 |
| 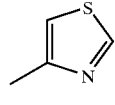 | a bond | 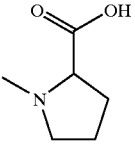 | — | H | 20b |
| —CH₂— | — | — | 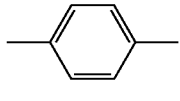 | H | 21d |
| —CH₂O— |  | —OCH₂— | — | H | 22b |

-continued

| | I-A | | | I-B | | |
|---|---|---|---|---|---|---|
| X | Y | X' | R | R¹ | Expl. | |

| X | Y | X' | R | R¹ | Expl. |
|---|---|---|---|---|---|
| —CH₂O— | (tetrafluorophenylene) | —OCH₂— | — | H | 23b |
| —CH₂O— | (chloro-dimethylphenylene) | —OCH₂— | — | H | 24b |
| —CH₂O— | (phenoxy-dimethylphenylene) | —OCH₂— | — | H | 25b |
| —CH₂O— | — | — | Mixt of (methoxyphenyl / methoxy-hydroxyphenyl) | H | 26b |
| —CH₂O— | (m-xylylene) | —OCH₂— | — | H | 27b |
| —CH₂O— | — | — | (m-cresol) | H | 28b |
| —CH₂O— | (methylphenylene) | —OCH₂— | — | H | 29b |

-continued

| | | | I-A | | I-B |

| X | Y | X' | R | R¹ | Expl. |
|---|---|---|---|---|---|
| —CH₂O— | 3,5-dimethylanisole | —OCH₂— | — | H | 30b |
| —CH₂O— | methyl 3,5-dimethylbenzoate | —OCH₂— | — | H | 31b |
| —CH₂O— | 3,5-dimethylbenzoic acid | —OCH₂— | — | H | 32 |
| —CH₂O— | 3,5-dimethylbenzonitrile | —OCH₂— | — | H | 33b |
| —CH₂O— | 5-(3,5-dimethylphenyl)-1H-tetrazole | —OCH₂— | — | H | 34 |
| —CH₂O— | 3,5-dimethylphenol | —OCH₂— | — | H | 35b |

-continued

| | | | I-A | | | I-B |
|---|---|---|---|---|---|---|

Structures I-A and I-B shown with substituents X, Y, X', R, R¹.

| X | Y | X' | R | R¹ | Expl. |
|---|---|---|---|---|---|
| —CH₂O— | pyrrolidine-2-carboxylic acid linked via ethoxy to 3,5-dimethylphenyl | —OCH₂— | — | H | 36b |
| —CH₂O— | N-hydroxybenzamidine on 3,5-dimethylphenyl | —OCH₂— | — | H | 37b |
| —CH₂O— | 1,2,4-oxadiazol-5(4H)-one on 3,5-dimethylphenyl | —OCH₂— | — | H | 38b |
| —CH₂O— | 1,2,3,5-oxathiadiazole on 3,5-dimethylphenyl | —OCH₂— | — | H | 39b |

-continued

| | | | I-A | | | I-B |
|---|---|---|---|---|---|---|
| X | Y | X' | | R | R¹ | Expl. |
| —CH₂O— | 5-(tert-butylthio)-3-(3,5-dimethylphenyl)-1,2,4-oxadiazole | —OCH₂— | | — | H | 40b |
| —CH₂O— | 2,3-dimethylphenylene | —OCH₂— | | — | H | 41b |
| —CH₂O— | 2,3-dimethylphenylene | —OCH₂— | | — | H | 42b |
| —CH₂O— | tetrachloro-dimethylphenylene | —OCH₂— | | — | H | 43b |
| —CH₂O— | 2,6-dimethylnaphthalene-diyl | —OCH₂— | | — | H | 44b |
| —CH₂O— | 1,5-dimethylnaphthalene-diyl | —OCH₂— | | — | H | 45b |
| —CH₂O— | 2,3-dimethylnaphthalene-diyl | —OCH₂— | | — | H | 46b |

-continued
| | I-A | | | I-B | |
|---|---|---|---|---|---|
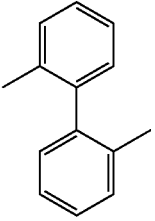
and
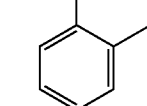
| X | Y | X' | R | R¹ | Expl. |
|---|---|---|---|---|---|
| —CH₂O— | 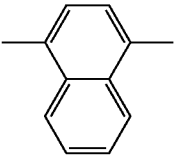 | —OCH₂— | — | H | 47b |
| —CH₂O— | 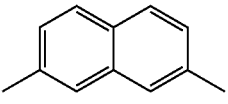 | —OCH₂— | — | H | 48b |
| —CH₂O— | 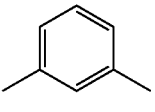 | —OCH₂— | — | H | 49b |
| —CH₂NH— |  | —NHCH₂— | — | H | 50b |
| —CH₂NH— | 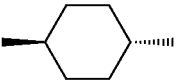 | —NHCH₂— | — | H | 51b |
| —CH₂— | —N[(CH₂)₃CH₃]— | —CH₂— | — | H | 52b |
| —CH₂— | —N[(CH₂)₂OCH₃]— | —CH₂— | — | H | 53b |
| —CH₂— | —N(CH₂C₆H₅)— | —CH₂— | — | H | 54b |
| —CH₂— | —N[(CH₂)₃CH₃]—CO—N[(CH₂)₃CH₃]— | —CH₂— | — | H | 55c |
| —CH₂— | —N[CH₂C₆H₅]—CO—N[CH₂C₆H₅]— | —CH₂— | — | H | 56c |
| —CH₂NH— | — | — | benzyl | H | 57 |
| —CH(CH₃)— | —CH₂— | —CH(CH₃)— | — | H | 58b |
| —CH(CH₃)— | a bond | —CH(CH₃)— | — | H | 59b |
| a bond | 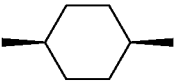 | a bond | — | H | 60b |
| a bond | 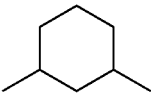 | a bond | — | H | 61b |
| a bond |  | a bond | — | H | 62b |

-continued
I-A
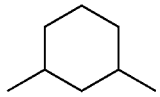
and
I-B
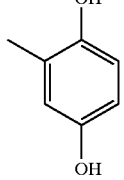
| X | Y | X' | R | R¹ | Expl. |
|---|---|----|---|----|-------|
| a bond | 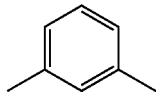 | a bond | — | H | 63b |
| —CH$_2$— | 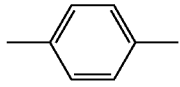 | —CH$_2$— | — | H | 64b |
| —CH$_2$— | 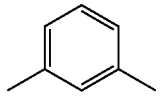 | —CH$_2$— | — | H | 65b |
| a bond | 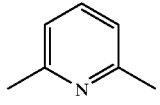 | a bond | — | H | 66b |
| a bond | 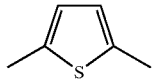 | a bond | — | H | 67b |
| a bond | 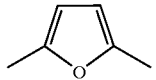 | a bond | — | H | 68b |
| a bond | 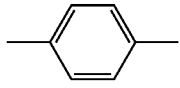 | a bond | — | H | 69b |
| a bond |  | a bond | — | H | 70b |
| —CH$_2$— | —CH$_2$— | —CH$_2$— | — | H | 71b (S),(S) |
| —CH$_2$— |  | —CH$_2$— | — | H | 72b (S),(S) |
| —CH$_2$O— |  | —OCH$_2$— | — | H | 73b (S),(S) |

-continued

| | | | I-A | | | I-B |
|---|---|---|---|---|---|---|

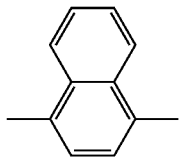 and 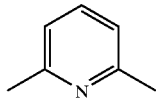

| X | Y | X' | R | R¹ | Expl. |
|---|---|---|---|---|---|
| —CH₂— | 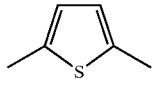 | —CH₂— | — | H | 74d |
| —CH₂— | 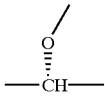 | —CH₂— | — | H | 75d |
| —CH₂— | 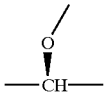 | —CH₂— | — | H | 76e |
| 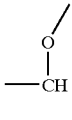 | —(CH₂)₂— | 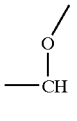 | — | H | 77d |
| 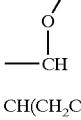 | —(CH₂)₂— | 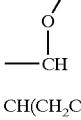 | — | H | 78f |
| 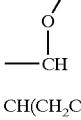 | —(CH₂)₂— | 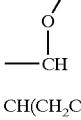 | — | H | 79<br>2 diastereomers |
| CH(CH₂C₆H₅) | —(CH₂)₂— | —CH(CH₂C₆H₅)— | — | H | 80d |
| —CH[(CH₂)₄]— | —(CH₂)₂— | —CH[(CH₂)₄]— | — | H | 81d |
| —CH[(CH₂)₄]— | —(CH₂)₂— | —CH[(CH₂)₄]— | — | H | 82<br>2 diastereomers |
| —CH(i-prop.)- | —(CH₂)₂— | —CH(i-prop.)- | — | H | 83d |
| —CH[(CH₂)₂OCH₃]— | —(CH₂)₂— | —CH[(CH₂)₂OCH₃]— | — | H | 84d |
| —CH(CH₃)— | 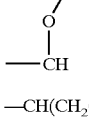 | —CH(CH₃)— | — | H | 85e<br>3 diastereomers |
| —C(CH₃)=CH— | a bond | —CH=C(CH₃)— | — | H | 86b |
| —CH(CH₃)— | —(CH₂)₂— | —CH(CH₃)— | — | H | 87 |
| —CH₂CH(OH)— | a bond | —CH(OH)CH₂— | — | H | 88c |
| —CH₂— | —CH=CH— | —CH₂— | — | H | 89b |
| —(CH₂)₂— | —N[(CH₂)CH₃]— | —(CH₂)₂— | — | H | 90c |
| —(CH₂)₂— | —N(CH₂cyclopropyl)- | —(CH₂)₂— | — | H | 91b |
| —(CH₂)₂— | —N[CH₂C₆H₃(OCH₃)₂]— | —(CH₂)₂— | — | H | 92c |
| —(CH₂)₂— | —N[(CH₂)₂OCH₃]— | —(CH₂)₂— | — | H | 93b |
| —(CH₂)₂— | —N(CH₂C₆H₅)— | —(CH₂)₂— | — | H | 94b |
| —(CH₂)₂— | —NH— | —(CH₂)₂— | — | H | 95c |
| —(CH₂)₂— | —N(CH₂CH₃)— | —(CH₂)₂— | — | H | 96 |
| —(CH₂)₂— | —N[CH₂C₆H₄CF₃]— | —(CH₂)₂— | — | H | 97 |
| —CH₂— | —(CH₂)₂— | —CH₂— | — | H | 98c<br>(R),(S) |
| —CH₂— | —(CH₂)₂— | —CH₂— | — | H | 99c |

-continued

| X | Y | X' | R | R¹ | Expl. |
|---|---|---|---|---|---|
| —CH₂— | —(CH₂)₂— | —CH₂— | — | F | 100e |
| —CH₂O— | (m-phenylene) | —OCH₂— | — | F | 101b |
| —CH₂— | (p-phenylene) | —CH₂— | — | F | 102b |
| —CH₂— | —(CH₂)₂— | —CH₂— | — | H, =bond | 103f |
| —CH₂O— | (m-phenylene) | —OCH₂— | — | H, =bond | 104b |

As mentioned earlier, the compounds of formulas I-A and I-B have valuable pharmacological properties. They can be used against all forms of central and systemic amyloidosis, which is a disorder of protein metabolism in which normally soluble autologous proteins are deposited in the tissues as abnormal insoluble fibrils, which cause structure and functional disruption.

Compounds of formula I-A and I-B have been tested by the following method:

Test Method
Binding of SAP (Serum Amyloid P) to Human Amyloid Aβ(1–42) Fibrils

Nunc Flouro Polysorp 96 well plates were coated with 0.5 μg/well of Aβ1–42, which had been aged for 7 days at 37° C. Plates were dried for 3 days at 37° C., washed with 2×150 μl of TC (10 mM tris, 138 mM NaCl, 6 mM CaCl₂, 0.05% NaN₃ pH 8.0) with 1% bovine serum albumin. Then 50 μl TC containing 8% bovine serum albumin, 25 μl compound in TC and 25 μl 40 nM [$^{125}$I]serum amyloid protein in TE (10 mM EGTA instead of Ca) were added per well. Incubation was performed over night at room temperature and wells were washed twice with 180 μl of TC containing 1% bovine serum albumin. To determine radioactivity 100 μl Microscint 40 were added per well and radioactivity was measured in a TopCount (Packard).

The IC$_{50}$ (μM) of preferred compounds of formula I-A and I-B are in the range of about 0.2 2.0.

The compounds of formulas I-A and I-B and their pharmaceutically acceptable acid addition salts, their mono-and diesters and cyclic imides thereof can be used as medicaments (e.g. in the form of pharmaceutical preparations). Pharmaceutical preparations can be administered orally (e.g. in the form of tablets, coated tablets, dragées, hard and soft gelatine capsules, solutions, emulsions or suspensions). Administration can, however, also be effected rectally (e.g. in the form of suppositories), parenterally (e.g. in the form of injection solutions), or nasally.

For the manufacture of pharmaceutical preparations, the compounds of formulas I-A and I-B and the pharmaceutically acceptable acid addition salts and esters thereof can be processed with pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oil, waxes, fats, semi-solid and liquid polyols and the like. Depending on the nature of the active substance no carriers are, however, usually required in the case of soft gelatine capsules. Suitable carriers for the manufacture of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

Medicaments containing a compound of formulas I-A or I-B or a pharmaceutically acceptable acid addition salt or mono-and diesters thereof and a therapeutically inert barrier are also an object of the present invention, as is a process for their manufacture which comprises bringing one or more compounds of formulas I-A and I-B and/or pharmaceutically acceptable acid addition salts and mono-and diesters thereof into a galenical administration form together with one or more therapeutically inert carriers.

In accordance with the invention, compounds of formulas I-A and I-B as well as their pharmaceutically acceptable acid addition salts and mono-and diesters thereof can be used used in the treatment or prevention of central and systemic amyloidosis.

The most common disorders associated with amyloidosis are Alzheimer's disease (AD), maturity onset diabetes mellitus, or amyloidosis as a significant cause of non-ischaemic heart failure, as complication of long term haemodialysis in renal failure, as complication of monoclonal gammopathies, from chronic inflammatory disorders, from chronic infections and from certain types of cancer.

Furthermore, amyloidosis comprises many different diseases such as forms of hereditary amyloidosis, most commonly familial amyloid polyneuropathy (FAP), scrapie and Kreuzfeld-Jakob disease.

Furthermore, the present compounds can be used for the manufacture of corresponding medicaments. The dosage can vary within wide limits and will, of course, be fitted to the individual requirements in each particular case. In the case of oral administration the dosage lies in a range of about 0.1 mg per dosage to about 5,000 mg per day of a compound of formulas I-A or I-B or the corresponding amount of a pharmaceutically acceptable acid addition salt or mono- and diesters thereof. The upper limit can, of course, be exceeded when indicated to be appropriate.

The following Examples illustrate the present invention in more detail. However, they are not intended to limit its scope in any manner. All emperatures are given in degrees Celsius.

EXAMPLE 1

(R)-1-[(S)-3-[(S)-3-[(R)-2-Carboxy-pyrrolidin-1-yl]-2-methyl-3-oxopropyl-disulfanyl]-2-methyl-propionyl]-pyrrolidine-2-carboxylic Acid a) 1-[(S)-3-(Acetylsulfanyl)-20-methyl-propionyl]-(R)-pyrrolidine-2-carboxylic Acid tert-Butylester and 1-[(R)-3-(Acetylsulfanyl)-20-methyl-propionyl]-(R)-pyrrolidine-2-carboxylic Acid tert-Butylester 18.6 ml Triethylamine were given at 0–5° C. to a solution of 23.2 g (135 mmol) D-proline-tert-butylester in 230 ml dry dichloromethane. A solution of 24.5 g (135 mmol) S-(3-chloro-2-methyl-3-oxopropyl)ethanethioic acid ester in 116 ml dichloromethane were added at this temperature over a period of 1 hour and stirring was continued at room temperature for 2 hours. The precipitate was removed by filtration. The solution was washed with water and dried with sodium sulfate. Evaporation of the solvent at reduced pressure gave 41.4 g colorless oil which was chromatographed on 4 kg silicagel with ether/cylohexane 2/1 yielding 19.6 g (46%) 1-[(R)-3-(acetylsulfanyl)-20-methyl-propionyl]-(R)-pyrrolidine-2-carboxylic acid tert-butylester and 18.2 g (43%) 1-[(S)-3-(Acetylsulfanyl)-20-methyl-propionyl]-(R)-pyrrolidine-2-carboxylic acid tert-butylester and 1.6 g mixture of epimers.

MS m/e(%)=315 (M$^+$, 3), 259(10), 242(10), 214(100), 172(10), 145(32), 70(22); [a]$_D$=0.7° (1% EtOH).

MS m/e(%)=315 (M$^+$, 4), 259(7), 242(9), 214(100), 172 (9), 145(33), 70(33); [a]$_D$=+156.7° (1% EtOH).

b) 1-[(S)3-Acetylsulfanyl-2-methyl-propionyl]-(R)-pyrrolidine-2-carboxylic Acid 15.45 g (48.9 mmol) 1-[(S)-3-(Acetylsulfanyl)-20-methyl-propionyl]-(R)-pyrrolidine-2-carboxylic acid tert-butylester were stirred with 99 ml trifluoric acid and 55 ml anisole under argon for three hours. The mixture was evaporated under vacuum. The residue was dissolved in about 100 ml ice cold ethylacetate and washed with about 200 ml of an icecold aqueous solution of sodiumbicarbonate. Concentrated hydrochloric acid was added unter icecooling until ph 1–2. The aqueous phase was extracted four times with icecold ethylacetate, dried with sodium sulfate and evaporated. The yield was 11.6 g (91%) 1-[(S)3-acetylsulfanyl-2-methyl-propionyl]-(R)-pyrrolidine-2-carboxylic acid that was used without further purification. [a]$_D$=−11.8° (0.6% EtOH).

c)1-[(S)3-Mercapto-2-methyl-propionyl]-(R)-pyrrolidine-2-carboxylic Acid 11.59 g (44.69 mmol) 1-[(S)3-acetylsulfanyl-2-methyl-propionyl]-(R)-pyrrolidine-2-carboxylic acid were dissolved at room temperature under argon in 70 ml argon washed methanol. After addition of 70 ml 10N ammonia in methanol stirring was continued for two hours at room temperature. Then the solvent was distilled off under vacuum. The residue was taken up with 5% aqueous KHSO$_4$ solution and extracted six times with with dichloromethane. The organic layers were washed twice with 5% aqueous KHSO$_4$ solution, three times with 1 N hydrochloric acid and dried over sodiumsulfate. Evaporation of the solvent and crystallization from ethylacetate/hexane yielded 6.25 (64%) 1-[(S)3-mercapto-2-methyl-propionyl]-(R)-pyrrolidine-2-carboxylic acid with melting point 99–101°C. a]$_D$=+40.7 (1% EtOH).

d) 1-[(S)3-Mercapto-2-methyl-propionyl]-(R)-pyrrolidine-2-carboxylic Acid

A solution of 749 mg (3.0 mmol) CuSO$_4$×5 $_2$O in 90 ml water was added at room temperature to a solution of 651.85 mg (3.0 mmol)1-[(S)3-mercapto-2-methyl-propionyl]-(R)-pyrrolidine-2-carboxylic acid in 90 ml dichloromethane. The mixture was vigorously stirred for 10 minutes and filtered. The aqueous phase was washed 5 times with dichloromethane, the organic phases were washed with brine and dried with magnesiumsulfate and the solvent was removed under vacuum. Crystallization from dichloromethane/hexane gave 275.3 mg (43%) (R)-1-[(S)-3-[(S)-3-[(R)-2-carboxy-pyrrolidin-1-yl]-2-methyl-3-oxopropyl-disulfanyl]-2-methyl-propionyl]-pyrrolidine-2-carboxylic acid with melting point 142–144° C.

[a]$_D$=+42.8° (1% CHCl$_3$).

EXAMPLE 2

(R)-1-[(R)-3-[(R)-3-[(R)-2-Carboxy-pyrrolidin-1-yl]-2-methyl-3-oxo-propyidisulfanyl)-2-methyl-propionyl]-pyrrolidine-2-carboxylic Acid a) 1-[(R)3-Acetylsulfanyl-2-methyl-propionyl]-(R)-pyrrolidine-2-carboxylic Acid 18.9 g (60.0 mmol)1-(3-acetylsulfanyl-2-methyl-propionyl)-pyrrolidine-2-carboxylic acid tert-butyl ester were stirred with 120 ml trifluoric acid and 75 ml anisole under argon for three hours. The mixture was evaporated under vacuum. The residue was dissolved in icecold ethylacetate and washed with an icecold aqueous solution of sodiumbicarbonate. Concentrated hydrochloric acid was added unter icecooling until ph 2–3. The aqueous phase was extracted three times with icecold ethylacetate, dried with sodium sulfate and evaporated. The yield was 15.3 g (98%) 1-[(R)3-acetylsulfanyl-2-methylpropionyl]-(R)-pyrrolidine-2-carboxylic acid that was used without further purification.

[a]$_D$=+127.8° (1% EtOH).

b) 1-[(R)3-Mercapto-2-methyl-propionyl]-(R)-pyrrolidine-2-carboxylic Acid 2.98 g (11.5 mmol) 1-[(R)3-Acetylsulfanyl-2-methyl-propionyl]-(R)-pyrrolidine-2-carboxylic were dissolved at room temperature under argon in 15 ml argon washed methanol. After addition of 15 ml 10 N ammonia in methanol stirring was continued for two hours at room temperature. Then the solvent was distilled off under vacuum at room temperature. The residue was taken up with 5% aqueous $KHSO_4$ solution and extracted six times with with dichloromethane and three times with ethylacetate. The organic layers were washed twice with 5% aqueous $KHSO_4$ solution, three times with 1 N hydrochloric acid and dried over sodiumsulfate. Evaporation of the solvent and crystallization from ethylacetate/hexane yielded 1.59 g (64%) 1-[(R)3-mercapto-2-methyl-propionyl]-(R)-pyrrolidine-2-carboxylic acid with melting point 98–100° C.

$[a]_D$=+128.8° (1% EtOH).

(R)-1-[(R)-3-[(R)-3-[(R)-2-Carboxy-pyrrolidin-1-yl]-2-methyl-3-oxopropyldisulfanyl]-2-methyl-propionyl]-pyrrolidine-2-carboxylic Acid Analogous to example 1d):
MS m/s (%): 432($M^+$,2) 217(100), 184(76), 172(67), 142 (13), 70(79), 41(21).

EXAMPLE 3

(R)-1-[3-[3-[(R)-2-Carboxy-pyrrolidin-1-yl]-3-oxo-propyl-disulfanyl]-propionyl]-pyrrolidine-2-carboxylic Acid 0.9 g (4 mmol) 1-(3-mercapto-propionyl)-(R)-pyrrolidine-2-carboxylic acid (raw material) were dissolved in dichloromethane and extracted with 50 ml of an saturated aqueous solution of $CuSO_4$. The aqueous phase was extracted twice with dichloromethane, the combined organic phases filtered, dried with magnesiumsulfate and evaporated. Chromatography with dichloromethane/acetone/formic acid 80/20/1 gave 70 mg (R)-1-[3-[3-[(R)-2-carboxy-pyrrolidin-1-yl]-3-oxo-propyl-disulfanyl]-propionyl]-pyrrolidine-acid as a colorless oil.

ISN-MS: 403 (M–H)$^-$.

EXAMPLE 4

(R)-1-[9-[(R)-2-Carboxy-pyrrolidin-1-yl]-9-oxo-nonanoyl]-pyrrolidine-2-carboxylic Acid a) (R)-1-[9-[(R)-2-Benzyloxycarbonyl-pyrrolidin-1-yl]-9-oxo-nonanoyl]-pyrrolidine-2-carboxylic Acid Benzyl Ester 0.97 g (4 mmol) D-proline-benzylester hydrochloride in 25 ml dichloromethane were stirred with 450 mg (2 mmol) azelaoyl chloride and 1.12 ml (8 mmol) triethylamine for 20 hours under argon at room temperature. Extraction with 2N hydrochloric acid and brine, drying with sodiumsulfate and evaporation gave 1.2 g oil which was chromatographed over silicagel with acetoacetate to yield 0.9 g (80%) (R)-1-[9-[(R)-2-benzyloxycarbonyl-pyrrolidin-1-yl]-9-oxo-nonanoyl]-pyrrolidine-2-carboxylic acid benzyl ester as colorless oil.

$^1$H-NMR ($CDCl_3$, ppm): 1.1–2.4 (m, 22H), 3.4–3.7 (m,4H), 4.4–4.6 (m, 2H), 5.1–5.3 (2xAB, 4H), 7.34 (m, 10H).

b) (R)-1-[9-[(R)-2-Carboxy-pyrrolidin-1-yl]-9-oxo-nonanoyl]-pyrrolidine-2-carboxylic Acid, 100 mg (0.18 mmol) (R)-1-[9-[(R)-2-benzyloxycarbonyl-pyrrolidin-1-yl]-9-oxo-nonanoyl]-pyrrolidine-2-carboxylic acid benzyl ester in 20 ml ethanol were hydrogenated in the presence of 20 mg 5% Pd on carbon for two hours at room temperature. Filtration and evaporation gave 60 mg (R)-1-[9-[(R)-2-carboxy-pyrrolidin-1-yl]-9-oxo-nonanoyl]-pyrrolidine-2-carboxylic acid, as a colorless oil.

ISP-MS: 383 (MH$^+$).

EXAMPLE 5

(R)-1-[8-[(R)-2-Carboxy-pyrrolidin-1-yl)-2,7-dimethyl-8-oxo-octanoyl]-pyrrolidine-2-carboxylic Acid 1.2 g (5,0 mmol) 2,7-dimethyl-octanedioylic chloride were dissolved in 100 ml dimethylformamid, 1.15 g (10 mmol) D-proline and 1.4 ml (10 mmol) triethylamine were added and the mixture warmed to 50° C. for five minutes. Stirring was continued at room temperature over night. The solvent was distilled off and the residue taken up in 30 ml 2N hydrochloric acid. Extraction with ethylacetate, drying with sodiumsulfate, evaporation and chromatography over silicagel with chloroform/acetone/formic acid 80/15/5 gave 0.11 g (R)-1-[8-[(R)-2-carboxy-pyrrolidin-1-yl)-2,7-dimethyl-8-oxo-octanoyl]-pyrrolidine-2-carboxylic acid as colorless oil.

ISP-MS: 397 (MH)$^+$.

EXAMPLE 6

(R)-1-[8-[(R)-2-Carboxy-pyrrolidin-1-yl]-2,7-dimethoxy-8-oxo-octanoyl]-pyrrolidine-2-carboxylic Acid a) (R)-1-[8-[(R)-2-Benzyloxycarbonyl-pyrrolidin-1-yl]-2,7-dimethoxy-8-oxoctanoyl]-pyrrolidine-2-carboxylic Acid Benzyl Ester To 0.25 g (1.1 mmol) 2,7-dimethoxy-octanedioic acid in a mixture of 25 ml tetrahydrofuran and 20 ml dichloromethane was added a solution of 0.35 g (2.1 mmol) carbonyldiimidazole in 15 ml tetrahydrofuran. After stirring at room temperature for two hours 0.52 g (2.16 mmol) D-proline-benzylester hydrochloride in 10 ml dichloromethane and 0.54 g triethylamine were added and stirring was continued for 18 hours.

After filtration the solvent was distilled off and the residue dissolved in ethylacetate and extracted with 2N hydrochloric acid and water. Drying with sodiumsulfate, evaporation of the solvent and chromatography over silicagel with ethylacetate yielded 0.21 g (R)-1-[8-[(R)-2-benzyloxycarbonyl-pyrrolidin-1-yl]-2,7-dimethoxy-8-oxo-octanoyl]-pyrrolidine-2-carboxyl acid benzyl ester as a colorless oil.

S-ISP: 609 (M+H)$^+$.

b) (R)-1-[8-[(R)-2-Carboxy-pyrrolidin-1-yl]-2,7-dimethoxy-8-oxo-octanoyl]-pyrrolidine-2-carboxylic Acid 182 mg (0.3 mmol) (R)-1-[8-[(R)-2-benzyloxycarbonyl-pyrrolidin-1-yl]-2,7-dimethoxy-8-oxo-octanoyl]-pyrrolidine-2-carboxylic acid benzyl ester in 10 ml methanol were hydrogenated in the presence of 30 mg 5% Pd on carbon. Filtration and evaporation of the solvent yielded 109 mg (84%) (R)-1-[8-[(R)-2-carboxy-pyrrolidin-1-yl]-2,7-dimethoxy-8-oxo-octanoyl]-pyrrolidine-2-carboxylic acid as colorless oil.

MS: 427 (M–H)$^-$.

EXAMPLE 7

(R)-1-[7-[(R)-2-Carboxy-pyrrolidin-1-yl]-7-oxo-heptanoyl]-pyrrolidine-2-carboxylic Acid A mixture of 0.99 g (5 mmol) pimeloyl chloride, 1.15 g (10 mmol) D-proline and 1.4 ml (10 mmol) triethylamine in 100 ml dimethylformamide was warmed until a clear solution was obtained and then stirred overnight at ambient temperature. The solvent was distilled off under vacuum. The residue was taken up with 2N hydrochloric acid and extracted with dichloromethane. Evaporation of the solvent and chromatography over silicagel with chloroform/aceton/formic acid 80/15/5 yielded 0.27 g (R)-1-[7-[(R)-2-carboxy-pyrrolidin-1-yl]-7-oxo-heptanoyl]-pyrrolidine-2-carboxylic acid as an oil.

MS: 353 (M−H)$^-$.

EXAMPLE 8

(R)-1-[6-[(R)-2-Carboxy-pyrrolidin-1-yl]-6-oxo-hexanoyl]-pyrrolidine-2-carboxylic Acid a) (R)-1-[6-[(R)-2-Benzyloxycarbonyl-pyrrolidin-1-yl]-6-oxo-hexanoyl]-pyrrolidine-2-carboxylic Acid Benzyl Ester 0.97 g (10 mmol) D-proline-benzylester hydrochloride in 70 ml dichloromethane were stirred with 0.92 g (5 mmol) adipoyl chloride and 2.8 ml (20 mmol) triethylamine over the weekend under argon at room temperature. Extraction with 2N hydrochloric acid and water, drying with sodiumsulfate, evaporation and chromatography over silicagel with acetoacetate to yielded 0.42 g (16%) (R)-1-[6-[(R)-2-benzyloxycarbonyl-pyrrolidin-1-yl]-6-oxo-hexanoyl]-pyrrolidine-2-carboxylic acid benzyl ester as colorless oil.

MS-ISP: 521 (M+H)$^+$.

b) (R)-1-[6-[(R)-2-Carboxy-pyrrolidin-1-yl]-6-oxo-hexanoyl]-pyrrolidine-2-carboxylic Acid 410 mg (0.79 mmol) (R)-1-[6-[(R)-2-benzyloxycarbonyl-pyrrolidin-1-yl]-6-oxo-hexanoyl]-pyrrolidine-2-carboxylic acid benzyl ester in 100 ml methanol were hydrogenated in theosence of 50 mg 5% Pd on carbonotration and evaporation of the solvent yielded 160 mg (59%) (R)-1-[6-[(R)-2-carboxy-pyrrolidin-1-yl]-6-oxo-hexanoyl]-pyrrolidine-2-carboxylic acid as colorless oil.

MS: 339 (M−H)$^-$.

EXAMPLE 9

(R)-1-[5-[(R)-2-Carboxy-pyrrolidin-1-yl]-5-oxo-pentanoyl]-pyrrolidine-2-carboxylic Acid a) (R)-1-[5-[(R)-2-Benzyloxycarbonyl-pyrrolidin-1-yl]-5-oxo-pentanoyl]-pyrrolidine-2-carboxylic Acid Benzyl Ester 0.97 g (10 mmol) D-proline-benzylester hydrochloride in 70 ml dichloromethane were stirred with 0.85 g (5 mmol) glutaryl dichloride and 2.8 ml (20 mmol) triethylamine over night under argon at room temperature. Extraction with 2N hydrochloric acid and brine, drying with sodiumsulfate, evaporation and chromatography over silicagel with acetoacetate to yielded 0.44 g (17%) (R)-1-[5-[(R)-2-benzyloxycarbonyl-pyrrolidin-1-yl]-5-oxopentanoyl]-pyrrolidine-2-carboxylic acid benzyl ester as colorless oil.

MS-ISP: 507 (M+H)$^+$.

b) (R)-1-[5-[(R)-2-Carboxy-pyrrolidin-1-yl]-5-oxo-pentanoyl]-pyrrolidine-2-carboxylic Acid 440 mg (0.87 mmol) (R)-1-[5-[(R)-2-benzyloxycarbonyl-pyrrolidin-1-yl]-5-oxo-pentanoyl]-pyrrolidine-2-carboxylic acid benzyl ester in 100 ml ethanol were hydrogenated in the presence of 40 mg 5% Pd on carbon. Filtration and evaporation of the solvent yielded 130 mg (46%) (R)-1-[5-[(R)-2-carboxy-pyrrolidin-1-yl]-5-oxo-pentanoyl]-pyrrolidine-2-carboxylic acid as colorless oil.

MS-ISP: 327 (M+H)$^+$.

EXAMPLE 10

(R)-1-[4-[(R)-2-Carboxy-pyrrolidin-1-yl]-4-oxo-butyryl]-pyrrolidine-2-carboxylic Acid a) (R)-1-[4-[(R)-2-Benzyloxycarbonyl-pyrrolidin-1-yl]-4-oxo-butyryl]-pyrrolidine-2-carboxylic Acid Benzyl Ester To a solution of 300 mg (1.2 mmol) D-Proline benzyl ester hydrochloride and 0.35 ml (2.5 mmol) triethylamine in 9 ml dichloromethane at 0° C. was added dropwise 68 ml (0.6 mmol) succinyl chloride and stirring continued for 24 h at room temperature. The reaction mixture was then washed sequentially with saturated ammonium chloride solution, saturated sodium bicarbonate solution and finally with water, and the aqueous phases back-extracted with dichloromethane. The combined organic extracts were dried over sodium sulphate and concentrated in vacuo to afford 286 mg (94%) of the title compound as a pale yellow oil.

MS m/e (%): 510 (M+NH4$^+$, 20), 493 (M+H$^+$, 100), 288 (80).

b) (R)-1-[4-[(R)-2-Carboxy-pyrrolidin-1-yl]-4-oxo-butyryl]-pyrrolidine-2-carboxylic Acid A solution of 256 mg (0.5 mmol) (R)-1-[4-[(R)-2-benzyloxycarbonyl-pyrrolidin-1-yl]-4-oxo-butyryl]-pyrrolidine-2-carboxylic acid benzyl ester in 5 ml ethanol was stirred with 13 mg 10% Palladium on carbon under 1 atm of hydrogen for 16 h at room temperature. After filtration to remove the catalyst, concentration in vacuo afforded 170 mg (100%) of the title compound KR)-1[4-[(R)-2-carboxy-pyrrolidin-1-yl]-4-oxo-butyryl]-pyrrolidine-2-carboxylic acid as a colorless viscous oil.

MS m/e (%): 313 (M+H)$^+$, 100).

EXAMPLE 11

(R)-1-[[2-[2-[2-[(R)-2-Carboxy-pyrrolidin-1-yl)-2-oxo-ethoxy]ethoxy]-ethoxy]acetyl]-pyrrolidine-2-carboxylic Acid A mixture of 1.04 g (4 mmol) 2,2'-[oxybis(2,1-ethanediyloxy)]bis acetyl chloride, 0.92 g (8 mmol) D-proline and 1.2 ml triethylamine in 200 ml dimethylformamide was stirred for three days at ambient temperature. The solvent was distilled off under vacuum. The residue was chromatographed over silicagel with methanol to yield 0.42 g (R)-1-[[2-[2-[2-[(R)-2-carboxy-pyrrolidin-1-yl)-2-oxo-ethoxy]ethoxy]-ethoxy]-acetyl]-pyrrolidine-2-carboxylic acid as a beige hygroscopic solid.

MS-ISP: 417 (M+H)$^+$.

EXAMPLE 12

(R)-1-[3-[4-[3-[(R)-2-Carboxy-pyrrolidin-1-yl)-3-oxo-propyl]-phenyl]-propionyl]-pyrrolidine-2-carboxylic Acid A mixture of 1.30 g (5 mmol) 1,4-benzene dipropanoyl dichloride, 1.15 g (10 mmol) D-proline and 1.5 ml triethylamine in 100 ml dimethylformamide was stirred for 24 hours at ambient temperature. The suspension was filtered and the solvent was distilled off under vacuum. The residue was taken up in acetoacetate, washed with 2N hydrochloric acid, dried over sodiumsulfate and chromatographed over silicagel with dichloromethane/acetone/formic acid 80/5/15 to yield 0.48 g (R)-1-[3-[4-[3-[(R)-2-carboxy-pyrrolidin-1-yl)-3-oxo-propyl]-phenyl]-propionyl]-pyrrolidine-2-carboxylic acid as colorless foam.

MS-ISP: 417 (M+H)$^+$.

EXAMPLE 13

(R)-1-[[4-[2-[(R)-2-Carboxy-pyrrolidin-1-yl]-2-oxo-ethyl]-phenyl]acetyl]-pyrrolidine-2-carboxylic Acid A mixture of 1.15 g (5 mmol) 1,4-benzene diacetyl dichloride, 1.15 g (10 mmol) D-proline and 1.5 ml triethylamine in 100 ml dimethylformamide was stirred for 20 hours at ambient temperature. The solvent was distilled off under vacuum. The residue was taken up in 30 ml 2N hyuohloric acid, treated with ultrasound, filtered and dried to yield 1.19 g of a brown solid. This was stirred and refluxed for 30 minutes in 300 ml methanol. Filtration, evaporation and recrystallization from methanol/acetoacetate gave 0.18 g (R)-1-[[4-[2-[(R)-2-carboxy-pyrrolidin-1-yl]-2-oxo-ethyl]-phenyl]acetyl]-pyrrolidine-2-carboxylic acid as yellow crystals with melting point 210–214° C.

MS-ISP: 389 (M+H)$^+$.

EXAMPLE 14

(R)-1-[[2-[2-[(R)-2-Carboxy-pyrrolidin-1-yl]-2-oxo-ethoxy]-phenoxy]-acetyl]-pyrrolidine-2-carboxylic Acid a) (R)-1-[[2-[2-[(R)-2-Benzyloxycarbonyl-pyrrolidin-1-yl]-2-oxo-ethoxy]phenoxy]acetyl]-pyrrolidine-2-carboxylic Acid Benzyl Ester To 0.566 g (2.5 mmol) 1,2-phenylenedioxyacetic acid in 60 ml tetrahydrofuran was added a solution of 0.81 g (5 mmol) carbonyidiimidazole in 25 ml tetrahydrofuran. After stirring at room temperature for two hours 1.21 g (5 mmol) ) D-proline-benzylester hydrochloride in 30 ml dichloromethane and 1.4 ml triethylamine were added and stirring was continued over the weekend.

The mixture was extracted with 2N hydrochloric acid and brine. Drying with sodiumsulfate, evaporation of the solvent and chromatography over silicagel with ethylaceteate yielded 0.25 g (R)-1-[[2-[2-[(R)-2-benzyloxycarbonyl-pyrrolidin-1-yl]-2-oxo-ethoxy]-phenoxy]acetyl]-pyrrolidine-2-carboxlic acid benzyl ester as colorless oil.

MS m/e (%): 600 (1,M$^+$), 509 (1), 368 (25), 246 (17), 217 (19), 204 (14), 91 (100).

b) (R)-1-[[2-[2-[(R)-2-Carboxy-pyrrolidin-1-yl]-2-oxo-ethoxy]-phenoxy]-acetyl]-pyrrolidine-2-carboxylic Acid 230 mg (0.38 mmol) (R)-1-[[2-[2-[(R)-2-benzyloxycarbonyl-pyrrolidin-1-yl]-2-oxo-ethoxy]-phenoxy]acetyl]-pyrrolidine-2-carboxylic acid benzyl ester in 100 ml ethanol were hydrogenated in the presence of 30 mg 5% Pd on carbon. Filtration and evaporation of the solvent yielded 0.2 g (R)-1-[[2-[2-[(R)-2-carboxy-pyrrolidin-1-yl]-2-oxo-ethoxy]-phenoxy]-acetyl]-pyrrolidine-2-carboxylic acid as colorless glass (that still contained small amounts of ethanol)

MS-ISP: 421 (M+H)$^+$.

EXAMPLE 15

(R)-1-[3-[6-[3-[(R)-2-Carboxy-pyrrolidin-1-yl]-3-oxo-propyl]-pyridin-2-yl]propionyl]-pyrrolidine-2-carboxylic Acid a) 3-[6-(2-Carboxy-ethyl)-pyridin-2-yl]-propionic Acid A mixture of 25.6 g (0.2 mol) naphthalin and 1.39 g (0.2 mol) lithium in 150 ml tetrahydrofurane was stirred for three hours at room temperature. After cooling to −15° C. a solution of 5.72 ml (0.1 mol) acetic acid in 10 ml tetrahydrofurane was added and stirring was continued for three hours at room temperature. Then 13.3 g (0.5 mol) 2,6-bis-(bromomethyl)pyridine in 65 ml tetrahydrofurane was added and stirring was continued over night at room temperature. 200 ml ether were added and the mixture was extracted with water. The water layers were filtered through 200 ml BioRad AG1-X8 ion exchanger. The ion-exchanger was washed with water until neutral and then eluated with acetic acid/water. Product containing fractions were evaporated, dissolved in water and lyophylized to yield 3.9 g (35%) 3-[6-(2-carboxy-ethyl)-pyridin-2-yl]-propionic acid as a light yellow powder.

MS m/e (%): 223 (M$^+$,15), 178(100), 160(81), 132(68), 104(16), 77(13).

b) (R)-1-[3-[6-[3-[(R)-2-Benzyloxycarbonyl-pyrrolidin-1-yl]-3-oxo-propyl]pyridin-2-yl]-propionyl]-pyrrolidine-2-carboxylic Acid Benzyl Ester To 0.45 g (2.0 mmol) 3-[6-(2-carboxy-ethyl)-pyridin-2-yl]-propionic acid in a mixture of 25 ml tetrahydrofuran and 25 ml dichloromethane was added a solution of 0.65 g (4.0 mmol) carbonyldiimidazole in 20 ml tetrahydrofuran. After stirring at room temperature for two hours 0.97 g (4.0 mmol) D-proline-benzylester hydrochloride in 50 ml dichloromethane and 1.12 g triethylamine were added and stirring was continued for 18 hours.

Then ethylacetate was added to the mixture followed by extraction with water. Drying with sodiumsulfate, evaporation of the solvent and chromatography over silicagel with ethylaceteate/hexane 2/8, then ethylacetate, then ethylacetate/methanol 95/5 followed by a second chromatography of the product containing fractions on silicagel with aceton/hexane 6/4 yielded 0.18 g (15%) (R)-1-[3-[6-[3-[(R)-2-benzyloxycarbonyl-pyrrolidin-1-yl]-3-oxo-propyl]-pyridin-2-yl]-propionyl]-pyrrolidine-2-carboxylic acid benzyl ester as a colorless oil.

MS-ISP: 598 (M+H)$^+$.

c) (R)-1-[3-[6-[3-[(R)-2-Carboxy-pyrrolidin-1-yl]-3-oxo-propyl]-pyridin-2-yl]propionyl]-pyrrolidine-2-carboxylic Acid 0.17 g (0.29 mmol) (R)-1-[3-[6-[3-[(R)-2-benzyloxycarbonyl-pyrrolidin-1-yl]-3-oxo-propyl]-pyridin-2-yl]-propionyl]-pyrrolidine-2-carboxylic acid benzyl ester in 100 ml ethanol were hydrogenated in the presence of 35 mg 5% Pd on carbon. Filtration and evaporation of the solvent yielded 0.11 g (92%) (R)-1-[3-[6-[3-[(R)-2-carboxy-pyrrolidin-1-yl]-3-oxo-propyl]-pyridin-2-yl]propionyl]-pyrrolidine-2-carboxylic acid as colorless oil.

MS-ISP: 418 (M+H)$^+$.

EXAMPLE 16

(R)-1-[3-[[3-[(R)-2-Carboxy-pyrrolidin-1-yl]-3-oxo-propyl]-propyl-amino]-propionyl]-pyrrolidine-2-carboxylic Acid a) (R)-1-Acryloyl-pyrrolidine-2-carboxylic Acid Benzyl Ester To a solution of 390 mg (1.6 mmol) D-Proline benzyl ester hydrochloride and 0.47 ml (3.4 mmol) triethylamine in 20 ml dichloromethane at 0° C. was added dropwise 0.2 ml (2.4 mmol) acryloyl chloride and stirring continued for 24 h at room temperature. The reaction mixture was then washed sequentially with water, 1 M hydrochloric acid and once more with water, and the aqueous phases back-extracted with dichloromethane. The combined organic extracts were dried over sodium sulphate and concentrated in vacuo to afford 420 mg (100%) of the title compound (R)-1-acryloyl-pyrrolidine-2-carboxylic acid benzyl ester as a colorless oil.

MS m/e (%): 259 (M$^+$, 25), 124 (100), 91 (25), 70 (21).

b) (R)-1-[3-[[3-[(R)-2-Benzyloxycarbonyl-pyrrolidin-1-yl]-3-oxo-propyl]-propylamino]-propionyl]-pyrrolidine-2-carboxylic Acid Benzyl Ester A solution of 400 mg (1.5 mmol) (R)-1-acryloyl-pyrrolidine-2-carboxylic acid benzyl ester and 63 ml (0.75 mmol) propylamine in 5 ml acetonitrile was stirred for 16 h at room temperature, then for 6 h at 45° C., and finally for 16 h at 80° C. Concentration in vacuo and flash chromatography (20% H$_2$O in acetone) afforded 84 mg (19%) of the title compound (R)-1-[3-[[3-[(R)-2-benzyloxycarbonylpyrrolidin-1-yl]-3-oxo-propyl]-propyl-amino]-propionyl]-pyrrolidine-2-carboxylic acid benzyl ester as a pale yellow oil.

MS m/e (%): 578 (M+H⁺, 100).

c) (R)-1-[3-[[3-[(R)-2-Carboxy-pyrrolidin-1-yl]-3-oxo-propyl]-propyl-amino]-propionyl]-pyrrolidine-2-carboxylic Acid A solution of 84 mg (0.15 mmol) (R)-1-[3-[[3-[(R)-2-benzyloxycarbonyl-pyrrolidin-1-yl]-3-oxo-propyl]-propyl-amino]-propionyl]-pyrrolidine-2-carboxylic acid benzyl ester in 3 ml ethanol was stirred with 10 mg 10% palladium on carbon under 1 atm of hydrogen for 16 h at room temperature. After filtration to remove the catalyst, concentration in vacuo afforded 58 mg (100%) of the title compound (R)-1-[3-[[3-[(R)-2-carboxy-pyrrolidin-1-yl]-3-oxo-propyl]-propylamino]-propionyl]-pyrrolidine-2-carboxylic acid as a white solid.

MS m/e (%): 398 (M+H⁺, 100).

EXAMPLE 17

(R)-1-[[3-[2-[(R)-2-Carboxy-pyrrolidin-1-yl]-2-oxo-ethoxy]-ureido]-pyrrolidine-2-carboxylic Acid a) (R)-1-tert-Butoxycarbonylaminoacetyl-pyrrolidine-2-carboxylic Acid Benzyl Ester 1.21 g (5 mmol) D-proline-benzylester hydrochloride were dissolved in 100 ml dichloromethane and strirred with 0.7 ml triethylamine. The mixture was extracted with water, dried with sodiumsulfate and evaporated. The residue was dissolved in a mixture of 100 ml tetrahydrofuran and 50 ml chloroform. 1.03 g (5 mmol) N,N'-dicyclohexylcarbodiimide and 0.88 g (5 mmol) BOC-glycin were added and stirring was continued for 18 hours at room temperature. Five drops acetic acid were added and after 10 minutes at room temperature the mixture was filtered and the solvents were distilled off. The residue was taken up in acetoacetate, washed with aqueous citric acid, with aqueous sodiumbicarbonate and water, dried with sodiumsulfate and the solvent was distilled off. Chromatography over silicagel with dichloromethanelmethanol 99/1 yielded 1.43 g (79%) (R)-1-tert-butoxycarbonylaminoacetyl-pyrrolidine-2-carboxylic acid benzyl ester as colorless oil.

MS m/e (%): 363 (M+H⁺, 1), 306 (29), 289 (10), 114 (44), 91 (76), 70 (100), 57 (64).

b) (R)-1-[[3-[2-[(R)-2-Benzyloxycarbonyl-pyrrolidin-1-yl]-2-oxo-ethoxy]-ureido]-pyrrolidine-2-carboxylic Acid Benzyl Ester 8.6 ml trifluoric acid were added dropwise at 0° C. to a solution of 1.57 g (4.34 mmol) (R)-1-tert-butoxycarbonylaminoacetyl-pyrrolidine-2-carboxylic acid benzyl ester in 8.6 ml dichloromethane and stirring was continued for half an hour at room temperature. The solution was washed with aqueous sodiumbicarbonate, dried with sodiumsulfate and evaporated. The residue was dissolved in 200 ml dichloromethane and stirred with 0.21 g (0.7 mmol) triphosgene and 1.8 ml (13 mmol) triethylamine for four hours at room temperature. The mixture was extracted with 1N hydrochloric acid, dried with sodiumsulfate and evaporated. The remaining 1.15 g residue were chromatographed over silicagel with dichloromethanelmethanol 96/4 and the fractions containing product were chromatographed again over silicagel with dichloromethanelacetonelformic acid 80/15/5 to yield 0.23 g (33%) (R)-1-[[3-[2-[(R)-2-benzyloxycarbonyl-pyrrolidin-1-yl]-2-oxo-ethoxy]-ureido]-pyrrolidine-2-carboxylic acid benzyl ester as an oil.

MS-ISP: 551 (M+H)⁺.

(R)-1-[[3-[2-[(R)-2-Carboxy-pyrrolidin-1-yl]-2-oxo-ethoxy]-ureido]-pyrrolidine-2-carboxylic Acid 0.14 g (0.36 mmol) (R)-1-[[3-[2-[(R)-2-benzyloxycarbonyl-pyrrolidin-1-yl]-2-oxo-ethoxy]-ureido]-pyrrolidine-2-carboxylic acid benzyl ester in 60 ml ethanol were hydrogenated in the presence of 40 mg 5% Pd on carbon. Filtration, evaporation of the solvent and crystallization from methanol/ethylacetate yielded 0.07 g (52%) as white crystals with melting point 157–160° C.

EXAMPLE 18

(R)-1-[10-[(R)-2-Carboxy-pyrrolidin-1-yl]-10-oxo-decanoyl]-pyrrolidine-2-carboxylic Acid Ca Salt (1:1)

A mixture of 1.20 g (5 mmol) sebacoyl chloride, 1.15 g (10 mmol) D-proline and 1.4 ml (10 mmol) triethylamine in 100 ml dimethylformamide was stirred over the weekend at ambient temperature. The solvent was distilled off under vacuum. The residue was taken up with 40 ml aqueous citric caid acid and extracted with ethylacetate. Evaporation of the solvent and chromatography over silicagel with chloroform/acetonlformic acid 80/5/15 yielded 1.21 g (R)-1-[10-[(R)-2-carboxy-pyrrolidin-1-yl]-10-oxo-decanoyl]-pyrrolidine-2-carboxylic acid as an oil.

MS-ISP: 397 (M+H)⁺.

0.89 g (2.24 mmol) of this oil were dissolved in 50 ml ethanol and stirred with 0.175 g (2.24 mmol) calciumhydroxide for 48 hours. The suspesion was filtered. The solid reue was taken up in 15 ml water, weed to 80° C., filtrated when hot and evaporated. The residue was suspended in ether, filtered and washed with ether to yield 0.5 g (R)-1-[10-[(R)-2-carboxy-pyrrolidin-1-yl]-10-oxo-decanoyl]-pyrrolidine-2-carboxylic acid Ca salt (1:1) as a white solid.

C (theory) 55.28 H (theory) 6.96 N (theory) 6.45

C (found) 55.29 H (found) 7.11 N (found) 6.08

EXAMPLE 19

(R)-1-[8-[(R)-2-Carboxy-pyrrolidin-1-yl)-8-oxo-octanoyl]-pyrrolidine-2-carboxylic Acid Ca salt (1:1)

A mixture of 1.10 g (5 mmol) suberoyl chloride, 1.15 g (10 mmol) D-proline and 1.5 ml (10 mmol) triethylamine in 100 ml dimethylformamide was stirred over 20 hours at ambient temperature. The solvent was distilled off under vacuum. The residue was taken up with 40 ml aqueous citric caid acid and extracted with ethylacetate. Evaporation of the solvent and chromatography over silicagel with chloroform/aceton/formic acid 80/51/15 yielded 0.8 g (R)-1-[8-[(R)-2-carboxy-pyrrolidin-1-yl)-8-oxo-octanoyl]-pyrrolidine-2-carboxylic acid as an oil.

MS-ISN: 367 (M–H)⁻.

0.79 g (2.15 mmol) of this oil were dissolved in 40 ml ethanol and stirred with 0.167 g (2.15 mmol) calciumhydroxide for 20 hours.

The suspension was filtered and the solid residue was almost dissolved in 25 ml water. The solution was filtrated and evaporated to yield 0.5 g (R)-1-[8[(R)-2-carboxy-pyrrolidin-1-yl)-8-oxo-octanoyl]-pyrrolidine-2-carboxylic acid Ca salt (1:1) as a white solid.

EXAMPLE 20

(R)-1-[4'-[(R)-2-Carboxy-pyrrolidin-1-yl-carbonyl]-[2,2]-bithiazolyl-4-yl]pyrrolidine-2-carboxylic Acid a) (R)-1-[4'-[(R)-2-Carboxypyrrolidin-1-yl-carbonyl]-[2,2]-bithiazolyl-4-yl]pyrrolidine-2-carboxyolic Acid Benzyl Ester Thionylchloride (2 mg was added to a solution of 0.26 g(1 mmol) [2,2']bithiazolyl-4,4'-dicarboxylic acid in 20 ml tetramethylurea and the mixture was stirred for three days at room temperature. Excess thionylchloride and the solvent were distilled off under vacuum. The residue was three times taken up in dimethylformamide and evaporated and then dissolved in 50 ml pyridine. 0.28 g (1.1 mmol) D-prolinebenzylester hydrochloride were added and stirring continued at room temperature for 24 hours. The solvent was distilled off, the residue taken up in acetoacetate and extracted with 2N HCl and brine. Drying with sodiumcarbonate, evaporation of the solvent and chromatography on silicagel with acetoacetate/hexane 1:1 yielded 0.094 g (R)-1-[4'-[(R)-2-carboxy-pyrrolidin-1-yl-carbonyl]-(2,2]-bithiazolyl-4-yl]pyrrolidine-2-carboxyolic acid benzyl ester.

MS m/e(%): 630 (M+, 24), 539 (17), 495 (44), 449 (51), 380 (25), 329 (33), 313 (30), 223 (38), 194 (83), 180 (66), 145 (24), 137 (21), 91 (100).

b) (R)-1-[4'-[(R)-2-Carboxy-pyrrolidin-1-yl-carbonyl]-[2,2]-bithiazolyl-4-yl]pyrrolidine-2-carboxylic Acid g (0.08 mmol) (R)-1-[4'-[(R)-2-benzyloxycarbonyl-pyrrolidin-1-yl][2,2]-bithiazol-4-yl]pyrrolidine-2-carboxylic acid benzyl ester in 50 ml methanol were stirred with 5 ml 2N sodiumhydoxide solution at room temperature for 64 hours.

After addition of 2N hydrochloric acid until pH 1 the mixture was extracted with dichloromethane. The extracts were dried with sodiumsulfate and evaporated. Chromatography ocer silicagel with dichloromethane/acetone/ formic acid 80/15/5 gave 0.04 g (R)-1-[4'-[(R)-2-Carboxy-pyrrolidin-1-ylcarbonyl]-[2,2]-bithiazolyl-4-yl]pyrrolidine-2-carboxylic acid as colorless solid.

MS-ISP: 451 (M+H)+.

EXAMPLE 21

(R)-1-[[(R)-2-Carboxy-pyrrolidin-1-yl]-acetyl]-pyrrolidine-2-carboxylic acid a) (R)-Pyrrolidine-2-carboxylic Acid tert-Butyl Ester The title compound was prepared according to a literature procedure (M. Thorsen, T. P. Andersen, U. Pedersen, B. Yde and S. O. Lawesson, *Tetrahedron*, 41:5633–5636 (1985).

Starting from 25.0 g (217 mmol) D-proline, 27.52 g (74%) of (R)-pyrrolidine-2-carboxylic acid tert-butyl ester were obtained as a colorless oil.

a) (R)-Pyrrolidine-2-carboxylic Acid tert-Butyl Ester

To a solution of 64.9 g (322 mmol) bromoacetyl bromide in 250 ml dichloromethane at 0° C. was added dropwise a solution of 27.5 g (161 mmol) (R)-pyrrolidine-2-carboxylic acid tert-butyl ester and 30 ml (177 mmol) Nethyidiisopropylamine in 150 ml dichloromethane within 40 min. The reaction mixture was allowed to warm to room temperature overnight and was poored into 600 ml of water. The organic phase was separated and the water phase was extracted with 600 ml dichloromethane. The combined organic phases were washed with saturated sodium bicarbonate solution and brine, dried (magnesium sulfate) and evaporated to yield 44.1 g (94%) of the title compound as a brown oil that crystallized upon standing at room temperature.

Melting point 51.5–53.2° C.

c) (R)-1-[[(R)-2-tert-Butoxycarbonyl-pyrrolidin-1-yl]-acetyl]-pyrrolidine-2-carboxylic Acid tert-Butyl Ester To a solution of 34.3 g (200 mmol) (R)-(1)-bromoacetyl-pyrrolidine-2-carboxylic acid tert-butyl ester in 350 ml dichloromethane at 0° C.were added dropwise 27.9 ml (200 mmol) triethylamine. After stirring for 45 min at this temperature, 17.8 g (200 mmol) bromoacetyl bromide were added dropwise.

Stirring was continued at 0° C. for 3 h and 250 ml 1 N hydrochloric acid solution were added. The organic phase was separated and was washed with saturated sodiuicarbonate solution and brine, dritomagnesium sulfate) and evaporated to yield 45 g of a brown oil. Trituration with ethyl acetate and cooling to −78° C. gave 7.1 g (9%) of a pale yellow solid. Melting point 75.0–76.0° C. MS m/e (%): 405 (M+Na+, 11), 383 (M+H+, 100).

d) (R)-1-[[(R)-2-Carboxy-pyrrolidin-1-yl]-acetyl]-pyrrolidine-2-carboxylic Acid

A solution of 382 mg (1.0 mmol) (R)-1-[[(R)-2-tert-butoxycarbonyl-pyrrolidin-1-yl]-acetyl]-pyrrolidine-2-carboxylic acid tert-butyl ester in 4 ml trifluoroacetic acid was stirred for 3 h at room temperature. The solvent was removed in vacuo and the residue suspended in 10 ml ether. The resulting suspension was stirred overnight. Filtration and drying gave 300 mg (quantitative) of RO-64-2799/000 as a pale yellow amorphous and hygroscopic solid which still contains trace amounts of trifluoroacetic acid.

MS m/e (%): 269 (M−H−, 4.5), 113 ($CF_3CO_2^-$, 100).

EXAMPLE 22

(R)-1-[[4-[2-[(R)-2-Carboxy-pyrrolidin-1-yl]-2-oxo-ethoxy]-phenoxy]-acetyl]-pyrrolidine-2-carboxylic Acid a) (R)-1-[[4-[2-[(R)-2-tert-Butoxycarbonyl-pyrrolidin-1-yl]-2-oxo-ethoxy]-phenoxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 110 mg (1.0 mmol) hydroquinone in 2 ml dimethylformamide. Stirring was continued for 2–3 min and a solution of 584 mg (2.0 mmol) (R)-(1)bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 380 mg (71%) of the title compound as a colorless oil.

MS m/e (%): 550 (M+$NH_4^+$, 100), 477 (23), 421 (65).

b) (R)-1-[[4-[2-[(R)-2-carboxy-pyrrolidin-1-yl]-2-oxo-ethoxy]phenoxy]-acetyl]-pyrrolidine-2-carboxylic Acid A solution of 350 mg (0.66 mmol) (R)-1-[[4-(2-[(R)-2-tert-butoxycarbonyl-pyrrolidin-1-yl]-2-oxo-ethoxy]-phenoxy]-acetyl]-pyrrolidine-2-carboxylic acid tert-butyl ester in 4 ml trifluoroacetic acid was stirred for 3 h at room temperature. The solvent was removed in vacuo and the residue suspended in 10 ml ether. The resulting suspension was stirred overnight. Filtration and drying gave 265 mg (96%) of the title compound as a white powder.

MS m/e (%): 443 (M+Na+, 48), 438 (M+$NH_4^+$, 39), 421 (M+$H^{30}$, 100).

EXAMPLE 23

(R)-1-[[4-[2-[(R)-2-Carboxy-pyrrolidin-1-yl]-2-oxo-ethoxy]-2,3,5,6-tetrafluoro-phenoxy]-acetyl]-pyrrolidine-2-carboxylic Acid a) (R)-1-[[4-[2-[(R)-2-tert-Butoxycarbonyl-pyrrolidin-1-yl]-2-oxo-ethoxy]-2,3,5,6-tetrafluoro-phenoxy]-acetyl]-pyrrolidine-2-carboxylic Acid tert-Butyl Ester To a solution of 185 mg (1.65 mmol) potassium tert-butylate in 1 ml dimethylformamide at room temperature was added dropwise a solution of 137 mg (0.75 mmol) tetrafluorohydroquinone in 1 ml dimethylformamide. Stirring was continued for ~3 min and a solution of 438 mg (1.50 mmol) (R)(1)-bromoacetyl-pyrrolidine-2-carboxylic acid tert-butyl ester in 2 ml dimethylformamide was added within 1–2 min. The reaction mixture was stirred for additional 4 h at room temperature. The solvent was removed in vacuo and the residue purified by flash-chromatography to yield 87 mg (19%) of the title compound as a white foam.

MS m/e (%): 622 (M+NH$_4^+$, 100), 549 (32), 493 (57).

b) (R)-1-[[4-[2-[(R)-2-Carboxy-pyrrolidin-1-yl]-2-oxo-ethoxy]-2,3,5,6-tetrafluoro-phenoxy]-acetyl]-pyrrolidine-2-carboxylic Acid A solution of 80 mg (0.13 mmol) (R)-1-[[4-[2-[(R)-2-tert-butoxycarbonyl-pyrrolidin-1-yl]-2-oxo-ethoxy]-2,3,5,6-tetrafluoro-phenoxy]-acetyl]-pyrrolidine-2-carboxylic acid teiktyl ester in 1.5 ml trifluoroacetic awas stirred for 4 h at room temperature. The solvent was removed in vacuo and the residue suspended in 10 ml ether. The resulting suspension was stirred overnight. Filtration and drying gave 64 mg (96%) of the title compound as a white powder.

MS m/e (%): 491 (M–H$^-$, 100).

EXAMPLE 24

(R)-1-[[4-[2-[(R)-2-Carboxy-pyrrolidin-1-yl]-2-oxo-ethoxy]-2-chloro-phenoxy]acetyl]-pyrrolidine-2-carboxylic Acid a) (R)-1-[[4-[2-[(R)-2-tert-Butoxycarbonyl-pyrrolidin-1-yl]-2-oxo-ethoxy]-2-chloro-phenoxy]-acetyl]-pyrrolidine-2-carboxylic Acid tert-Butyl Ester To a solution of 185 mg (1.65 mmol) potassium tert-butylate in 1 ml dimethylformamide at room temperature was added dropwise a solution of 108 mg (0.75 mmol) chlorohydroquinone in 1 ml dimethylformamide. Stirring was continued for 2–3 min and a solution of 438 mg (1.50 mmol) (R)-(1)-bromoacetyl-pyrrolidine-2-carboxylic acid tert-butyl ester in 2 ml dimethylformamide was added within 1–2 min. The reaction mixture was stirred for additional 4 h at room temperature. The solvent was removed in vacuo and the residue purified by flash-chromatography to yield 149 mg (35%) of the title compound as a white foam.

MS m/e (%): 584 (M+NH$_4^+$, 100), 511 (48), 455 (96).

b) (R)-1-[[4-[2-[(R)-2-Carboxy-pyrrolidin-1-yl]-2-oxo-ethoxy]-2-chlorophenoxyl-acetyl]-pyrrolidine-2-carboxylic Acid A solution of 140 mg (0.25 mmol) (R)-1-[[4-[2-[(R)-2-tert-butoxycarbonyl-pyrrolidin-1-yl]-2-oxo-ethoxy]-2-chloro-phenoxy]-acetyl]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 126 mg (quantitative) of the title compound as a white powder.

MS m/e (%): 453 (M–H$^-$, 100).

EXAMPLE 25

(R)-1-[[4-[2-[(R)-2-Carboxy-pyrrolidin-1-yl]-2-oxo-ethoxy]-2-methoxy-phenoxy]-acetyl]-pyrrolidine-2-carboxylic Acid a) (R)-1-[[4-[2-[(R)-2-tert-Butoxycarbonyl-pyrrolidin-1-yl]-2-oxo-ethoxy]-2-methoxy-phenoxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 140 mg (1.0 mmol) methoxyhydroquinone in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 280 mg (50%) of the title compound as a colorless oil.

MS m/e (%): 580 (M+NH$_4^+$, 100), 563 (M+H$^+$, 75), 507 (62), 451 (67).

(R)-1-[[4-2-[(R)-2-Carboxy-pyrrolidin-1-yl]-2-oxo-ethoxy]-2-methoxy-phenoxy]-acetyl]-pyrrolidine-2-carboxylic Acid A solution of 250 mg (0.44 mmol) (R)-1-[[4-2-[(R)-2-tert-butoxycarbonyl-pyrrolidin-1-yl]-2-oxo-ethoxy]-2-methoxy-phenoxy]-acetyl]-pyrrolidine-2-carboxylic acid tert-butyl ester in 4 ml trifluoroacetic acid was stirred for 3 h at room temperature. The solvent was removed in vacuo and the residue suspended in 10 ml ether. The resulting suspension was stirred overnight. Filtration and drying gave 188 mg (94%) of the title compound as a white powder.

MS m/e (%): 473 (M+Na$^+$, 45), 468 (M+NH$_4^+$, 24), 451 (M+H$^+$, 100).

EXAMPLE 26

Mixture of (R)-1-[(4-hydroxy-3- and -2-methoxy-phenoxy)-acetyl]-pyrrolidine-2-carboxylic Acid a) Mixture of (R)-1-[(4-Hydroxy-3- and -2-methoxy-phenoxy)-acetyl]-pyrrolidine-2-carboxylic Acid tert-Butyl Ester The title compounds were formed as side products during the preparation of (R)-1-[[4-[2-[(R)-2-tert-butoxycarbonyl-pyrrolidin-1-yl]-2-oxo-ethoxy]-2-methoxy-phenoxy]-acetyl]-pyrrolidine-2-carboxylic acid tert-butyl ester. Isolation and purification by flash-chromatography gave 80 mg (23%) of RO-64-2915/000 as a colorless oil.

$^1$H-NMR (CDCl$_3$), ppm): 1.41 (s, 2.4H), 1.45 (s, 6.6H), 1.81–2.32 (m, 4H), 3.55–3.82 (m, 2H), 3.75 (s, 3H), 4.39–4.78 (m, 3H), 6.16–6.26 (m, 1H) 6.40–6.43 (m, 1H), 6.67–6.74 (m, 1H).

b) Mixture of (R)-1-[(4-Hydroxy-3- and -2-methoxy-phenoxy)-acetyl]-pyrrolidine-2-carboxylic Acid To a solution of 80 mg (0.23 mmol) mixture of (R)-1-[(4-hydroxy-3- and -2-methoxy-phenoxy)-acetyl]-pyrrolidine-2-carboxylic acid tert-butyl ester in 1 ml dichloromethane were added 5 ml of a 4 N solution of hydrochloric acid in dioxane. After 24 h, the solvent was removed in vacuo and the residue suspended in 10 ml ether. The resulting suspension was stirred overnight.

Filtration and drying gave 65 mg (97%) of the title compound as a white powder.

MS m/e (%): 296 (M+H$^+$, 100).

EXAMPLE 27

(R)-1-[[3-[2-[(R)-2-Carboxy-pyrrolidin-1-yl]-2-oxo-ethoxy]-phenoxy]-acetyl]-pyrrolidine-2-carboxylic Acid a) (R)-1-[[3-[2-[(R)-2-tert-Butoxycarbonyl-pyrrolidin-1-yl]-2-oxo-ethoxy]phenoxy]-acetyl]-pyrrolidine-2-carboxylic Acid tert-Butyl Ester To a solution of 561 mg (5.0 mmol) potassium tert-butylat in 4 ml dimethylformamide at room temperature was added dropwise a solution of 275 mg (2.5 mmol) resorcinol in 4 ml dimethylformamide. Stirring was continued for 2–3 min and a solution of 1.46 mg (5.0 mmol) (R)-(1)-bromoacetyl-pyrrolidine-2-carboxylic acid tert-butyl ester in 5 ml dimethylformamide was added within 1–2 min. The reaction mixture was stirred for additional 3 h at room temperature. The solvent was removed in vacuo and the residue purified by flash-chromatography to yield 830 mg (62%) of the title compound as a colorless oil.

MS m/e (%): 550 (M+$NH_4^+$, 100), 533 (M+$H^+$, 95), 477 (48), 421 (95).

b) (R)-1-[[3-[2-[(R)-2-Carboxy-pyrrolidin-1-yl]-2-oxo-ethoxy]-phenoxy]-acetyl]-pyrrolidine-2-carboxylic Acid A solution of 750 mg (1.41 mmol) (R)-1-[[3-[2-[(R)-2-tert-Butoxycarbonyl-pyrrolidin-1-yl]-2-oxo-ethoxy]-phenoxy]-acetyl]-pyrrolidine-2-carboxylic acid tert-butyl ester in 6 ml trifluoroacetic acid was stirred for 3 h at room temperature. The solvent was removed in vacuo and the residue suspended in 15 ml ether. The resulting suspension was stirred overnight. Filtration and drying gave 581 mg (98%) of the title compound as a white powder.

MS m/e (%): 443 (M+$Na^+$, 32), 438 (M+$NH_4^+$, 20), 421 (M+$H^+$, 100).

EXAMPLE 28

(R)-1-[(3-Hydroxy-phenoxy)-acetyl]-pyrrolidine-2-carboxylic Acid a) (R)-1-[(3-Hydroxy-phenoxy)-acetyl]-pyrrolidine-2-carboxylic Acid tert-Butyl Ester The title compound was formed as side product during the preparation of (R)-1-[[3-[2-[(R)-2-tert-butoxycarbonyl-pyrrolidin-1-yl]-2-oxo-ethoxy]-phenoxy]acetyl]-pyrrolidine-2-carboxylic acid tert-butyl ester. Isolation and purification by flash-chromatography gave 120 mg (37%) of RO-64-2802/000 as a colorless oil.

MS m/e (%): 344 (M+$Na^+$, 9), 322 (M+$H^+$, 73), 266 (100).

b) (R)-1-[(3-Hydroxy-phenoxy)-acetyl]-pyrrolidine-2-carboxylic Acid

To a solution of 120 mg (0.37 mmol)) (R)-1-[(3-hydroxy-phenoxy)-acetyl]-pyrrolidine-2-carboxylic acid tert-butyl ester in 1 ml dichloromethane were added 5 ml of a 4 N solution of hydrochloric acid in dioxane. After 3 d, the solvent was removed in vacuo and the residue suspended in 10 ml ether. The resulting suspension was stirred overnight. Filtration and drying gave 95 mg (97%) of the title compound as a white powder.

MS m/e (%): 264 (M−$H^-$, 100).

EXAMPLE 29

(R)-1-[[3-[2-[(R)-2-Carboxy-pyrrolidin-1-yl]-2-oxo-ethoxy]-2-methyl-phenoxy]acetyl]-pyrrolidine-2-carboxylic Acid a) (R)-1-[[3-[2-[(R)-2-tert-Butoxycarbonyl-pyrrolidin-1-yl]-2-oxo-ethoxy]-2-methyl-phenoxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 124 mg (1.0 mmol) 2,6-dihydroxytoluene in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 335 mg (61%) of the title compound as a colorless oil.

MS m/e (%): 564 (M+$NH_4^+$, 100), 491 (27), 435 (71).

b) (R)-1-[[3-[2-[(R)-2-Carboxy-pyrrolidin-1-yl]-2-oxo-ethoxy]-2-methyl-phenoxy]-acetyl]-pyrrolidine-2-carboxylic Acid A solution of 300 mg (0.55 mmol) (R)-1-[[3-[2-[(R)-2-tert-butoxycarbonyl-pyrrolidin-1-yl]-2-oxo-ethoxy]-2-methyl-phenoxy]-acetyl]-pyrrolidine-2-carboxylic acid tert-butyl ester in 4 ml trifluoroacetic acid was stirred for 3 h at room temperature. The solvent was removed in vacuo and the residue suspended in 10 ml ether. The resulting suspension was stirred overnight. Filtration and drying gave 226 mg (95%) of the title compound as a white powder.

MS m/e (%): 457 (M+$Na^+$, 54), 452 (M+$NH_4^+$, 55), 435 (M+$H^+$, 100).

EXAMPLE 30

(R)-1-[[3-[2-[(R)-2-Carboxy-pyrrolidin-1-yl]-2-oxo-ethoxy]-5-methoxy-phenoxy]acetyl]-pyrrolidine-2-carboxylic Acid a) (R)-1-[[3-[2-[(R)-2-tert-Butoxycarbonyl-pyrrolidin-1-yl]-2-oxo-ethoxy]-5-methoxy-phenoxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 140 mg (1.0 mmol) 5-methoxyresorcinol in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 407 mg (72%) of the title compound as a colorless oil.

MS m/e (%): 580 (M+$NH_4^+$, 98), 563 (M+$H^+$, 100), 507 (54), 451 (95).

b) (R)-1-[[3-[2-[(R)-2-Carboxy-pyrrolidin-1-yl]-2-oxo-ethoxy]-5-methoxy-phenoxy]-acetyl]-pyrrolidine-2-carboxylic Acid A solution of 370 mg (0.66 mmol) (R)-1-[[3-[2-[(R)-2-tert-butoxycarbonyl-pyrrolidin-1-yl]-2-oxo-ethoxy]-5-methoxy-phenoxy]-acetyl]-pyrrolidine-2-carboxylic acid tert-butyl ester in 4 ml trifluoroacetic acid was stirred for 3 h at room temperature. The solvent was removed in vacuo and the residue suspended in 10 ml ether. The resulting suspension was stirred overnight. Filtration and drying gave 287 mg (97%) of the title compound as a white powder.

MS m/e (%): 473 (M+$Na^+$, 45), 468 (M+$NH_4^+$, 30), 451 (M+$H^+$, 100).

EXAMPLE 31

(R)-1-[[3-[2-[(R)-2-Carboxy-pyrrolidin-1-yl]-2-oxo-ethoxy]-5-methoxycarbonyl-phenoxy]-acetyl]-pyrrolidine-2-carboxylic Acid a) (R)-1-[[3-[2-[(R)-2-tert-Butoxycarbonyl-pyrrolidin-1-yl]-2-oxo-ethoxy]-5-methoxycarbonyl-phenoxy]-acetyl]-pyrrolidine-2-carboxylic Acid tert-Butyl Ester To a solution of 595 mg (5.3 mmol) potassium tert-butylate in 4 ml dimethylformamide at room temperature was added dropwise a solution of 420 mg (2.5 mmol) 3,5-dihydroxybenzoate in 4 ml dimethylformamide. Stirring was continued for 2–3 min and a solution of 1.46 mg (5.0 mmol) (R)(1)-bromoacetyl-pyrrolidine-2-carboxylic acid tert-butyl ester in 5 ml dimethylformamide was added within 1–2 min. The reaction mixture was stirred for additional 2 h at room temperature. The solvent was removed in vacuo and the residue purified by flash-chromatography to yield 1.01 g (68%) of the title compound as a colorless oil.

MS m/e (%): 608 (M+NH$_4^+$, 92), 591 (M+H$^+$, 48), 535 (41), 479 (100).

b) (R)-1-[[3-[2-[(R)-2-Carboxy-pyrrolidin-1-yl]-2-oxo-ethoxy]-5-methoxycarbonyl-phenoxy]-acetyl]-pyrrolidine-2-carboxylic Acid A solution of 710 mg (1.2 mmol) (R)-1-[[3-[2-[(R)-2-tert-butoxycarbonyl-pyrrolidin-1-yl]-2-oxo-ethoxy]-5-methoxycarbonyl-phenoxy]-acetyl]-pyrrolidine-2-carboxylic acid tert-butyl ester in 10 ml trifluoroacetic acid was stirred for 3 h at room temperature. The solvent was removed in vacuo and the residue suspended in 20 ml ether. The resulting suspension was stirred overnight.

Filtration and drying gave 540 mg (94%) of the title compound as a white powder.

MS m/e (%): 477 (M–H$^-$, 100).

EXAMPLE 32

(R)-1-[[3-Carboxy-5-[2-[(R)-2-carboxy-pyrrolidin-1-yl]-2-oxo-ethoxy]-phenoxy]acetyl]-pyrrolidine-2-carboxylic Acid To 10 ml of a 0.5 N lithium hydroxide solution in methanol/water=3:1 were added 100 mg (0.2 mmol) of (R)-1-[[3-[2-[(R)-2-carboxy-pyrrolidin-1-yl]-2-oxo-ethoxy]-5-methoxycarbonyl-phenoxy]-acetyl]-pyrrolidine-2-carboxylic acid. The solution was allowed to stand at room temperature for 24 h. The mixture was adjusted to pH 6 by dropwise addition of hydrochloric acid solution and lyophilized to give 800 mg of a white powder. The product was isolated by chromatography using an ion exchange resin (Dowex). Lyophilization gave 20 mg (22%) of the title compound as a white powder.

MS m/e (%): 487 (M+Na$^+$, 61), 482 (M+NH$_4^+$, 54), 465 (M+H$^+$, 100).

EXAMPLE 33 a) (R)-1-[[-3-[2-[(R)-2-tert-Butoxycarbonyl-pyrrolidin-1-yl]-2-oxo-ethoxy]-5-cyano-phenoxy]-acetyl]-pyrrolidine-2-carboxylic Acid tert-Butyl Ester To a solution of 1.35 g (10 mmol) 3,5-dihydroxybenzonitrile and 5.84 g (20 mmol) (R)-(1)-bromoacetyl-pyrrolidine-2-carboxylic acid tert-butyl ester in 25 ml dimethylformamide at room temperature were added 7 g anhydrous potassium carbonate. After stirring for additional 20 h, the potassium salts were filtered off and the solvent was removed in vacuo. The residue was purified by flash-chromatography to yield 4.77 g (86%) of the title compound as a colorless foam.

MS m/e (%): 575 (M+NH$_4^+$, 100), 558 (M+H$^+$, 42), 502 (35), 446 (85).

b) (R)-1-[[3-[2-[(R)-2-Carboxy-pyrrolidin-1-yl]-2-oxo-ethoxy]-5-cyano-phenoxy]-acetyl]-pyrrolidine-2-carboxylic Acid A solution of 280 mg (0.5 mmol) (R)-1-[[3-[2-[(R)-2-tert-butoxycarbonyl-pyrrolidin-1-yl]-2-oxo-ethoxy]-5-cyano-phenoxy]-acetyl]-pyrrolidine-2-carboxylic acid tert-butyl ester in 5 ml trifluoroacetic acid was stirred for 18 h at room temperature. The solvent was removed in vacuo and the residue suspended in 10 ml ether. The resulting suspension was stirred overnight. Filtration and drying gave 280 mg (72%) of the title compound as a white powder.

MS m/e (%): 444 (M–H$^-$, 100).

EXAMPLE 34

(R)-1-[[3-[2-[(R)-2-Carboxy-pyrrolidin-1-yl]-2-oxo-ethoxy]-5-1H-tetrazol-5-yl-phenoxy]-acetyl]-pyrrolidine-2-carboxylic Acid To a solution of 110 mg (0.2 mmol) (R)-1-[[3-[2-[(R)-2-tert-Butoxycarbonyl-pyrrolidin-1-yl]-2-oxo-ethoxy]-5-cyano-phenoxy]-acetyl]-pyrrolidine-2-carboxylic acid tert-butyl ester in 10 ml 1,2-dimethoxyethane were added 200 mg (0.6 mmol) tributyltin azide. The mixture was heated at reflux for 3 days. After cooling to room temperature, 1.4 g of gaseous hydrochloric acid were bubbled into the solution to obtain a 4 N hydrochloric acid solution in 1,2-dimethoxyethane and stirring was continued for 12 h. The solvent was removed in vacuo and the oily residue was triturated with ether to give 61 mg (92%) of the title compound as a pale yellow amorphous solid.

MS m/e (%): 511 (Mt+Na$^+$, 41), 506 (M+NH$_4^+$, 32), 489 (M+H$^+$, 100).

EXAMPLE 35

(R)-1-[[3-[2-[(R)-2-Carboxy-pyrrolidin-1-yl]-2-oxo-ethoxy]-5-hydroxy-phenoxylacety]acetyl]-pyrrolidine-2-carboxylic Acid a) (R)-1-[[3-[2-[(R)-2-tert-Butoxycarbonyl-pyrrolidin-1-yl]-2-oxo-ethoxy]-1-5 hydroxy-phenoxy]-acetyl]-pyrrolidine-2-carboxylic Acid tert-Butyl Ester To a solution of 95 mg (0.75 mmol) phloroglucinol and 438 mg (1.5 mmol) (R)-(1)-bromoacetyl-pyrrolidine-2-carboxylic acid tert-butyl ester in 2 ml dimethylformamide at room temperature were added 520 mg anhydrous potassium carbonate. After stirring overnight, the potassium salts were filtered off and the solvent was removed in vacuo. The residue was purified by flash-chromatography to yield 50 mg (12%) of the title compound as a white foam.

MS m/e (%): 566 (M+NH$_4^+$, 96), 549 (M+H$^+$, 88), 493 (47), 437 (100).

b) (R)-1-[[3-[2-[(R)-2-Carboxy-pyrrolidin-1-yl]-2-oxo-ethoxy]-5-hydroxy-phenoxy]-acetyl]-pyrrolidin-2-carboxylic Acid A solution of 46 mg (0.084 mmol) (R)-1-[[3-[2-[(R)-2-tert-butoxycarbonyl-pyrrolidin-1-yl]-2-oxo-ethoxy]-5-hydroxy-phenoxy]-acetyl]-pyrrolidine-2-carboxylic acid tert-butyl ester in 1 ml trifluoroacetic acid was stirred for 4 h at room temperature. The solvent was removed in vacuo and the residue suspended in 5 ml ether. The resulting suspension was stirred overnight. Filtration and drying gave 35 mg (96%) of the title compound as a light brown powder.

MS m/e (%): 435 (M–H$^-$, 100).

EXAMPLE 36

(R)-1-[[3,5-Bis-[2-[(R)-2-carboxy-pyrrolidin-1-yl]-2-oxo-ethoxy]-phenoxy]-acetyl]-pyrrolidine-2-carboxylic Acid a) (R)-1-[[3,5-Bis-[2-[(R)-2-tert-butoxycarbonyl-pyrrolidin-1-yl]-2-oxo-ethoxy]-phenoxy]-acetyl]-pyrrolidine-2-carboxylic Acid tert-Butyl Ester To a solution of 95 mg (0.75 mmol) phloroglucinol and 220 mg (0.75 mmol) (R)-(1)-bromoacetyl-pyrrolidine-2-carboxylic acid tert-butyl ester in 2 ml dimethylformamide at room temperature were added 520 mg anhydrous potassium carbonate. After 2 h and 6 h stirring at room temperature, 220 mg (0.75 mmol) (R)-(1)-bromoacetyl-pyrrolidine-2-carboxylic acid tert-butyl ester were added (per addition) and stirring was continued for 18 h. The potassium salts were filtered off and the solvent was removed in vacuo. The residue was purified by flash-chromatography to yield 465 mg (82%) of the title compound as a colorless foam.

MS mie (%): 777 ($M+NH_4^+$, 100), 760 ($M+H^+$, 4), 704 (11), 648 (22), 592 (22).

b) (R)-1-[[3,5-Bis-[2-[(R)-2-carboxy-pyrrolidin-1-yl]-2-oxo-ethoxy]-phenoxy]acetyl]-pyrrolidine-2-carboxylic Acid A solution of 350 mg (0.47 mmol) (R)-1-[[3,5-bis-[2-[(R)-2-tert-butoxycarbonyl-pyrrolidin-1-yl]-2-oxo-ethoxy]-phenoxy]-acetyl]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 254 mg (92%) of the title compound as a light brown powder.

MS m/e (%): 614 ($M+Na^+$, 73), 609 ($M+NH_4^+$, 100), 592 ($M+H^+$, 56).

EXAMPLE 37

Mixture of (E)- and (Z)-(R)-1-[[3-[2-[(R)-2-carboxy-pyrrolidin-1-yl]-2-oxo-ethoxy]-5-(N-hydroxycarbamimidoyl)-phenoxy]-acetyl]-pyrrolidine-2-carboxylic Acid a) Mixture of (E)- and (Z)-(R)-1-[[3-[2-[(R)-2-tert-butoxycarbonyl-pyrrolidin-1-yl]-2-oxo-ethoxy]-5-(N-hydroxycarbamimidoyl)-phenoxy]-acetyl]-pyrrolidine-2-carboxylic Acid tert-Butyl Ester To a solution of 1.25 g (17.9 mmol) hydroxylamine hydrochloride in 6 ml dimethyl sulfoxide were added 1.82 g (18 mmol) triethylamine. An insoluble material was filtered off and was washed with 5 ml tetrahydrofuran. The filtrate was concentrated in vacuo at 100 mbar to remove tetrahydrofuran and 2.0 g (3.59 mmol) (R)-1-[[3-[2-[(R)-2-tert-butoxycarbonyl-pyrrolidin-1-yl]-2-oxo-ethoxy]-5-cyano-phenoxy]-acetyl]-pyrrolidine-2-carboxylic acid tert-butyl ester were added. After stirring for 20 h at 75° C., the reaction mixture was diluted with water and extracted with ethyl acetate. The organic solution was extracted with 1 N hydrochloric acid solution. The aqueous solution was adjusted to pH 10 with 1 N sodium hydroxide solution and extracted with ethyl acetate. The organic solution was washed with water, dried (sodium sulfate) and evaporated to give 1.74 g of the title compound as a colorless foam.

MS m/e (%): 613 ($M+Na^+$, 7), 591 ($M+H^+$, 100), 535 (21), 479 (15).

b) Mixture of (E)- and (Z)-(R)-1-[[3-[2-[(R)-2-carboxy-pyrrolidin-1-yl]-2-oxo-ethoxy]-5-(N-hydroxycarbamimidoyl)-phenoxy]-acetyl]-pyrrolidine-2-carboxylic Acid A solution of 120 mg (0.2 mmol) mixture of (E)- and (Z)-(R)-1-[[3-[2-[(R)-2-tert-butoxycarbonyl-pyrrolidin-1-yl]-2-oxo-ethoxy]-5-(N-hydroxycarbamimidoyl)-phenoxy]-acetyl]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 96 mg (quantitative) of the title compound as a light brown powder.

MS m/e (%): 501 ($M+Na^+$, 31), 479 ($M+H^+$, 100).

EXAMPLE 38

(R)-1-[[3-[2-[(R)-2-Carboxy-pyrrolidin-1-yl]-2-oxo-ethoxy]-5-(5-oxo-4,5-dihydro-[1,2,4]oxadiazol-3-yl)-phenoxy]-acetyl]-pyrrolidine-2-carboxylic Acid a) (R)-1-[[3-[2-[(R)-2-tert-Butoxycarbonyl-pyrrolidin-1-yl]-2-oxo-ethoxy]-5-(5 oxo-4,5-dihydro-[1,2,4]oxadiazol-3-yl)-phenoxy]-pyrrolidine-2-carboxylic Acid tert-Butyl Ester To an ice-cooled solution of 300 mg (0.51 mmol) mixture of (E)- and (Z)-(R)-1-[[3-[2-[(R)-2-tert-butoxycarbonyl-pyrrolidin-1-yl]-2-oxo-ethoxy]-5-(N-hydroxycarbamimidoyl)-phenoxy]-acetyl]-pyrrolidine-2-carboxylic acid tert-butyl ester and 43 mg (0.55 mmol) pyridine in 2 ml dimethylformamide were added dropwise 200 mg (0.51 mmol) 2-ethylhexyl chloroformate. The mixture was stirred at 0° C. for 30 min, diluted with water and extracted with ethyl acetate. The organic phase was dried (sodium sulfate) evaporated and the oily residue was dissolved in 20 ml toluene. After 16 h stirring at room temperature, the toluene solution was washed with brine, dried (sodium sulfate) and filtered over silica gel to give 280 mg (89%) of the title compound as a viscous oil.

MS m/e (%): 639 ($M+Na^+$, 51), 634 ($M+NH_4^+$, 100), 617 ($M+H^+$, 14), 561 (40), 505 (79).

b) (R)-1-[[3-[2-[(R)-2-Carboxy-pyrrolidin-1-yl]-2-oxo-ethoxy]-5-(5-oxo-4,5-dihydro-[1,2,4]oxadiazol-3-yl)-phenoxy]-acetyl]-pyrrolidine-2-carboxylic Acid A solution of 220 mg (0.36 mmol) (R)-1-[[3-[2-[(R)-2-tert-butoxycarbonyl-pyrrolidin-1-yl]-2-oxo-ethoxy]-5-(5-oxo-4,5-dihydro-[1,2,4]oxadiazol-3-yl)-phenoxy]-acetyl]-pyrrolidine-2-carboxyl acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 135 mg (74%) of the title compound as a light brown powder.

MS m/e (%): 527 ($M+Na^+$, 73), 522 ($M+NH_4^+$, 75), 505 ($M+H^+$, 100).

EXAMPLE 39

(R)-1-[[3-2-[(R)-2-Carbonxy-pyrrolidin-1-yl]-2-oxo-ethoxy]-5-(2-oxo-2,3-dihydro-[1,2,5]-oxathiadiazol-4-yl)-phenoxy]-acetyl]-pyrrolidine-2-carboxylic Acid (Config. of S-oxide R:S=1:1)

a) (R)-1-[[3-[2-[(R)-2-tert-Butoxycarbonyl-pyrrolidin-1-yl]-2-oxo-ethoxy]-5-(2-oxo-2,3-dihydro-[1,2,3,5]oxathiadiazol-4-yl)-phenoxy]-acetyl]-pyrrolidine-2-carboxylic Acid tert-Butyl Ester (Config. of S-oxide R:S=1:1)

To an ice-cooled solution of 300 mg (0.51 mmol) mixture of (E)- and (Z)-(R)-1-[[3-[2-[(R)-2-tert-butoxycaronyl-pyrrolidin-1-yl]-2-oxo-ethoxy]-5-(N-hydroxycarbamimidoyl)-phenoxy]-acetyl]-pyrrolidine-2-carboxylic acid tert-butyl ester and 80 mg (1 mmol) pyridine in 2 ml dichloromethane were added dropwise 60 mg (0.51 mmol) thionyl chloride (dissolved in 0.3 ml dichloromethane). The mixture was stirred at 0° C. for 45 min, diluted with dichloromethane, washed with water, dried (sodium sulfate) and evaporated. Flash-chromatography gave 190 mg (59%) of the title compound as a semi-solid liquid.

MS m/e (%): 659 (M+Na$^+$, 14), 654 (M+NH$_4^+$, 100), 637 (M+H$^+$, 11), 581 (14), 525 (74).

b) (R)-1-[[3-[2-[(R)-2-Carbonxy-pyrrolidin-1-yl]-2-oxo-ethoxy]-5-(2-oxo-2,3-dihydro-[1,2,3,5]oxathiadiazol-4-yl)-phenoxy]-acetyl]-pyrrolidine-2-carboxylic Acid (Config. of S-oxide R:S=1:1)

A solution of 165 mg (0.26 mmol) (R)-1-[[3-[2-[(R)-2-tert-butoxycarbonyl-pyrrolidin-1-yl]-2-oxo-ethoxy]-5-(2-oxo-2,3-dihydro-[1,2,3,5]oxathiadiazol-4-yl)-phenoxy]-acetyl]-pyrrolidine-2-carboxylic acid tert-butyl ester (config. of S-oxide R:S=1:1) in 1.5 ml trifluoroacetic acid was stirred for 4 h at room temperature. The solvent was removed in vacuo and the residue suspended in 10 ml ether. The resulting suspension was stirred overnight. Filtration and drying gave 115 mg (85%) of the title compound as a light brown powder.

MS m/e (%): 547 (M+Na$^+$, 65), 542 (M+NH$_4^+$, 86), 525 (M+H$^+$, 100).

EXAMPLE 40

(R)-1-[[3-[2-[(R)-2-Carboxy-pyrrolidin-1-yl]-2-oxo-ethoxy]-5-(5-tert-butylsulfanyl-[1,2,4]oxadiazol-3-yl)-phenoxy]-acetyl]-pyrrolidine-2-carboxylic Acid a) (R)-1-[[3-[2-[(R)-2-tert-Butoxycarbonyl-pyrrolidin-1-yl]-2-oxo-ethoxy]-5-(5-thioxo-4,5-dihydro-1,2,4]oxadiazol-3-yl)-phenoxy]-acetyl]-pyrrolidine-2-carboxylic Acid tert-Butyl Ester A mixture of 515 mg (0.87 mmol) mixture of (E)- and (Z)-(R)-1-[[3-[2-[(R)-2 tert-butoxycarbonyl-pyrrolidin-1-yl]-2-oxo-ethoxy]-5-(N-hydroxycarbamimidoyl)-phenoxy]-acetyl]-pyrrolidine-2-carboxylic acid tert-butyl ester, 177 mg (0.94 mmol) 1,1'-thiocarbonyidiimidazole and 530 mg (3.5 mmol) 1,8-diazabicyclo[5.4.0]undec-7-ene in 10 ml acetonitrile was stirred at room temperature for 4 h. The mixture was concentrated in in vacuo, diluted with water, adjusted to pH 4–5 with 1 N hydrochloric acid solution and extracted with ethyl acetate. The extract was concentrated again, the residue was dissolved in 100 ml 1 N sodium hydroxide solution and washed with ether. The aqueous solution was adjusted to pH 4 with 1 N hydrochloric acid solution and was extracted with ethyl acetate. The organic phase was washed with water, dried (sodium sulfate) and was evaporated to give 490 mg (89%) of the title compound as a pale brown foam.

MS m/e (%): 655 (M+Na$^+$, 35), 650 (M+NH$_4^+$, 100), 633 (M+H$^+$, 14), 577 (31), 521 (52).

b) (R)-1-[[3-[2-[(R)-2-Carboxy-pyrrolidin-1-yl]-2-oxo-ethoxy]-5-(5-tert-butylsulfanyl-[1,2,4]oxadiazol-3-yl)-phenoxy]-acetyl]-pyrrolidine-2-carboxylic Acid A solution of 315 mg (0.5 mmol) (R)-1-[[3-[2-[(R)-2-tert-butoxycarbonyl-pyrrolidin-1-yl]-2-oxo-ethoxy]-5-(5-thioxo-4,5-dihydro-[1,2,4]oxadiazol-3-yl)-phenoxy]-acetyl]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 160 mg (57%) of the title compound as a white powder.

MS m/e (%): 599 (M+Na$^+$, 54), 594 (M+NH$_4^+$, 71), 577 (M+H$^+$, 100), 521 (37).

EXAMPLE 41

(R)-1-[[2-[2-[(R)-2-carboxy-pyrrolidin-1-yl]-2-oxo-ethoxy]-3-methoxy-phenoxy]-acetyl]-pyrrolidine-2-carboxylic Acid a) (R)-1-[[2-[2-[(R)-2-tert-Butoxycarbonyl-pyrrolidin-1-yl]-2-oxo-ethoxy]-3-methoxy-phenoxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 140 mg (1.0 mmol) pyrogallol-1-methyl ether in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 375 mg (67%) of the title compound as a colorless oil.

MS m/e (%): 580 (M+NH$_4^+$, 14), 563 (M+H$^+$, 100), 507 (14), 451 (12).

b) (R)-1-[[2-[2-[(R)-2-carboxy-pyrrolidin-1-yl]-2-oxo-ethoxy]-3-methoxy-phenoxy]-acetyl]-pyrrolidine-2-carboxylic Acid A solution of 345 mg (0.61 mmol) (R)-1-[[2-[2-[(R)-2-tert-butoxycarbonyl-pyrrolidin-1-yl]-2-oxo-ethoxy]-3-methoxy-phenoxy]-acetyl]-pyrrolidine-2-carboxylic acid tert-butyl ester in 4 ml trifluoroacetic acid was stirred for 4 h at room temperature. The solvent was removed in vacuo and the residue suspended in 10 ml ether. The resulting suspension was stirred overnight. Filtration and drying gave 265 mg (96%) of the title compound as a white powder.

MS m/e (%): 473 (M+Na$^+$, 54), 451 (M+H$^+$, 100).

EXAMPLE 42

(R)-1-[[2-[2-[(R)-2-Carboxy-pyrrolidin-1-yl]-2-oxo-ethoxy]-3-methyl-phenoxy]acetyl]-pyrrolidine-2-carboxylic Acid a) (R)-1-[[2-[2-[(R)-2-tert-Butoxycarbonyl-pyrrolidin-1-yl]-2-oxo-ethoxy]-3-methyl-phenoxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 124 mg (1.0 mmol) 3-methylcatechol in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 356 mg (65%) of the title compound as a colorless oil.

MS m/e (%): 547 (M+H$^+$, 100), 491 (14), 435 (17).

b) (R)-1-[[2-[2-[(R)-2-Carboxy-pyrrolidin-1-yl]-2-oxo-ethoxy]-3-methyl-phenoxy]-acetyl]-pyrrolidine-2-carboxylic Acid A solution of 325 mg (0.60 mmol) (R)-1-[[2-[2-[(R)-2-tert-butoxycarbonyl-pyrrolidin-1-yl]-2-oxo-ethoxy]-3-methyl-phenoxy]-acetyl]-pyrrolid ine-2-carboxylic acid tert-butyl ester in 4 ml trifluoroacetic acid was stirred for 3 h at room temperature. The solvent was removed in vacuo and the residue suspended in 10 ml ether. The resulting suspension was stirred overnight. Filtration and drying have 235 mg (91%) of the title compound as a white powder.

MS m/e (%): 457 (M+Na$^+$, 59), 435 (M+H$^+$, 100).

EXAMPLE 43

(R)-1-[[2-[2-[(R)-2-Carboxy-pyrrolidin-1-yl]-2-oxo-ethoxy]-3,4,5,6-tetrachloro-phenoxy]-acetyl]-pyrrolidine-2-carboxylic Acid a) (R)-1-[[2-[2-[(R)-2-tert-Butoxycarbonyl-pyrrolidin-1-yl]-2-oxo-ethoxy]-3,4,5,6-tetrachloro-phenoxy]-acetyl]pyrrolidine-2-carboxylic Acid tert-Butyl Ester To a solution of 185 mg (1.65 mmol) potassium tert-butylate in 1 ml dimethylformamide at room temperature was added dropwise a solution of 186 mg (0.75 mmol) tetrachlorocatechol in 1 ml dimethylformamide. Stirring was continued for 2–3 min and a solution of 438 mg (1.50 mmol) (R)-(1)-bromoacetyl-pyrrolidine-2-carboxylic acid tert-butyl ester in 2 ml dimethylformamide was added within 1–2 min. The reaction mixture was stirred for additional 4 h at room temperature. The solvent was removed in vacuo and the residue purified by flash-chromatography to yield 229 mg (45%) of the title compound as a white foam.

MS m/e (%): 671 (M+H$^+$, 100), 615 (19), 559 (14).

b) (R)-1-[[2-[2-[(R)-2-Carboxy-pyrrolidin-1-yl]-2-oxo-ethoxy]-3,4,5,6-tetrachloro-phenoxy]-acetyl]-pyrrolidine-2-carboxylic Acid A solution of 220 mg (0.34 mmol) (R)-1-[[2-[2-[(R)-2-tert-butoxycarbonyl-pyrrolidin-1-yl]-2-oxo-ethoxy]-3,4,5,6-tetrachloro-phenoxy]-acetyl]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 172 mg (94%) of the title compound as a white powder.

MS m/e (%): 559 (M–H$^-$, 100).

EXAMPLE 44

R)-1-[[6-[2-[(R)-2-Carboxy-pyrrolidin-1-yl)-2-oxo-ethoxy]-naphthalen-2-yloxy]acetyl]-pyrrolidine-2-carboxylic Acid a) (R)-1-[[6-[2-[(R)-2-tert-Butoxycarbonyl-pyrrolidin-1-yl)-2-oxo-ethoxy]naphthalen-2-yloxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 160 mg (1.0 mmol) 2,6-dihydroxynaphthalene in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 120 mg (21%) of the title compound as a white solid.

MS m/e (%): 605 (M+Na$^+$, 14), 600 (M+NH$_4^+$, 92), 583 (M+H$^+$, 5), 527 (32), 471 (100).

b) R)-1-[[6-[2-[(R)-2-Carboxy-pyrrolidin-1-yl)-2-oxo-ethoxy]-naphthalen-2-yloxy]-acetyl]-pyrrolidine-2-carboxylic Acid A solution of 75 mg (0.13 mmol) (R)-1-[[6-[2-[(R)-2-tert-butoxycarbonyl-pyrrolidin-1-yl)-2-oxo-ethoxy]-naphthalen-2-yloxy]-acetyl]-pyrrolidine-2-carboxylic acid tert-butyl ester in 1.5 ml trifluoroacetic acid was stirred for 18 h at room temperature. The solvent was removed in vacuo and the residue suspended in 10 ml ether. The resulting suspension was stirred overnight. Filtration and drying gave 60 mg (98%) of the title compound as a white powder.

MS m/e (%): 493 (M+Na$^+$, 58), 488 (M+NH$_4^+$, 33), 471 (M+H$^+$, 100).

EXAMPLE 45

(R)-1-[[5-[2-[(R)-2-Carboxy-pyrrolidin-1-yl]-2-oxo-ethoxy]-naphthalen-1-yloxy]acetyl]-pyrrolidine-2-carboxylic Acid a) (R)-1-[[5-[2-[(R)-2-tert-Butoxycarbonyl-pyrrolidin-1-yl]-2-oxo-ethoxy]-naphthalen-1-yloxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 160 mg (1.0 mmol) 1,5-dihydroxynaphthalene in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 470 mg (81%) of the title compound as a pale yellow foam.

MS m/e (%): 605 (M+Na$^+$, 10), 600 (M+NH$_4^+$, 100), 527 (20), 471 (63).

b) (R)-1-[[5-[2-[(R)-2-Carboxy-pyrrolidin-1-yl]-2-oxo-ethoxy]-naphthalen-1-yloxy]-acetyl]-pyrrolidine-2-carboxylic Acid A solution of 290 mg (0.5 mmol) (R)-1-[[5-[2-[(R)-2-tert-butoxycarbonyl-pyrrolidin-1-yl]-2-oxo-ethoxy]-naphehalen-1-yloxy]-acetyl]-pyrrolidine-2-carboxylic acid tert-butyl ester in 5 ml trifluoroacetic acid was stirred for 18 h at room temperature. The solvent was removed in vacuo and the residue suspended in 10 ml ether. The resulting suspension was stirred overnight. Filtration and drying gave 230 mg (98%) of the title compound as a white powder.

MS m/e (%): 493 (M+Na$^+$, 45), 488 (M+NH$_4^+$, 37), 471 (M+H$^+$, 100).

EXAMPLE 46

(R)-1-[[3-[2-[(R)-2-Carboxy-pyrrolidin-1-yl]-2-oxo-ethoxy]-naphthalen-2-yloxy]acetyl]-pyrrolidine-2-carboxylic Acid a) (R)-1-[[3-[2-[(R)-2-tert-Butoxycarbonyl-pyrrolidin-1-yl]-2-oxo-ethoxy]-naphthalen-2-yloxy]-acetyl]-pyrrolidine-2-carboxylic Acid tert-Butyl Ester To a solution of 236 mg (2.1 mmol) potassium tert-butylate in 2 ml dimethylformamide at room temperature was added dropwise a solution of 160 mg (1.0 mmol) 2,3-dihydroxynaphthalene in 2 ml dimethylformamide. Stirring was continued for 2–3 min and a solution of 584 mg (2.0 mmol) (R)-(1)-bromoacetyl-pyrrolidine-2-carboxylic acid tert-butyl ester in 4 ml dimethylformamide was added within 1–2 min. The reaction mixture was stirred for additional 3 h at room temperature. The solvent was removed in vacuo and the residue purified by flash-chromatography to yield 310 mg (53%) of the title compound as a colorless oil.

MS m/e (%): 605 (M+Na$^+$, 27), 600 (M+NH$_4^+$, 16), 583 (M+H$^+$, 100), 527 (16), 471 (24).

b) (R)-1-[[3-[2-[(R)-2-Carboxy-pyrrolidin-1-yl]-2-oxo-ethoxy]-naphthalen-2-yloxy]-acetyl]-pyrrolidine-2-carboxylic Acid A solution of 230 mg (0.4 mmol) (R)-1-[[3-[2-[(R)-2-tert-butoxycarbonyl-pyrrolidin-1-yl]-2-oxo-ethoxy]naphthalen-2-yloxy]-acetyl]-pyrrolidine-2-carboxylic acid tert-butyl ester in 5 ml trifluoroacetic acid was stirred for 18 h at room temperature. The solvent was removed in vacuo and the residue suspended in 10 ml ether. The resulting suspension was stirred overnight. Filtration and drying gave 180 mg (96%) of the title compound as a white powder.

MS m/e (%): 469 (M–H$^-$, 100).

EXAMPLE 47

(R)-1-[[2'-[2-[(R)-2-Carboxy-pyrrolidin-1-yl]-2-oxo-ethoxy]-biphenyl-2-yloxy]acetyl]-pyrrolidine-2-carboxylic Acid a) (R)-1-[[2'-[2-[(R)-2-tert-Butoxycarbonyl-pyrrolidin-1-yl]-2-oxo-ethoxy]biphenyl-2-yloxy]-acetyle]-pyrrolidine-2-carboxylic Acid tert-Butyl Ester To a solution of 160 mg (1.44 mmol) potassium tert-butylate in 1.6 ml dimethylformamide at room temperature was added dropwise a solution of 127 mg (0.69 mmol) 2,2'-dihydroxybiphenyl in 1 ml dimethylformamide. Stirring was continued for 2–3 min and a solution of 400 mg (1.37 mmol) (R)-(1)-bromoacetyl-pyrrolidine-2-caarboxylic acid tert-butyl ester in 4 ml dimethylformamide was added within 1–2 min. The reaction mixture was stirred overnight at room temperature. The solvent was removed in vacuo and the residue purified by flash-chromatography to yield 84 mg (20%) of the title compound as a light brown oil.

MS m/e (%): 631 (M+Na$^+$, 22), 626 (M+NH$_4^+$, 100), 609 (M+H$^+$, 16).

b) (R)-1-[[2'-[2-[(R)-2-Carboxy-pyrrolidin-1-yl]-2-oxo-ethoxy]-biphenyl-2-yloxy]-acetyl]-pyrrolidine-2-carboxylix Acid A solution of 87 mg (0.14 mmol) (R)-1-[[2'-[2-[(R)-2-tert-butoxycarbonyl-pyrrolidin-1-yl]-2-oxo-ethoxy]-biphenyl-2-yloxy]-acetyl]-pyrrolidine-2-carboxylic acid tert-butyl ester in 1 ml trifluoroacetic acid was stirred for 4 h at room temperature. The solvent was removed in vacuo and the residue suspended in 10 ml ether. The resulting suspension was stirred overnight. Filtration and drying gave 31 mg (44%) of the title compound as a light brown powder.

MS m/e (%): 519 (M+Na$^+$, 62), 497 (M+H$^+$, 100).

EXAMPLE 48

(R)-1-[[4-[2-[(R)-2-Carboxy-pyrrolidin-1-yl)-2-oxo-ethoxy]-naphthalen-1-yloxy]-acetyl]-pyrrolidine-2-carboxylic Acid a) (R)-1-[[4-[2-[(R)-2-tert-Butoxycarbonyl-pyrrolidin-1-yl)-2-oxo-ethoxy]-naphthalen-1-yloxy]-acetyl]-pyrrolidine-2-carboxylic Acid tert-Butyl Ester To a solution of 160 mg (1.44 mmol) potassium tert-butylate in 1.6 ml dimethylformamide at room temperature was added dropwise a solution of 116 mg (0.69 mmol) 1,4-naphthoquinone in 1 ml dimethylformamide. Stirring was continued for 2–3 min and a solution of 400 mg (1.37 mmol) (R)-(1)-bromoacetyl-pyrrolidine-2-carboxylic acid tert-butyl ester in 4 ml dimethylformamide was added within 1–2 min. The reaction mixture was stirred overnight at room temperature. The solvent was removed in vacuo and the residue purified by flash-chromatography to yield 269 mg (67%) of the title compound as a light brown foam.

MS m/e (%): 600 (M+NH$_4^+$, 100).

b) (R)-1-[[4-[2-[(R)-2-Carboxy-pyrrolidin-1-yl)-2-oxo-ethoxy]-naphthalen-1-yloxy]-acetyl]-pyrrolidine-2-carboxylic Acid A solution of 172 mg (0.30 mmol) (R)-1-[[4-[2-[(R)-2-tert-butoxycarbonyl-pyrrolidin-1-yl)-2-oxo-ethoxy]-naphthalen-1-yloxy]-acetyle]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 140 mg (quantitative) of the title compound as a light brown powder.

MS m/e (%): 469 (M–H$^-$, 100).

EXAMPLE 49

(R)-1-[[7-[2-[(R)-2-Carboxy-pyrrolidin-1-yl)-2-oxo-ethoxy]-naphthalen-2-yloxy]-acetyl]-pyrrolidine-2-carboxylic Acid a) (R)-1-[[7-[2-[(R)-2-tert-Butoxycarbonyl-pyrrolidin-1-yl)-2-oxo-ethoxy]naphthalen-2-yloxy]-acetyl]-pyrrolidine-2-carboxylic Acid tert-Butyl Ester To a solution of 110 mg (0.69 mmol) 2,7-dihydroxynaphthalene and 400 mg (1.37 mmol) (R)-(1)-bromoacetyl-pyrrolidine-2-carboxylic acid tert-butyl ester in 1.5 ml dimethylformamide at room temperature were added 480 mg anhydrous potassium carbonate. After stirring for additional 20 h, the potassium salts were filtered off and the solvent was removed in vacuo. The residue was purified by flash-chromatography to yield 296 mg (74%) of the title compound as a white foam.

MS m/e (%): 600 (M+NH$_4^+$, 100), 527 (25), 471 (99).

b) (R)-1-[[7-[2-[(R)-2-Carboxy-pyrrolidin-1-yl)-2-oxo-ethoxy]-naphthalen-2-yloxy]-acetyl]-pyrrolidine-2-carboxylic Acid A solution of 272 mg (0.47 mmol) (R)-1-[[7-[2-[(R)-2-tert-butoxycarbonyl-pyrrolidin-1-yl)-2-oxo-ethoxy]-naphthalen-2-yloxy]-acetyl]-pyrrolidine-2-carboxylic acid tert-butyl ester in 1.5 ml trifluoroacetic acid was stirred for 4 h at room temperature. The solvent was removed in vacuo and the residue suspended in 10 ml ether. The resulting suspension was stirred overnight. Filtration and drying gave 209 mg (95%) of the title compound as a white powder.

MS m/e (%): 493 (M+Na$^+$, 48), 488 (M+NH$_4^+$, 23), 471 (M+H$^+$, 100).

EXAMPLE 50

(R)-1-[[3-[2-[(R)-2-Carboxy-pyrrolidin-1-yl]-2-oxo-ethylamino]-phenylamino]-acetyl]-pyrrolidine-2-carboxylic acid trifluoroacetate (1:2)

a) (R)-1-[[3-[2-[(R)-2-tert-Butoxycarbonyl-pyrrolidin-1-yl]-2-oxo-ethylamino]phenylamino]-acetyl]-pyrrolidine-2-carboxylic Acid tert-Butyl Ester To a solution of 75 mg (0.69 mmol) 1,3-phenylenediamine and 400 mg (1.37 mmol) (R)-(1)-bromoacetyl-pyrrolidine-2-carboxylic acid tert-butyl ester in 3 ml dichloromethane at room temperature were added 0.21 ml (1.5 mmol) triethylamine. The reaction mixture was stirred overnight at room temperature. The organic phase was washed with 1 N sodium carbonate solution and brine, dried (sodium sulfate) and evaporated. The residue was purified by flash-chromatography to yield 285 mg (78%) of the title compound as a light brown foam.

MS m/e (%): 553 (M+Na$^+$, 15), 531 (M+H$^+$, 100), 475 (20), 419 (10).

b) (R)-1-[[3-[2-[(R)-2-Carboxy-pyrrolidin-1-yl]-2-oxo-ethylamino]phenylamino]-acetyl]-pyrrolidine-2-carboxylic Acid Trifluoroacetate (1:2)

A solution of 170 mg (0.32 mmol) (R)-1-[[3-[2-[(R)-2-tert-butoxycarbonyl-pyrrolidin-1-yl]-2-oxo-ethylamino]-phenylamino]-acetyl]-pyrrolidine-2-carboxylic acid tert-butyl ester in 4 ml trifluoroacetic acid was stirred for 4 h at room temperature. The solvent was removed in vacuo and the residue suspended in 10 ml ether. The resulting suspension was stirred overnight. Filtration and drying gave 130 mg (63%) of the title compound as a brown foam.

MS m/e (%): 417 (M–H$^-$, 100).

EXAMPLE 51

(R)-1-[[4-[2-[(R)-2-Carboxy-pyrrolidin-1-yl]-2-oxo-ethylamino]-phenylamino]-acetyl]-pyrrolidine-2-carboxylic Acid Trifluoroacetate (1:2)

a) (R)-1-[[4-[2-[(R)-2-tert-Butoxycarbonyl-pyrrolidin-1-yl]-2-oxo-ethylamino]phenylamino]-acetyl]-pyrrolidine-2-carboxylic Acid tert-Butyl Ester To a solution of 75 mg (0.69 mmol) 1,4-phenylenediamine and 400 mg (1.37 mmol) (R)-(1)-bromoacetyl-pyrrolidine-2-carboxylic acid tert-butyl ester in 4 ml tetrahydrofuran at room temperature were added 190 mg anhydrous potassium carbonate. The reaction mixture was stirred overnight at 40° C. The potassium salts were filtered off and the solvent was removed in vacuo. The residue was purified by flash-chromatography to yield 180 mg (50%) of the title compound as a brown foam.

MS m/e (%): 553 (M+Na$^+$, 26), 531 (M+H$^+$, 100).

b) (R)-1-[[4-[2-[(R)-2-Carboxy-pyrrolidin-1-yl]-2-oxo-ethylamino]phenylamino]-acetyl]-pyrrolidine-2-carboxylic Acid Trifluoroacetate (1:2)

A solution of 168 mg (0.32 mmol) (R)-1-[[4-[2-[(R)-2-tert-butoxycarbonyl-pyrrolidin-1-yl]-2-oxo-ethylamino]-phenylamino]-acetyl]-pyrrolidine-2-carboxylic acid tert-butyl ester in 2 ml trifluoroacetic acid was stirred for 4 h at room temperature. The solvent was removed, the residue suspended in toluene and the solvent removed again to eliminate excess trifluoroacetic acid. The residue was re-suspended in 10 ml ether. The resulting suspension was stirred overnight. Filtration and drying gave 160 mg (78%) of the title compound as a brown foam.

MS m/e (%): 417 (M−H$^-$, 100).

EXAMPLE 52

(R)-1-[[[2-[(R)-2-Carbonyl-pyrrolidin-1-yl]-2-oxo-ethyl]-butyl-amino]-acetyl]pyrrolidine-2-carboxylic Acid Trifluoroacetate (1:1 a) (R)-1-[[[2-[(R)-2-tert-Butoxycarbonyl-pyrrolidin-1-yl]-2-oxo-ethyl]-butylamino]-acetyl]-pyrrolidine-2-carboxylic Acid tert-Butyl Ester To a solution of 136 mg (1.86 mmol) butylamine and 995 mg (3.40 mmol) (R)-(1)-bromoacetyl-pyrrolidine-2-carboxylic acid tert-butyl ester in 4 ml dichloromethane at room temperature were added 0.52 ml (3.74 mmol) triethylamine. The suspension was stirred overnight at room temperature. The organic phase was washed with 1 N sodium carbonate solution and brine, dried (sodium sulfate) and evaporated. The residue was purified by flash-chromatography to yield 830 mg (98%) of the title compound as a light brown oil.

MS m/e (%): 524 (2M+Ni$^+$, 37), 496 (M+H$^+$, 100), 468 (2), 440 (7).

b) (R)-1-[[[2-[(R)-2-Carbonyl-pyrrolidin-1-yl]-2-oxo-ethyl]-butyl-amino]-acetyl]-pyrrolidine-2-carboxylic Acid Trifluoroacetate (1:1)

A solution of 50 mg (0.1 mmol) (R)-1-[[[2-[(R)-2-tert-butoxycarbonyl-pyrrolidin1-yl]-2-oxo-ethyl]-butyl]-amino]-acetyl]-pyrrolidine-2-carboxylic acid tert-butyl ester in 0.2 ml trifluoroacetic acid was stirred for 4 h at room temperature. The solvent was removed in vacuo and the residue suspended in 10 ml ether. The resulting suspension was stirred overnight. Filtration and drying gave 46 mg (92%) of the title compound as a light brown powder.

MS m/e (%): 382 (M−H$^-$, 100).

EXAMPLE 53

(R)-1-[[[2-[(R)-2-Carbonyl-pyrrolidin-1-yl]-2-oxo-ethyl]-(2-methoxy-ethyl)-amino]-acetyl]-pyrrolidine-2-carboxylic Acid Trifluoroacetate (1:1)

a) (R)-1-[[[2-[(R)-2-tert-Butoxycarbonyl-pyrrolidin-1-yl]-2-oxo-ethyl]-(2-methoxy-ethyl)-amino]-acetyl]-pyrrolidine-2-carboxylic Acid Tert-butyl Ester To a solution of 137 mg (1.83 mmol) 2-methoxyethylamine and 970 mg (3.33 mmol) (R)-(1)-bromoacetyl-pyrrolidine-2-carboxylic acid tert-butyl ester in 4 ml dichloromethane at room temperature were added 0.51 ml (3.66 mmol) triethylamine. The suspension was stirred overnight at room temperature. The organic phase was washed with 1 N sodium carbonate solution and brine, dried (sodium sulfate) and evaporated. The residue was purified by flash-chromatography to yield 397 mg (48%) of the title compound as a light brown oil.

MS m/e (%): 520 (M+Na$^+$, 50), 498 (M+H$^+$, 100).

b. (R)-1-[[[2-[(R)-2-Carbonyl-pyrrolidin-1-yl]-2-oxo-ethyl]-(2-methoxyethyl)amino]-acetyl]-pyrrolidine-2-carboxylic Acid Trifluoroacetate (1:1)

A solution of 367 mg (0.74 mmol) (R)-1-[[[2-[(R)-2-tert-butoxycarbonyl-pyrrolidin-1-yl]-2-oxo-ethyl]-(2-methoxy-ethyl)-amino]-acetyl]-pyrrolidine-2-carboxylic acid tert-butyl ester in 2 ml trifluoroacetic acid was stirred for 3 h at room temperature. The solvent was removed in vacuo and the residue suspended in 10 ml ether. The resulting suspension was stirred overnight. Filtration and drying gave 350 mg (95%) of the title compound as a light brown foam.

MS m/e (%): 384 (M−H$^-$, 100).

EXAMPLE 54

(R)-1-[[Benzyl-[2-[(R)-2-carboxy-pyrrolidin-1-yl]-2-oxo-ethyl]-amino]-acetyl]-pyrrolidine-2-carboxylic Acid Trifluoroacetate (1:1)

a) (R)-1-[[Benzyl-[2-[(R)-2-tert-butoxycarbonyl-pyrrolidin-1-yl]-2-oxo-ethyl]-amino]-acetyl]-pyrrolidine-2-carboxylic Acid Tert-butyl Ester To a solution of 104 mg (0.97 mmol) benzylamine and 514 mg (1.76 mmol) (R)-(1)-bromoacetyl-pyrrolidine-2-carboxylic acid tert-butyl ester in 5 ml dichloromethane at room temperature were added 0.27 ml (1.94 mmol) triethylamine. The suspension was stirred overnight at room temperature. The organic phase was washed with 1 N sodium carbonate solution and brine, dried (sodium sulfate) and evaporated. The residue was purified by flash-chromatography to yield 270 mg (58%) of the title compound as a light brown oil.

MS m/e (%): 552 (M+Na$^+$, 12), 530 (M+H$^+$, 100).

b) (R)-1-[[Benzyl-[2-[(R)-2-carboxy-pyrrolidin-1-yl]-2-oxo-ethyl]-amino]-acetyl]-pyrrolidine-2-carboxylic Acid Trifluoroacetate (1:1)

A solution of 200 mg (0.38 mmol) (R)-1-[[Benzyl-[2-[(R)-2-tert-butoxycarbonyl-pyrrolidin-1-yl]-2-oxo-ethyl]-amino]-acetyl]-pyrrolidine-2-carboxylic acid tert-butyl ester in 2 ml trifluoroacetic acid was stirred for 3 h at room temperature. The solvent was removed in vacuo and the residue suspended in 10 ml ether. The resulting suspension was stirred overnight. Filtration and drying gave 189 mg (94%) of the title compound as white crystals.

MS m/e (%): 440 (M+Na$^+$, 16), 418 (M+H$^+$, 100).

EXAMPLE 55

(R)-1-[[3-[2-[(R)-2-Carboxy-pyrrolidin-1-yl]-2-oxo-ethyl]-1,3-dibutyl-ureido]-acetyl]-pyrrolidine-2-carboxylic Acid a) (R)-1-Butylaminoacetyl-pyrrolidine-2-carboxylic Acid tert-Butyl Ester To a solution of 1.58 ml (16 mmol) butylamine in 1 ml dichloromethane was added dropwise a solution of 470 mg (1.6 mmol) (R)-(1)-bromoacetylpyrrolidine-2-carboxylic acid tert-butyl ester in 2 ml dichloromethane at room temperature. The suspension was stirred overnight. The organic phase was washed with 1 N sodium carbonate solution and brine, dried (sodium sulfate) and evaporated. The residue was purified by flash-chromatography to yield 370 mg (81%) of the title compound as a light brown oil.

MS m/e (%): 285 (M+H$^+$, 100).

b) (R)-1-[[3-[2-[(R)-2-tert-Butoxycarbonyl-pyrrolidin-1-yl]-2-oxo-ethyl]-1,3-dibutyl-ureido]-acetyl]-pyrrolidine-2-carboxylic Acid tert-Butyl Ester To a solution of 165 mg (0.58 mmol) (R)-1-butylaminoacetyl-pyrrolidine-2-carboxylic acid tert-butyl ester in 5 ml toluene were added 305 mg anhydrous sodium carbonate. The suspension was evaporated to dryness and the residue was re-suspended in 2 ml tetrahydrofuran. Then, 1.4 ml (2.88 mmol) of a phosgene solution (20% in toluene) were added and stirring was continued for 6 h at 50° C. The sodium salts were filtered off and washed with tetrahydrofuran. The filtrate was evaporated and 165 mg (0.58 mmol) RO-64-2576/000 dissolved in 2 ml tetrahydrofuran and 305 mg anhydrous sodium carbonate were added again. After stirring overnight at 50° C., the organic phase was washed with 1 N hydrochloric acid solution, dried (magnesium sulfate) and evaporated to give 330 mg (91%) of the tiltle compound as a light brown powder.

MS m/e (%): 617 (M+Na$^+$, 19), 595 (M+H$^+$, 100).

c) (R)-1-[[3-[2-[(R)-2-Carboxy-pyrrolidin-1-yl]-2-oxo-ethyl]-1,3-dibutyl-ureido]-acetyl]-pyrrolidine-2-carboxylic Acid A solution of 278 mg (0.47 mmol) (R)-1-[[3-[2-[(R)-2-tert-butoxycarbonyl-pyrrolidin-1-yl]-2-oxo-ethyl]-1,3-dibutyl-ureido]-acetyl]-pyrrolidine-2-carboxylic acid tert-butyl ester in 2 ml trifluoroacetic acid was stirred for 4 h at room temperature. The solvent was removed in vacuo and the residue was dried to give 167 mg (74%) of the title compound as brown foam.

MS m/e (%): 505 (M+Na$^+$, 11), 487 (33), 483 (M+H$^+$, 33), 485 (100).

EXAMPLE 56

(R)-1-[[1,3-Dibenzyl-3-[2-[(R)-2-carboxy-pyrrolidin-1-yl]-2-oxo-ethyl]-ureido]-acetyl]-pyrrolidine-2-carboxylic Acid a) (R)-1-Benzylaminoacetyl-pyrrolidine-2-carboxylic Acid tert-Butyl Ester To a solution of 1.25 ml (11.4 mmol) benzylamine in 1 ml dichloromethane was added dropwise a solution of 335 mg (1.14 mmol) (R)-(1)-bromoacetyl-pyrrolidine-2-carboxylic acid tert-butyl ester in 2 ml dichloromethane at 0° C. The suspension was stirred for 4 h at this temperature. The organic phase was washed with 1 N sodium carbonate solution and brine, dried (sodium sulfate) and evaporated. The residue was purified by flash-chromatography to yield 312 mg (86%) of the title compound as an amorphous solid.

MS m/e (%): 319 (M+H$^+$, 100).

b) (R)-1-[[1,3-Dibenzyl-3-[2-[(R)-2-tert-butoxycarbonyl-pyrrolidin-1-yl]-2-oxo-ethyl]-ureido]-acetyle]-pyrrolidine-2-carboxylic Acid tert-Butyl Ester To a solution of 233 mg (0.73 mmol) (R)-1-benzylaminoacetyl-pyrrolidine-2-carboxylic acid tert-butyl ester in 2 ml toluene at room temperature were added 0.20 ml (1.34 mmol) triethylamine. Over a period of 3 h, 0.30 ml (0.70 mmol) of a phosgene solution (20% in toluene) were added in 6 portions and stirring was continued for 3 h at room temperature. The organic phase was washed with 1 N hydrochloric acid solution, 1 N sodium carbonate solution and brine, dried (magnesium sulfate) and evaporated. The residue was purified by flash-chromatography to give 245 mg (50%) of the title compound as a light yellow oil.

MS m/e (%): 685 (M+Na$^+$, 28), 680 (M+NH$_4^+$, 100), 663 (M+H$^+$, 30).

c) (R)-1-[[1,3-Dibenzyl-3-[2-[(R)-2-carboxy-pyrrolidin-1-yl]-2-oxo-ethyl]-ureido]-acetyl]-pyrrolidine-2-carboxylic Acid A solution of 220 mg (0.33 mmol) (R)-1-[[1,3-Dibenzyl-3-[2-[(R)-2-tert-butoxycarbonyl-pyrrodin-1-yl]-2-oxo-ethyl]-ureido]-acetyl]-pyrrolidine-2-carboxylic acid tert-butyl ester in 5 ml 4 N hydrochloric acid solution in dioxane was stirred for 5 h at room temperature. The product was extracted with 1 N sodium hydroxide solution, the basic extract was acidified with 1 N hydrochloric acid solution to pH 4 and the product extracted with ethyl acetate. The organic phase was dried (magnesium sulfate) and evaporated to give 74 mg (41%) of the title compound as a brown oil.

MS m/e (%): 549 (M−H$^-$, 100).

EXAMPLE 57

(R)-1-Benzylaminoacetyl-pyrrolidine-2-carboxylic Acid

The title compound was formed via urea cleavage as side product during the preparation of (R)-1-[[1,3-Dibenzyl-3-[2-[(R)-2-carboxy-pyrrolidin-1-yl]-2-oxo-ethyl]-ureido]-acetyl]-pyrrodine-2-carboxylic acid. It was isolated from the acidified aqueous solution as follows. The water phase was concentrated and the residue was suspended in 2-propanol. Inorganic salts were filtered off over celite. Evaporation and drying gave 78 mg (45%) of (R)-1-benzylaminoacetyl-pyrrolidine-2-carboxylic acid as a colorless foam.

MS m/e (%): 261 (M−H$^-$, 100).

The following general procedures are used in the Examples that follow:

General Procedure A: EDC Coupling Reaction

To a stirred solution of D-proline benzyl ester hydrochloride (2 equiv.), a dicarboxylic acid (1 equiv.), N-methylmorpholine (6 equiv.) and hydroxybenzotriazole (2 equiv.) in dichloromethane at 0° C. was added N-(3-dimethylaminopropyl)-N'-ethylcarbodiimide hydrochloride (2 equiv.) and stirring continued at 0° C. for 2 h and then at room temperature for 16 h. The reaction mixture was then washed sequentially with 1 M hydrochloric acid, saturated sodium bicarbonate solution and finally with saturated brine, and the aqueous phases back-extracted with dichloromethane. The combined organic extracts were dried over sodium sulphate and concentrated in vacuo. Purification by flash chromatography on kieselgel then afforded the title compound.

General Procedure B: Hydrogenolysis of Benzyl Ester

A solution of the benzyl ester in isopropanol was stirred with 5 wt % of 10% palladium on charcoal under 1 atm of hydrogen for 16 h at room temperature. After filtration to remove the catalyst, the reaction mixture was concentrated in vacuo and azeotroped three times with chloroform on a rotary evaporator to remove last traces of isopropanol. The resulting product (often a viscous oil, semi-solid or foam) was triturated in ether and then dried in vacuo (10 mbar) at 50° C. for 16 h.

EXAMPLE 58

(R)-1-[5-[(R)-2-Carboxy-pyrrolidin-1-yl]-2,4-dimethyl-5-oxo-pentanoyl]-pyrrolidine-2-carboxylic Acid (Mixture of 3 Diastereomers)

a) (R)-1-[5-[(R)-2-Benzyloxymethyl-pyrrolidin-1-yl]-2,4-dimethyl-5-oxo-pentanoyl]-pyrrolidine-2-carboxylic Acid Benzyl Ester (Mixture of 3 Diastereomers)

Using General Procedure A with 6.05 g (25 mmol) D-Proline benzyl ester hydrochloride and 2.0 g (12.5 mmol) 2,4-dimethylglutaric acid afforded, after flash chromatography (EtOAc), 4.3 g (64%) of the title compound as a light yellow oil. MS m/e (%): 535 (M+H$^+$, 100).

b) (R)-1-[5-[(R)-2-Carboxy-pyrrolidin-1-yl]-2,4-dimethyl-5-oxo-pentanoyl]-pyrrolidine-2-carboxylic Acid (Mixture of 3 Diastereomers)

Using General Procedure B with 4.30 g (8.05 mmol) (R)-1-[5-[(R)-2-benzyloxymethyl-pyrrolidin-1-yl]-2,4-dimethyl-5-oxo-pentanoyl]-pyrrolidine-2-carboxylic acid benzyl ester (mixture of 3 diastereomers) afforded 2.58 g (91%) of the title compound as a white foam. MS m/e (%): 355 (M+H$^+$, 100).

EXAMPLE 59

(R)-1-[4-[(R)-2-Carboxy-pyrrolidin-1-yl]-2,3-dimethyl-4-oxo-butyryl]-pyrrolidine-2-carboxylic Acid (Mixture of 3 Diastereomers)

a) (R)-1-[4-[(R)-2-Benzyloxycarbonyl-pyrrolidin-1-yl]-2,3-dimethyl-4-oxo-butyryl]-pyrrolidine-2-carboxylic Acid Benzyl Ester (Mixture of 3 Diastereomers)

Using General Procedure A with 2.0 g (8.2 mmol) D-Proline benzyl ester hydrochloride and 600 mg (4.1 mmol) 2,3-dimethylsuccinic acid afforded, after flash chromatography (EtOAc), 1.45 g (69%) of the title compound as a colorless oil. MS m/e (%): 521 (M+H$^+$, 100).

b) (R)-1-[4-[(R)-2-Carboxy-pyrrolidin-1-yl]-2,3-dimethyl-4-oxo-butyryl]-pyrrolidine-2-carboxylic Acid (Mixture of 3 Diastereomers)

Using General Procedure B with 1.45 g (2.78 mmol) (R)-1-[4-[(R)-2-Benzyloxycarbonyl-pyrrolidin-1-yl]-2,3-dimethyl-4-oxo-butyryl]-pyrrolidine-2-carboxylic acid benzyl ester (mixture of 3 diastereomers) afforded 780 mg (80%) of the title compound as a white foam. MS m/e (%): 341 (M+H$^+$, 100).

EXAMPLE 60

(R)-1-[trans-4-[(R)-2-Carboxy-pyrrolidine-1-carbonyl]-cyclohexanecarbonyl]-pyrrolidine-2-carboxylic Acid a) (R)-1-[trans4-[(R)-2-Benzyloxycarbonyl-pyrrolidine-1-carbonyl]-cyclohexanecarbonyl]-pyrrolidine-2-carboxylic Acid Benzyl Ester Using General Procedure A with 2.0 g (8.2 mmol) D-Proline benzyl ester hydrochloride and 700 mg (4.1 mmol) trans-cyclohexane-1,4-dicarboxylic acid afforded, after flash chromatography (EtOAc), 1.67 g (76%) of the title compound as a colorless oil. MS m/e (%): 547 (M+H$^+$, 100).

b) (R)-1-[trans4-[(R)-2-Carboxy-pyrrolidine-1-carbonyl]-cyclohexanecarbonyl]-pyrrolidine-2-carboxylic Acid Using General Procedure B with 1.61 g (2.95 mmol) (R)-1-]tans-4-[(R)-2-Benzyloxycarbonyl-pyrrolidine-1-carbonyl]-cyclohexanecarbonyl]-pyrrolidine-2-carboxylic acid benzyl ester afforded 1.07 g (99%) of the title compound as a white foam. MS m/e (%): 367 (M+H$^+$, 100).

EXAMPLE 61

(R)-1-[cis-4-[(R)-2-Carboxy-pyrrolidine-1-carbonyl]-cyclohexanecarbonyl]-pyrrolidine-2-carboxylic Acid a) (R)-1-[cis4-[(R)-2-Benzyloxycarbonyl-pyrrolidine-1-carbonyl]-cyclohexanecarbonyl]-pyrrolidine-2-carboxylic Acid Benzyl Ester Using General Procedure A with 2.0 g (8.2 mmol) D-Proline benzyl ester hydrochloride and 700 mg (4.1 mmol) cis-cyclohexane-1,4-dicarboxylic acid afforded, after flash chromatography (EtOAc), 2.0 g (91%) of the title compound as a colorless oil. MS m/e (%): 547 (M+H$^+$, 100).

b) (R)-1-[cis-4-[(R)-2-Carboxy-pyrrolidine-1-carbonyl]-cyclohexanecarbonyl]-pyrrolidine-2-carboxylic Acid Using General Procedure B with 2.0 g (3.66 mmol) (R)-1-[cis-4-[(R)-2-Benzyloxycarbonyl-pyrrolidine-1-carbonyl]-cyclohexanecarbonyl]-pyrrolidine-2-carboxylic acid benzyl ester afforded 930 mg (69%) of the title compound as a white foam. MS m/e (%): 365 ([M–H]$^-$, 100).

EXAMPLE 62

(R)-1-[3-[(R)-2-Carboxy-pyrrolidine-1-carbonyl]-cyclohexanecarbonyl]-pyrrolidine-2-carboxylic Acid (Mixture of 3 Diastereomers)

a) (R)-1-[3-[(R)-2-Benzyloxycarbonyl-pyrrolidine-1-carbonyl]-cyclohexanecarbonyl]-pyrrolidine-2-carboxylic Acid Benzyl Ester (Mixture of 3 Diastereomers)

Using General Procedure A with 5.6 g (23.2 mmol) D-Proline benzyl ester hydrochloride and 2.0 g (11.6 mmol) cyclohexane-1,3-dicarboxylic acid afforded, after flash chromatography (EtOAc), 4.4 g (70%) of the title compound as a colorless oil. MS m/e (%): 547 (M+H$^+$, 100).

b) (R)-1-[3-[(R)-2-Carboxy-pyrrolidine-1-carbonyl]-cyclohexanecarbonyl]-pyrrolidine-2-carboxylic Acid (Mixture of 3 Diastereomers)

Using General Procedure B with 4.4 g (8.05 mmol) (R)-1-[3-[(R)-2-Benzyloxycarbonyl-pyrrolidine-1-carbonyl]-cyclohexanecarbonyl]-pyrrolidine2-carboxylic acid benzyl ester (mixture of 3 diastereomers) afforded 2.9 g (98%) of the title compound as a white foam. MS m/e (%): 367 (M+H$^+$, 100).

EXAMPLE 63

Mixture of (R)-1-[(1R,2R)- and -[(1S,2S)-2-[(R)-2-Carboxy-pyrrolidine-1-carbonyl]-cyclohexanecargonyl]-pyrrolidine-2-carboxylic Acid a) Mixture of (R)-1-[(1R,2R)- and [(1S,2S)-2-[(R)-2-Benzyloxycarbonyl-pyrrolidine-1-carbonyl]-cyclohexanecarbonyl]-pyrrolidine-2-carboxylic Acid Benzyl Using General Procedure A with 2.0 g (8.2 mmol) D-Proline benzyl ester hydrochloride and 700 mg (4.1 mmol) trans-cyclohexane-1,2-dicarboxylic acid afforded, after flash chromatography (EtOAc), 1.36 g (62%) of the title compound as a colorless oil. MS m/e (%): 547 (M+H$^+$, 100).

b) Mixture of (R)-1-[(1R,2R)- and -[(1S,2S)-2-[(R)-2-carboxy-pyrrolidine-1-carbonyl]-cyclohexanecarbonyl]-pyrrolidine-2-carboxylic Acid Using General Procedure B with 1.36 g (2.48 mmol) mixture of (R)-1[(1R,2R)- and [(1S,2S)-2-[(R)-2-benzyloxycarbonyl-pyrrolidine-1-carbonyl]-cyclohexanecarbonyl]-pyrrolidine-2-carboxylic acid benzyl afforded 900 mg (99%) of the title compound as a white foam. MS m/e (%): 367 (M+H$^+$, 100).

EXAMPLE 64

(R)-1-[[2,5-Dihydroxy4-[2-[(R)-2-carboxy-pyrrolidin-1-yl]-2-oxo-ethyl]-phenyl]-acetyl]-pyrrolidine-2-carboxylic Acid a) (R)-1-[[4-[2-[(R)-2-Benzyloxycarbonyl-pyrrolidin-1-yl]-2-oxo-ethyl]-2,5-dihydroxy-phenyl]-acetyl]-pyrrodiline-2-carboxylic Acid Benzyl Ester Using General Procedure A with 10.7 g (44.2 mmol) D-Proline benzyl ester hydrochloride and 5.0 g (22.1 mmol) 2,5-dihydroxy-1,4-phenylenediacetic acid afforded, after flash chromatography (gradient: 70–100% EtOAc/hexane), 3.17 g (24%) of the title compound as a colorless foam. MS m/e (%): 601 (M+H$^+$, 100).

b) (R)-1-[[2,5-Dihydroxy-4-[2-[(R)-2-carboxy-pyrrolidin-1-yl]-2-oxo-ethyl]-phenyl]-acetyl]-pyrrolidine-2-carboxylic Acid Using General Procedure B with 3.17 g (5.3 mmol) (R)-1-[[4-[2-[(R)-2-Benzyloxycarbonyl-pyrrolidin-1-yl]-2-oxo-ethyl]-2,5-dihydroxy-phenyl]-acetyl]-pyrrolidine-2-carboxylic acid benzyl ester afforded 2.2 g (99%) of the title compound as a white crystalline solid. MS m/e (%): 421 (M+H$^+$, 100).

EXAMPLE 65

(R)-1-[[3-[2-[(R)-2-Carboxy-pyrrolidin-1-yl]-2-oxo-ethyl]-phenyl]-acetyl]-pyrrolidine-2-carboxylic Acid a) (R)-1-[[3-[2-[(R)-2-Benzyloxycarbonyl-pyrrolidin-1-yl]-2-oxo-ethyl]-phenyl]-acetyl]-pyrrolidine-2-carboxylic Acid Benzyl Ester Using General Procedure A with 2.0 g (8.2 mmol) D-Proline benzyl ester hydrochloride and 800 mg (4.1 mmol) 1,3-phenylenediacetic acid afforded, after flash chromatography (EtOAc), 1.93 g (84%) of the title compound as a colorless oil. MS m/e (%): 586 (M+NH$_4^+$, 100), 569 (M+H$^+$, 60).

b) (R)-1-[[3-[2-[(R)-2-Carboxy-pyrrolidin-1-yl]-2-oxo-ethyl]-phenyl]-acetyl]-pyrrolidine-2-carboxylic Acid Using General Procedure B with 1.84 g (3.2 mmol) (R)-1-[[3-[2-[(R)-2-Benzyloxycarbonyl-pyrrolidin-1-yl]-2-oxo-ethyl]-phenyl]-acetyl]-pyrrolidine-2-carboxylic acid benzyl ester afforded 1.21 g (97%) of the title compound as a white foam. MS m/e (%): 421 (M+H$^+$, 100).

EXAMPLE 66

(R)-1-[4-[(R)-2-Carboxy-pyrrolidine-1-carbonyl]-benzoyl]-pyrrolidine-2-carboxylic Acid a) (R)-1-[4-[(R)-2-Benzyloxycarbonyl-pyrrolidine-1-carbonyl]-benzoyl]-pyrrolidine-2-carboxylic Acid Benzyl Ester Using General Procedure A with 5.8 g (24.0 mmol) D-Proline benzyl ester hydrochloride and 2.0 g (12.0 mmol) benzene-1,4-dioic acid afforded, after flash chromatography (EtOAc), 4.66 g (72%) of the title compound as a yellow oil. MS m/e (%): 558 (M+NH$_4^+$, 100), 541 (M+H$^+$, 95).

b) (R)-1-[4-[(R)-2-Carboxy-pyrrolidine-1-carbonyl]-benzoyl]-pyrrolidine-2-carboxylic Acid Using General Procedure B with 4.66 g (8.62 mmol) (R)-1-[4-[(R)-2-Benzyloxycarbonyl-pyrrolidine-1-carbonyl]-benzoyl]-pyrrolidine-2-carboxylic acid benzyl ester afforded 3.05 g (95%) of the title compound as a colorless foam. MS m/e (%): 378 (M+NH$_4^+$, 100), 361 (M+H$^+$, 55).

EXAMPLE 67

(R)-1-[3-[(R)-2-Carboxy-pyrrolidine-1-carbonyl]-benzoyl]-pyrrolidine-2-carboxylic Acid a) (R)-1-[3-[(R)-2-Benzyloxycarbonyl-pyrrolidine-1-carbonyl]-benzoyl]-pyrrolidine-2-carboxylic Acid Benzyl Ester Using General Procedure A with 5.8 g (24.0 mmol) D-Proline benzyl ester hydrochloride and 2.0 g (12.0 mmol) benzene-1,3-dioic acid afforded, after flash chromatography (EtOAc), 4.68 g (72%) of the title compound as a yellow oil. MS m/e (%): 558 (M+NH$_4^+$, 100), 541 (M+H$^+$, 90).

b) (R)-1-[3-[(R)-2-Carboxy-pyrrolidine-1-carbonyl]-benzoyl]-pyrrolidine-2-carboxylic Acid Using General Procedure B with 2.83 g (5.24 mmol) (R)-1-[3-[(R)-2-Benzyloxycarbonyl-pyrrolidine-1-carbonyl]-benzoyl]-pyrrolidine-2-carboxylic acid benzyl ester afforded 1.9 g (100%) of the title compound as a colorless foam. MS m/e (%): 378 (M+NH$_4^+$, 100), 361 (M+H$^+$, 35).

EXAMPLE 68

(R)-1-[6-[(R)-2-Carboxy-pyrrolidine-1-carbonyl]-pyridine-2-carbonyl]-pyrrolidine-2-carboxylic Acid a) (R)-1-[6-[(R)-2-Benzyloxycarbonyl-pyrrolidine-1-carbonyl]-pyridine-2-carbonyl]-pyrrolidine-2-carboxylic Acid Benzyl Ester Using General Procedure A with 5.8 g (24.0 mmol) D-Proline benzyl ester hydrochloride and 2.0 g (12.0 mmol) pyridine-2,6-dicarboxylic acid afforded, after flash chromatography (EtOAc), 5.0 g (77%) of the title compound as a yellow oil. MS m/e (%): 559 (M+NH$_4^+$, 60), 542 (M+H$^+$, 100).

b) (R)-1-[6-[(R)-2-Carboxy-pyrrolidine-1-carbonyl]-pyridine-2-carbonyl]-pyrrolidine-2-carboxylic Acid Using General Procedure B with 3.2 g (5.9 mmol) (R)-1-[6-[(R)-2-Benzyloxycarbonyl-pyrrolidine-1-carbonyl]-pyridine-2-carbonyl]-pyrrolidine-2-carboxylic acid benzyl ester afforded 1.9 g (90%) of the title compound as a white foam. MS m/e (%): 379 (M+NH$_4^+$, 100), 362 (M+H$^+$, 65).

EXAMPLE 69

(R)-1-[5-[(R)-2-Carboxy-pyrrolidine-1-carbonyl]-thiophene-2-carbonyl]-pyrrolidine-2-carboxylic Acid a) (R)-1-[5-[(R)-2-Benzyloxycarbonyl-pyrrolidine-1-carbonyl]-thiophene-2-carbonyl]-pyrrolidine-2-carboxylic Acid Benzyl Ester Using General Procedure A with 2.0 g (8.2 mmol) D-Proline benzyl ester hydrochloride and 700 mg (4.1 mmol) thiophene-2,5-dicarboxylic acid afforded, after flash chromatography (EtOAc), 1.84 g (84%) of the title compound as a yellow crystalline solid. MS m/e (%): 564 (M+NH$_4^+$, 70), 547 (M+H$^+$, 100).

b) (R)-1-[5-[(R)-2-Carboxy-pyrrolidine-1-carbonyl]-thiophene-2-carbonyl]-pyrrolidine-2-carboxylic Acid Using General Procedure B with 1.84 g (3.3 mmol) (R)-1-[5-[(R)-2-benzyloxycarbonyl-pyrrolidine-1-carbonyl]-thiophene-2-carbonyl]-pyrrolidine2-carboxylic acid benzyl ester afforded 770 mg (63%) of the title compound RO-64-2667/000 as a white crystalline solid. MS m/e (%): 365 ([M–H]⁻, 65).

EXAMPLE 70

(R)-1-[5-[(R)-2-Carboxy-pyrrolidine-1-carbonyl]-furan-2-carbonyl]-pyrrolidine-2-carboxylic Acid a) (R)-1-[5-[(R)-2-Benzyloxycarbonyl-pyrrolidine-1-carbonyl]-furan-2-carbonyl]-pyrrolidine-2-carboxylic Acid Benzyl Ester Using General Procedure A with 2.0 g (8.2 mmol) D-Proline benzyl ester hydrochloride and 640 mg (4.1 mmol) furan-2,5-dicarboxylic acid afforded, after flash chromatography (EtOAc), 1.7 g (78%) of the title compound as a yellow oil. MS m/e b) (R)-1-[5-[(R)-2-Carboxy-pyrrolidine-1-carbonyl]-furan-2-carbonyl]-pyrrolidine-2-carboxylic Acid Using General Procedure B with 1.7 g (3.2 mmol) (R)-1-[5-[(R)-2-benzyloxycarbonyl-pyrrolidine-1-carbonyl]-furan-2-carbonyl]-pyrrolidine-2-carboxylic acid benzyl ester afforded 1.02 g (91%) of the title compound as a white foam. MS m/e (%): 351 (M+H⁺, 100).

EXAMPLE 71

(S)-1-[6-[(S)-2-Carboxy-pyrrolidin-1-yl]-6-oxo-hexanoyl]-pyrrolidine-2-carboxylic Acid a) (S)-1-[6-[(S)-2-Benzyloxycarbonyl-pyrrolidin-1-yl]6-oxo-hexanoyl]-pyrrolidine-2-carboxylic Acid Benzyl Ester Using General Procedure A with 1.0 g (4.1 mmol) LProline benzyl ester hydrochloride and 300 mg (2.1 mmol) adipic acid afforded, after flash chromatography (EtOAc), 1.07 g (100%) of the title compound as a colorless oil. MS m/e (%): 521 (M+H⁺, 100).

b) (S)-1-[6-[(S)-2-Carboxy-pyrrolidin-1-yl]-6-oxo-hexanoyl]-pyrrolidine-2-carboxylic Acid Using General Procedure B with 1.07 g (2.1 mmol) (S)-1-[6-[(S)-2-benzyloxycarbonyl-pyrrolidin-1-yl]-6-oxo-hexanoyl]-pyrrolidine-2-carboxylic acid benzyl ester afforded 609 mg (87%) of the title compound as a white crystalline solid. MS m/e (%): 341 (M+H⁺, 100).

EXAMPLE 72

(S)-1-[[4-[2-[(S)-2-Carboxy-pyrrolidin-1-yl]-2-oxo-ethyl]-phenyl]-acetyl]-pyrrolidine-2-carboxylic Acid a) (S)-1-[[4-[2-[(S)-2-Benzyloxycarbonyl-pyrrolidin-1-yl]-2-oxo-ethyl]-phenyl]-acetyl]-pyrrolidine-2-Acid Benzyl Ester Using General Procedure A with 1.0 g (4.1 mmol) LProline benzyl ester hydrochloride and 400 mg (2.1 mmol) 1,4-phenylenediacet acid afforded, after flash chromatography (EtOAc), 1.07 g (91%) of the title compound as a colorless oil. MS m/e (%): 586 (M+NH₄⁺, 100), 569 (M+H⁺, 97).

b) (S)-1-[[4-[2-[(S)-2-Carboxy-pyrrolidin-1-yl]-2-oxo-ethyl]-phenyl]-acetyl]-pyrrolidine-2-carboxylic Acid Using General Procedure B with 1.07 g (1.88 mmol) (S)-1-[[4-[2-[(S)-2-benzyloxycarbonyl-pyrrolidin-1-yl]-2-oxo-ethyl]-phenyl]-acetyl]-pyrrolidine-2-carboxylic acid benzyl ester afforded 410 mg (56%) of the title compound as a white crystalline solid. MS m/e (%): 389 (M+H⁺, 100).

EXAMPLE 73

(S)-1-[[2-[2-[(S)-2-Carboxy-pyrrolidin-1-yl]-2-oxo-ethoxy]-phenoxy]-acetyl]-pyrrolidine-2-carboxylic Acid a) (S)-1-[[2-[2-[(S)-2-Benzyloxycarbonyl-pyrrolidin-1-yl]-2-oxo-ethoxy]-phenoxy]-acetyl]-pyrrolidine-2-carboxykic Acid Benzyl Ester Using General Procedure A with 1.0 g (4.1 mmol) LProline benzyl ester hydrochloride and 790 mg (2.1 mmol) 1,2-phenylenedioxyacetic acid afforded, after flash chromatography (EtOAc), 1.08 g (87%) of the title compound as a colorless oil. MS m/e (%): 601 (M+H⁺, 100).

b) (S)-1-[[2-[2-[(S)-2-Carboxy-pyrrolidin-1-yl]-2-oxo-ethoxy]-phenoxy]-acetyl]-pyrrolidine-2-carboxylic Acid Using General Procedure B with 1.08 g (1.8 mmol) (S)-1-[[2-[2-[(S)-2-Benzyloxycarbonyl-pyrrolidin-1-yl]-2-oxo-ethoxy]-phenoxy]-acetyl]-pyrrolidine2-carboxylic acid benzyl ester afforded 717 mg (95%) of the title compound as a white crystalline solid. MS m/e (%): 421 (M+H⁺, 100).

EXAMPLE 74

(R)-1-[[4-[2-[(R)-2-Carboxy-pyrrolidin-1-yl]-2-oxo-ethyl]-naphthalen-1-yl]-acetyl]-pyrrolidine-2-carboxylic Acid a) 2-Diazo-1-(4-diazoacetyl-naphthalen-1-yl)-ethanone To a stirred solution of 3.0 g (13.9 mmol) naphthalene-1,4-dicarboxylic acid and 4.4 ml (30.6 mmol) triethylamine in 200 ml THF at −15° C. was added dropwise 2.9 ml (30.6 mmol) ethyl chloroformate. After stirring for 15 min, 250 ml (approx. 0.3 M, approx. 75 mmol) of an ethereal solution of diazomethane was added at 0° C. and stirring continued for 16 h at room temperature. The reaction mixture was then washed sequentially with saturated sodium bicarbonate solution, saturated ammonium chloride solution and finally with saturated brine, and the aqueous phases back-extracted with ether. The combined organic extracts were dried over magnesium sulphate and concentrated in vacuo. Flash chromatography (gradient: 15–50% EtOAc/hexane) afforded 450 mg (12%) of the title compound as a yellow crystalline solid. MS m/e (%): 323 ([M+OAc]⁻, 100).

b) (4-Carboxymethyl-naphthalen-1-yl)-acetic acid

To a stirred solution of 450 mg (1.7 mmol) 2-diazo-1-(4-diazoacetylnaphthalen-1-yl)-ethanone in 20 ml THF at −20° C. were added sequentially in the dark 1.5 ml water, 86 mg (375 mmol) silver benzoate (0.22 equiv.) and 687 ml (4.9 mmol) triethylamine (2.9 equiv.) and stirring continued for 2 h at room temperature. The reaction mixture was then diluted with 100 ml ether and extracted twice with saturated sodium bicarbonate solution. The combined aqueous phases were extracted three times with ether, then acidified with concentrated hydochloric acid and extracted a further three times with ether. The latter organic extracts were combined and dried over sodium sulphate and concentrated in vacuo to afford 330 mg (80%) of the title compound as a yellow crystalline solid. MS m/e (%): 244 (M+, 100), 199 (M−CO₂H, 80).

c) (R)-1-[[4-[2-[(R)-2-Benzyloxycarbonyl-pyrrolidin-1-yl]-2-oxo-ethyllnaphthalen-1-yl]-acetyl]-pyrrolidine-2-carboxylic Acid Benzyl Ester Using General Procedure A with 200 mg (0.82 mmol) DProline benzyl ester hydrochloride and 100 mg (0.41 mmol) (4-carboxymethyl-naphthalen-1-yl)-acetic acid afforded, after flash chromatography (EtOAc), 188 mg (75%) of the title compound as a colorless oil. MS m/e (%): 636 (M+NH₄⁺, 100), 619 (M+H⁺, 75).

d) (R)-1-[[4-[2-[(R)-2-Carboxy-pyrrolidin-1-yl]-2-oxo-ethyl]-naphthalen-1-yl]acetyl]-pyrrolidine-2-carboxylic Acid Using General Procedure B with 130 mg (0.21 mmol) (R)-1-[[4-[2-[(R)-2-benzyloxycarbonyl-pyrrolidin-1-]-yl]-2-oxo-ethyl]-naphthalen-1-yl]-acetyl]-pyrrolidine-2-carboxylic acid benzyl ester afforded 79 mg (86%) of the title compound as a white crystalline solid. MS m/e (%): 437 ([M–H]$^-$, 100).

EXAMPLE 75

(R)-1-[[6-[2-[(R)-2-Carboxy-pyrrolidin-1-yl]-2-oxo-ethyl]-pyridin-2-yl]-acetyl]-pyrrolidine-2-carboxylic Acid a) (6-Cyanomethyl-pyridin-2-yl)-acetonitrile To a stirred solution of 3.47 g (13.1 mmol) 2,6-bis(bromomethyl)pyridine in 50 ml dichloromethane was added dropwise a solution of 4.1 g (26.2 mmol) tetraethylammonium cyanide in 20 ml dichloromethane and the reaction mixture then heated at 45° C. for 72 h. The reaction mixture was then cooled to room temperature and filtered. The filtrate was concentrated in vacuo, resuspended in ethyl acetate, filtered once again, and the second filtrate concentrated in vacuo. Flash chromatography (33% EtOAc/hexane) afforded 1.77 g (84%) of the title compound as a white crystalline solid. MS m/e (%): 157 (M$^+$, 100), 130 ([M–HCN]$^+$, 95), 90 (55).

b) (6-Carboxymethyl-pyridin-2-yl)-acetic Acid

A solution of 3.0 g (19.1 mmol) (6-cyanomethyl-pyridin-2-yl)-acetonitrile in 30 ml concentrated hydrochloric acid was heated at 100° C. for 24 h. The reaction mixture was then cooled to room temperature and concentrated in vacuo. The residue was redissolved in water, activated charcoal added, and the mixture heated at 50° C. for 30 min. After removal of the charcoal by filtration, the filtrate was concentrated in vacuo and the residue recrystallised from water at 4° C. to afford 2.48 g (100%) of the title compound as an off-white crystalline solid. $^1$H NMR d (250 MHz, D$_2$O) 8.42 (1H, t, J=8 Hz), 7.80 (2 H, d, J=8 Hz).

c) (R)-1-[[6-[2-[(R)-2-Benzyloxycarbonyl-pyrrolidin-1-yl]-2-oxo-ethyll-pyridin-2 yl]-acetyl]-pyrrolidine-2-carboxylic Acid Benzyl Ester Using General Procedure A with 9.7 g (40 mmol) DProline benzyl ester hydrochloride and 3.9 g (20 mmol) (6-carboxymethyl-pyridin-2-yl)-acetic acid afforded, after flash chromatography (gradient: 0–10% MeOH/EtOAc), 890 mg (8%) of the title compound as a yellow oil. MS m/e (%): 570 (M+H$^+$, 100).

d) (R)-1-[[6-(2-[(R)-2-Carboxy-pyrrolidin-1-yll-2-oxo-ethyl]-pyridin-2-yl]-acetyl]-pyrrolidine-2-carboxylic Acid Using General Procedure B with 890 mg (1.56 mmol) (R)-1-[[6-[2-[(R)-2-benzyloxycarbonyl-pyrrolidin-1-yl]-2-oxo-ethyl]-pyridin-2-yl]-acetyl]-pyrrolidine2-carboxylic acid benzyl ester afforded 410 mg (67%) of the title compound as a yellow crystalline solid. MS m/e (%): 390 (M+H$^+$, 100).

EXAMPLE 76

(R)-1-[[5-[2-[(R)-2-Carboxy-pyrrolidin-1-yl]-2-oxo-ethyl]-thiophen-2-yl]-acetyl]-pyrrolidine-2-carboxylic Acid a) 2,5-Bis-chloromethyl-thiophene To 63.4 ml of a 37% aqueous solution of formaldehyde was added dropwise with ice-cooling 15.3 of concentrated hydrochloric acid and then 20 ml (0.25 mol) thiophene was added dropwise and stirring continued for 90 min at room temperature. The reaction mixture was then extracted with ether and the organic phases washed sequentially with water, saturated sodium bicarbonate solution and finally with saturated brine. The aqueous phases were back-extracted with ether and the combined organic extracts were dried over sodium sulphate and concentrated in vacuo to afford 38.8 9 (86%) of the title compound RO-64-4463/000 as an amber-colored oil. MS m/e (%): 184 (M$^+$, 8), 182 (M$^+$, 15), 180 (M$^+$, 24), 147 ([M–Cl]$^+$, 44), 145 ([M–Cl]$^+$, 100), 110 (64).

b) (5-Cyanomethyl-thiophen-2-yl)-acetonitrile

To a stirred solution of 15 g (82.8 mmol) 2,5-bis-chloromethyl-thiophene in 500 ml dichloromethane was added dropwise a solution of 28.5 g (182 mmol) tetraethylammonium cyanide in 100 ml dichloromethane and the reaction mixture then heated at 45° C. for 24 h. The reaction mixture was then cooled to room temperature and washed twice with water. The organic phase was dried over sodium sulphate and concentrated in vacuo. Flash chromatography (20% EtOAc/hexane) afforded 4.88 g (36%) of the title compound as a yellow oil. MS mile (%): 162 (M$^+$, 44), 122 ([M–CH$_2$CN]$^+$, 100).

c) (5-Carboxymethyl-thiophen-2-yl)-acetic acid

To a stirred solution of 1.2 g (7.4 mmol) (5-cyanomethyl-thiophen-2-yl)-acetonitrile in 5 ml ethanol and 5 ml water was added 1.74 g (31.8 mmol) potassium hydroxide and the reaction mixture heated at 100° C. for 1 h. The reaction mixture was then cooled to room temperature and concentrated in vacuo. The residue was acidified with hydrochloric acid and extracted with three times with ether. The combined organic phases were dried over magnesium sulphate and concentrated in vacuo to afford 1.3 g (88%) of the title compound as a brown crystalline solid. MS m/e (%): 221 ([M+Na–H]$^-$, 50), 199 ([M–H]$^-$, 45), 155 ([M–CO$_2$H]$^-$, 100).

d) (R)-1-[[5-[2- (R)-2-tert-Butoxycarbonyl-pyrrolidin-1-yl]-2oxo-ethyl]-thiophen-2-yl]-acetyl]-pyrrolidine-2-carboxylic Acid tert-Butyl Ester Using General Procedure A with 2.23 g (13 mmol) DProline benzyl ester hydrochloride and 1 3 g (6.5 mmol) (5-carboxymethyl-thiophen-2-yl)-acetic acid afforded, after flash chromatography (gradient: 0–10% MeOH/EtOAc), 2.6 g (79%) of the title compound as a yellow oil. MS m/e (%): 524 (M+NH$_4^+$, 90), 507 (M+H$^+$, 10), 451 ([M+H–C$_4$H$_8$]$^+$, 30), 395 ([M+H-2C$_4$H$_8$]$^{30}$, 100).

e) (R)-1-[[5-[2-[(R)-2-Carboxy-pyrrolidin-1-yl]-2-oxo-ethyl]-thiophen-2-yl]acetyl]-pyrrolidine-2-carboxylic Acid Using General Procedure B with 600 mg (1.18 mmol) (R)-1-[[5-[2-[(R)-2-tert-Butoxycarbonyl-pyrrolidin-1-yl]-2-oxo-ethyl]-thiophen-2-yl]-acetyl]-pyrrolidine2-carboxylic acid tert-butyl ester afforded 100 mg (21%) of the title compound as a beige crystalline solid. MS m/e (%): 395 (M+H$^+$, 100).

EXAMPLE 77

(R)-1-[(2R,5S)-6-[(R)-2-Carboxy-pyrrolidin-1-yl]-2, 5-dimethoxy-6-oxo-hexanoyl]-pyrrolidine-2-carboxylic Acid a) (3 R,6 S)-3,6-Dimethoxy-cyclohexene Lit., *J. Org. Chem.*, 53:5695 (1988). To a stirred solution of 0.70 g (3.1 mmol) palladium acetate, 16.9 g (156 mmol) benzoquinone and 0.4 ml (6.2 mmol) methanesulphonic acid in 200 ml methanol at room temperature was added via syringe pump over 4 h a solution of 5.95 ml (62 mmol) 1,3-cyclohexadiene in 5 ml methanol, and stirring continued for an additional 16 h. The reaction mixture was extracted three times with ether and the combined organic extracts washed successively with water, 2 M sodium hydroxide solution and saturated brine. The organic phases were dried over sodium sulphate and concentrated in vacuo. Kugelrohr distillation (6 mbar, oven temp 120° C.) afforded 5.42 g (61%) of the title compound as a colorless oil. $^1$H NMR d (250 MHz, CDCl$_3$) 5.92 (2H, s), 3.70 (2H, t, J=5 Hz), 3.37 (6H, s), 1.90–1.65 (4H, m).

b) (2R,5S)-2,5-Dimethoxy-hexanedioic Acid

Lit., *J. Org. Chem.*, 53:5688 (1988). To a stirred solution of 5.0 g (35.2 mmol) (3R,6S)-3,6-dimethoxy-cyclohexene in 120 ml acetone and 120 ml water were added 37.6 g (176 mmol) sodium periodate and 50 mg (0.24 mmol) ruthenium (III) chloride and stirring contined for 16 h at room temperature. 5 ml isopropanol was added and stirring continued for 30 min, then the reaction mixture filtered and the filtrate concentrated in vacuo to half-volume. 5 g sodium bicarbonate was then added portionwise, and the mixture extracted three times with ethyl acetate. The combined organic phases were washed with saturated brine, dried over sodium sulphate, and concentrated in vacuo to afford 1.0 g (14%) of the title compound as an orange oil. MS m/e (%): 205 ([M–H]$^-$, 100).

c) (R)-1-[(2R,5S)-6-[(R)-2-benzyloxycarbonyl-pyrrolidin-1-yl]-2,5-dimethoxy-6 oxo-hexanoyl]-pyrrolidine-2-carboxylic Acid Benzyl Ester Using General Procedure A with 1.51 g (6.2 mmol) DProline benzyl ester hydrochloride and 643 mg (3.1 mmol) (2R,5S)-2,5-Dimethoxy-hexanedioic acid afforded, after flash chromatography (gradient: 10–100% EtOAc/hexane then 10% MeOH/EtOAc), 643 mg (36%) of the title compound as a yellow oil. MS m/e (%): 581 (M+H$^+$, 100).

d) (R)-1-[(2R,5S)-6-[(R)-2-Carboxy-pyrrolidin-1-yl]-2,5-dimethoxy-6-oxo-hexanoyl]-pyrrolidine-2-carboxylic Acid Using General Procedure B with 640 mg (1.10 mmol) (R)-1-[(2R,5S)-6-[(R)-2-benzyloxycarbonyl-pyrrolidine-1-yl]-2,5-dimethoxy-6-oxo-hexanoyl]-pyrrolidine-2-carboxylic acid benzyl ester afforded 440 mg (100%) of the title compound as a yellow solid. MS m/e (%): 399 [M–H]$^-$, 100).

EXAMPLE 78

(R)-1-[(2S,5S)- or -[(2R,5R)-6-[(R)-2-Hydroxymethyl-pyrrolidin-1-yl]-2,5-dimethoxy-6-oxo-hexanoyl]-pyrrolidine-2-carboxylic Acid a) Acetic acid (1RS,4RS)-4-acetoxy-cyclohex-2-enyl Ester Lit., *J. Org. Chem.*, 49:4619 (1984). To a stirred solution of 2.8 g (12.5 mmol) palladium acetate, 27.2 g (267 mmol) lithium acetate, and 7.64 g (70.7 mmol) benzoquinone in 200 ml acetic acid at room temperature were added 26.1 g (300 mmol) manganese dioxide and a solution of 23.8 ml (250 mmol) 1,-3-cyclohexadiene in 400 ml pentane, and stirring continued for 16 h. The twophase reaction mixture was separated and the acetic acid phase extracted twice with pentane. The combined organic extracts were washed successively with saturated brine, water, and 2 M sodium hydroxide solution, then the organic phases were dried over sodium sulphate and concentrated in vacuo. Recrystallisation from pentane afforded 16.1 g (33%) of the title compound as an off-white crystalline solid. MS m/e (%): 138 ([M–AcOH]$^+$, 8), 96 ([M–AcOH–COCH$_2$]$^+$, 100), 43 (40).

b) (1RS,4RS)-Cyclohex-2-ene-1,4-diol

Lit., *J. Org. Chem.*, 49:4619 (1984). To a stirred solution of 19.8 g (99.8 mmol) acetic acid (1RS,4RS)-4-acetoxy-cyclohex-2-enyl ester in 500 ml methanol was added 120 ml 2 M sodium hydroxide solution and the reaction mixture refluxed for 15 min. After cooling to room temperature, the reaction mixture was concentrated in vacuo to 100 ml, and then saturated with sodium hydroxide pellets. The mixture was extracted repeatedly with ethyl acetate and the combined organic phases dried over sodium sulphate and concentrated in vacuo to afford 10.2 g (90%) of the title compound as an off-white crystalline solid. MS m/e (%): 113 ([M–H]$^+$, 13), 96 ([M–H$_2$O]$^+$, 36), 70 ([M–H$_2$C=CHOH]$^+$, 100).

c) (3RS,6RS)-3,6-Dimethoxy-cyclohexene

Lit., *J. Org. Chem.*, 53:5695 (1988). To 14.3 g (328 mmol) sodium hydride (55% dispersion in oil) was added dropwise at 0° C. with stirring a solution of 10.1 g (88.5 mmol) (1RS,4RS)-cyclohex-2-ene-1,4-diol in 100 ml THF. 34 ml (546 mmol) methyl iodide was then added and stirring continued for an additional 48 h at room temperature. The reaction was quenched with saturated ammonium chloride solution and extracted with ether. The combined organic extracts were washed successively with saturated ammonium chloride solution and saturated brine, dried over sodium sulphate, and concentrated in vacuo to afford 11.5 g (91%) of the title compound as a yellow oil. $^1$H NMR d (250 MHz, CDCl$_3$) 5.90 (2H, s), 3.82 (2H, br t), 3.37 (6H, s), 2.10 (2H, m), 1.51 (2H, m).

d) (2RS,5RS)-2,5-Dimethoxy-hexanedioic acid

To a stirred solution of 6.0 g (42.2 mmol) (3 RS,6 RS)-3,6-dimethoxycyclohexene in 140 ml acetone and 140 ml water were added 50.5 g (236 mmol) sodium periodate and 67 mg (0.32 mmol) ruthenium (III) chloride and stirring contined for 16 h at room temperature. 10 ml isopropanol was added and stirring continued for 30 min, then the reaction mixture filtered and the filtrate concentrated in vacuo to half-volume. 5 g sodium bicarbonate was then added portionwise, and the mixture extracted three times with ether. The aqueous phase was acidified with 25% hydrochloric acid and extracted repeatedly with ethyl acetate. The combined organic phases were dried over sodium sulphate, and concentrated in vacuo to afford 1.32 g (15%) of the title compound RO-64-5650/000 as an orange oil. Continuous extraction of the aqueous phase over 48 h afforded another 608 mg (7%) of product. MS m/e (%): 161 ([M–CO$_2$H]$^+$, 20), 113 (58),. 101 (69), 85 (50), 71 (100).

e) (R)-1-[(2S,5S)- or -2R,5R)-6-[(R)-2-Benzyloxymethyl-pyrrolidin-1-yl]-2,5-dimethoxy-6-oxo-hexanoyl]-pyrrolidine-2-carboxylic Acid Benzyl and (R)-1-[(2R,5R)- or -[(2S,5S)-6-[(R)-2-Benzyloxymethyl-pyrrolidin-1-yl]-2,5-dimethoxy-6-oxo-haxanoyl]-pyrrolidine-2-carboxylic Acid Benzyl Using General Procedure A with 1.67 g (6.9 mmol) DProline benzyl ester hydrochloride and 250 mg (1.2 mmol) (2RS,5RS)-2,5-dimethoxy-hexanedioic acid afforded, after flash chromatography (gradient: 50–100% EtOAc/hexane then 10% MeOH/EtOAc), 95 mg (13%) of the title compound (mixture of 2 diastereomers) as a brown oil, and 172 mg (24%) of the title compound (single separated diastereomer) as a yellow oil. MS m/e (%): 581 (M+H$^+$, 100).

f) (R)-1-[(2S,5S)- or -[(2R,5R)-6-[(R)-2-Hydroxymethyl-pyrrolidin-1-yl]-2,5-dimethoxy-6-haxanoyl]-pyrrolidine-2-carboxylic Acid Using General Procedure B with 160 mg (0.28 mmol) (R)-1-[(2R,5R)- or [(2S, 5S)-6-[(R)-2-benzyloxymethyl-pyrrolidin-1-yl]-2,5-dimethoxy-6-oxo-hexanoyl]-pyrrolidine-2-carboxylic acid benzyl afforded 90 mg (82%) of the title compound as a white foam. MS m/e (%): 399 ([M–H]$^-$, 100), 355 ([M–H–CO$_2$]$^-$, 61).

EXAMPLE 79

(R)-1-[(2R,5R)- or -[(2S,5S)-6-[(R)-2-Hydroxymethyl-pyrrolidin-1-yl]-2,5-dimethoxy-6-oxo-hexanoyl]-pyrrolidine-2-carboxylic Acid Using General Procedure B with 95 mg (0.28 mmol) (R)-1-[(2S,5S)- or -[(2R,5R)-6-[(R)-2-benzyloxymethylpyrrolidin-1-yl]-2,5-dimethoxy-6-oxo-hexanoyl]-pyrrolidine-2-carbnoxylic acid benzyl afforded 70 mg (100%) of the title compound as a white foam. MS m/e (%): 399 ([M–H]⁻, 100), 355 ([M–H–CO₂]⁻, 20).

EXAMPLE 80

(R)-1-[2,5-Dibenzyl-6-[(R)-2-carboxy-pyrrolidin-1-yl]-6-oxo-hexanoyl]-pyrrolidine-2-carboxylic Acid (Mixture of 3 Diastereomers)

a) Mixture of (E)-(2R,5S)- and -(2RS,5SR)-2,5-dibenzyl-hex-3-enedioic acid diethyl ester To a stirred solution of 688 mg (3.44 mmol) trans-2-butene-1,4-dicarboxylic acid diethyl ester in 35 ml THF was added 1.46 g (34.4 mmol) anhydrous lithium chloride and the resulting suspension cooled to –78° C. 3.44 ml (6.88 mmol) of a 2 M solution of LDA in THF was added dropwise and stirring continued for 45 min. 0.82 ml (6.9 mmol) benzyl bromide was then added and stirring continued for 1 h at –78° C. and 10 min at 0° C. The reaction was quenched at this temperature by addition of saturated ammonium chloride solution and the mixture extracted three times with ether. The combined organic phases were washed with saturated brine, dried over sodium sulphate, and concentrated in vacuo. Flash chromatography (5% EtOAc in hexane) afforded 927 mg (71%) of the title compound as a yellow oil. MS m/e (%): 398 ([M+NH₄]⁺, 100).

b) Mixture of (E)-(2R,5S)- and -(2RS,5SR)-2,5-dibenzyl-hex-3-enedioic

To a stirred solution of 200 mg (0.53 mmol) mixture of (E)-(2R,5S)- and -(2RS,5SR)-2,5-dibenzyl-hex-3-enedioic acid diethyl ester in 5 ml THF was added 4.3 ml (4.3 mmol) of 1 M sodium hydroxide solution. After stirring for 68 h at room temperature, the reaction mixture was acidified to pH 3 by addition of 1 M hydrochloric acid and extracted three times with ethyl acetate. The combined organic phases were washed successively with water and with saturated brine, dried over sodium sulphate, and concentrated in vacuo. Flash chromatography (50% EtOAc in hexane containing 1% AcOH) afforded 127 mg (74%) of the title compound as a white crystalline solid. MS m/e (%): 342 ([M+NH₄]⁺, 100):

c) (E)-(R)-1-[2,5-Dibenzyl-6-[(R)-2-benzyloxycarbonyl-pyrrolidin-1-yl]-6-oxo-hex-3-enoyl]-pyrrolidine-2-carboxylic Acid Benzyl Ester (Mixture of 3 diastereomers)

Using General Procedure A with 1.04 g (4.30 mmol) DProline benzyl ester hydrochloride and 700 mg (2.16 mmol) mixture of (E)-(2R,5S)- and -(2RS,5SR)-2,5-dibenzyl-hex-3-enedioic acid diethyl ester afforded, after flash chromatography (5% MeOH in EtOAc), 926 mg (61%) of the title compound as a yellow oil. MS m/e (%): 716 (M+NH₄⁺, 100), 699 (M+H⁺, 85).

d) (R)-1-[2,5-Dibenzyl-6-[(R)-2-carboxy-pyrrolidin-1-yl]-6-oxo-hexanoyl]-pyrrolidine-2-carboxylic Acid (Mixture of 3 Diastereomers)

Using General Procedure B with 926 mg (1.33 mmol) (E)-(R)-1-[2,5-dibenzyl6-[(R)-2-benzyloxycarbonyl-pyrrolidine-1-yl]-6-oxo-hex-3-enoyl]-pyrrolidine-2-carboxylic acid benzyl ester (mixture of 3 diastereomers) afforded 610 mg (89%) of the title compound as a white crystalline solid. MS m/e (%): 519 ([MH–H]⁻, 100).

EXAMPLE 81

(R)-1-[2,5-Dibutyl-6-[(R)-2-carboxy-pyrrolidin-1-yl]-6-oxo-hexanoyl]-pyrrolidine-2-carboxylic Acid (1 Out of 3 Possible Diastereomers)

a) Mixture of (E)-(2R,5S)- and -(2RS,5SR)-2,5-dibutyl-hex-3-enedioic acid diethyl ester To a stirred solution of 2.0 g (9.99 mmol) trans-2-butene-1,4-dicarboxylic acid diethyl ester in 80 ml THF was added 2.54 g (59.9 mmol) anhydrous lithium chloride and the resulting suspension cooled to –78° C. 10.0 ml (20.0 mmol) of a 2 M solution of LDA in THF was added dropwise and stirring continued for 45 min. 2.2 ml (20.4 mmol) butyl bromide was then added and stirring continued for 15 min at –78° C., then 30 min at 0° C., and then 4 h at room temperature. The reaction was quenched by addition of saturated ammonium chloride solution and the mixture extracted three times with ether. The combined organic phases were washed successively with saturated ammonium chloridewution, water, and saturated brine, dried over sodium sulphate, and concentrated in vacuo. Successive flash chromatography (10% EtOAc in hexane for first column; then gradient: 10–100% toluene in cyclohexane for second column) afforded 509 mg (16%) of the title compound as a yellow oil. MS m/e (%): 330 ([M+NH₄]⁺, 100).

b) Mixture of (E)-(2R,5S)- and -(2RS,5SR)-2,5-dibutyl-hex-3-enedioic Acid

To a stirred solution of 435 mg (1.39 mmol) mixture of (E)-(2R,5S)- and -(2RS,5SR)-2,5-dibutyl-hex-3-enedioic acid diethyl ester in 10 ml THF was added 26 ml (26 mmol) of 1 M sodium hydroxide solution. After stirring for 72 h at room temperature, the reaction mixture was acidified to pH 3 by addition of 1 M hydrochloric acid and extracted three times with ethyl acetate. The combined organic phases were washed successively with water and with saturated brine, dried over sodium sulphate, and concentrated in vacuo to afford 346 mg (97%) of the title compound as a white crystalline solid. MS m/e (%): 255 ([M–H]⁻, 60), 211 ([M–H–CO₂]⁻, 100).

c) (E)-(R)-1-[2,5-Dibutyl-6-[(R)-2-benzyloxycarbonyl-pyrrolidin-1-yl]-6-oxo-hex-3-enoyl]-pyrrolidin-2-carboxylic Acid Benzyl Ester (Mixture of 2 out of 3 Possible Diastereomers) and (E)-(R)-1-[2,5-Dibutyl-6-[(R)-2-benzyloxycarbonyl-pyrrolidin-1-yl]-6-oxo-hex-3-enoyl]-pyrrolidine-2-carboxylic Acid Benzyl Ester (Principally 1 Out of 3 Possible Diastereomers)

Using General Procedure A with 653 mg (2.70 mmol) DProline benzyl ester hydrochloride and 346 mg (1.35 mmol) mixture of (E)-(2R,5S)- and -(2RS,5SR)-2,5-dibutyl-hex-3-enedioic acid afforded, after flash chromatography (gradient: 33–50% EtOAc in hexane), 148 mg (17%) of the title compound RO-64-3271/000 (mixture of 2 diastereomers) as a yellow oil and 116 mg (14%) of the title compound (single diastereomer) as a yellow oil. MS m/e (%): 648 (M+NH₄⁺, 90), 631 (M+H⁺, 100).

d) (R)-1-[2,5-Dibuty [(R)-2-carboxy-pyrrolidin-1-yl]-6-oxtexanoyl]-pyrrolidine-2-carboxylic Acid (1 Out of 3 Possible Diastereomers)

Using General Procedure B with 140 mg (0.22 mmol) (E)-(R)-1-[2,5-dibutyl-6[(R)-2-benzyloxycarbonyl-pyrrolidine-1-yl]-6-oxo-hex-3-enoyl]-pyrrolidine-2-carboxylic acid benzyl ester (principally 1 out of 3 possible diastereomers) afforded 81 mg (81%) of the title compound RO-64-3273/000 (single diastereomer) as a colorless oil. MS m/e (%): 451 ([M–H]⁻, 100).

EXAMPLE 82

(R)-1-[2,5-Dibutyl-6-[(R)-2-carboxy-pyrrolidin-1-yl]-6-oxo-hexanoyl]-pyrrolidine2-carboxylic Acid (Mixture of 2 Out of 3 Possible Diastereomers)

Using General Procedure B with 110 mg (0.22 mmol) (E)-(R)-1-[2,5-dibutyl-6[(R)-2-benzyloxycarbonyl-pyrrolidine-1-yl]-6-oxo-hex-3-enoyl]-pyrrolidine-2-carboxylic acid benzyl ester (mixture of 2 out of 3 possible diastereomers) afforded 69 mg (88%) of the title compound (2 diastereomers) as a colorless oil. MS m/e (%): 451 ([M−H]−, 100).

EXAMPLE 83

(R)-1-[2,5-Diisopropyl-6-[(R)-2-carboxy-pyrrolidin-1-yl]-6-oxo-hexanoyl]-pyrrolidine-2-carboxylic Acid (Mixture of 3 Diastereomers)

a) Mixture of (E)-(2R,5S)- and -(2RS,5SR)-2,5-diisopropyl-hex-3-enedioic Acid Diethyl Ester To a stirred solution of 5.0 g (25.0 mmol) trans-2-butene-1,4-dicarboxylic acid diethyl ester in 120 ml THf was added 6.35 g (150 mmol) anhydrous lithium chloride and the resulting suspension cooled to −78° C. 25.0 ml (50.0 mmol) of a 2 M solution of LDA in THF was added dropwise and stirring continued for 45 min. 4.7 ml (50 mmol) isopropyl bromide was then added and stirring continued for 15 min at −78° C., then 4 h at 0° C., and then 48 h at room temperature. The reaction was quenched by addition of saturated ammonium chloride solution and the mixture extracted three times with ether. The combined organic es were washed successively with saturated ammonium chloride solution, water, and saturated brine, dried over sodium sulphate, and conc en trated in vacuo. Successive flash chromatography (20% EtOAc in hexane for first column; 5% EtOAc in hexane for second column; 10% EtOAc in hexane for third column) afforded 259 mg (4%) of the title compound as a yellow oil. MS m/e (%): 302 ([M+NH$_4$]+, 100 ).

b) Mixture of (E)-(2R, 5S)- and -(2RS,5SR)-2,5-diisopropyl-hex-3-enedioic

To a stirred solution of 108 mg (0.38 mmol) mixture of (E)-(2R,5S)- and -(2RS,5SR)-2,5-diisopropyl-hex-3-enedioic acid diethyl ester in 5 ml THF was added 10 ml (10 mmol) of 1 M sodium hydroxide solution. After stirring for 96 h at room temperature, the reaction mixture was acidified to pH 3 by addition of 1 M hydrochloric acid and extracted three times with ethyl acetate. The combined organic phases were washed successively with water and with saturated brine, dried over sodium sulphate, and concentrated in vacuo to afford 70 mg (81%) of the title compound as a yellow oil. MS mie (%:227 ([M−H]−, 100).

c) (E)-(R)-1-(2, 5-Diisopropyl-6-[(R)-2-benzyloxycarbonyl-pyrrolidin-1yl]-6-oxo-hex-3-enoyl]-pyrrolidine-2-carboxylic Acid Benzyl Ester (Mixture of the 3 Diastereomers)

Using General Procedure A with 114 mg (0.47 mmol) DProline benzyl ester hydrochloride and 54 mg (0.24 mmol) mixture of (E)-(2R,5S)- and -(2RS, 5SR)-2,5-diisopropyl-hex-3-enedioic afforded, after flash chromatography (gradient: 33–50% EtOAc in hexane), 15 mg (11%) of the title compound as a colorless oil. MS mle (%): 620 (M+NH$_4$+, 100).

d) (R)-1-[2,5-Diisopropyl-6-[(R)-2-carboxy-pyrrolidin-1-yl]-6-oxo-hexanoyl]-pyrrolidine-2-carboxy Acid (Mixture of 3 Diastereomers)

Using General Procedure B with 41 mg (0.07 mmol) (E)-(R)-1-[2,5-diisopropyl-6-[(R)-2-benzylcarbonyl-pyrrolidin-1-yl]-6-oxo-hex-3-enoyl]pyrrolidine-2-carboxylic acid benzyl ester (mixture of the 3 diastereomers) afforded 28 mg (10 of the title compound as a colorless oil. MS m/e (%):423 ([M−H]−, 100).

EXAMPLE 84

(R)-1-[5-[(R)-2-Carboxy-pyrrolidine-1-carbonyl]-7-methoxy-2-(2-methoxyethyl)-heptanoyl]-pyrrolidine-2-carboxylic Acid (Mixture of 3 Diastereomers a) Mixture of (E)-(2R,5S)- and -(2RS,5SR)-2,5-bis-(2-methoxy-ethyl)-hex-3 enedioic Acid Diethyl Ester To a stirred solution of 5.0 g (25.0 mmol) trans-2-butene-1,4-dicarboxylic acid diethyl ester in 125 ml THF was added 6.35 g (150 mmol) anhydrous lithium chloride and the resulting suspension cooled to −78° C. 25.0 ml (50.0 mmol) of a 2 M solution of LDA in THF was added dropwise and stirring continued for 45 min. 7.4 ml (78.7 mmol) 2-methoxyethyl bromide was then added and stirring continued for 15 min at −78° C., then 1 h at 0° C., and then 2 h at room temperature. The reaction was quenched by addition of saturated ammonium chloride solution and the mixture extracted three times with ether. The combined organic phases were washed successively with saturated ammonium chloride solution, water, and saturated brine, dried over sodium sulphate, and concentrated in vacuo. Flash chromatography (50% toluene in EtOAc) afforded 1.29 g (16%) of the title compound as a yellow oil. MS m/e (%): 334 ([M+NH$_4$]+, 100).

b) Mixture of (E)-(2R,5S)- and -(2RS,5SR)-2,5-bis-(2-methoxy-ethyl)-hex-3-Enedioic Acid To a stirred solution of 1.29 g (4.08 mmol) mixture of (E)-(2R,5S)- and -(2RS,5SR)-2,5-bis-(2-methoxy-ethyl)-hex-3-acid diethyl ester in 10 ml THF was added 33 ml (33 mmol) of 1 M sodium hydroxide solution. After stirring for 18 h at room temperature, the reaction mixture was acidified to pH 3 by addition of 1 M hydrochloric acid and extracted three times with ethyl acetate. The combined organic phases were washed successively with water and with saturated brine, dried over sodium sulphate, and concentrated in vacuo to afford 894 (84%) of the title compound as a yow oil. MS m/e (%): 259 ([M−H]−, 100).

c) (E)-(R)-1-[5-[(R)-2-Benzyloxycarbonyl-pyrrolidine-1-carbonyl]-7-methoxy-2-(2-methoxy-ethyl)-heptanoyl]-pyrrolidine-2-carboxylic Acid Benzyl Ester (Mixture of 3 Diastereomers)

Using General Procedure A with 1.86 g (7.69 mmol) DProline benzyl ester hydrochloride and 894 mg (3.84 mmol) mixture of (E)-(2R,5S)- and -(2RS,5SR)-2,5-bis-(2-methoxy-ethyl)-hex-3-enedioic acid afforded, after successive flash chromatography (gradient 50%–100% EtOAc in hexane then 10% MeOH in EtOAc for first column; 20% toluene in EtOAc for second column; 20% toluene in EtOAc for third column; gradient: 25–20% toluene in EtOAc for fourth column), 146 mg (7%) of the title compound as a light yellow oil. MS m/e (%): 652 (M+NH$_4$+, 50), 635 (M+H+, 100).

d) (R)-1-[5-[(R)-2-Carboxy-pyrrolidine-1-carbonyl]-7-methoxy-2-(2-methoxyethyl)-heptanoyl]-pyrrolidine-2-crboxylic Acid (Mixture of 3 Diastereomers Using General Procedure B with 146 mg (0.23 mmol) (E)-(R)-1-[5-[(R)-2 benzyloxycarbonyl-pyrrolidine-1-carbonyl]-7-methoxy-2-(2-methoxy-ethyl)-heptanoyl]-pyrrolidine-2-carboxylic acid benzyl ester (mixture of 3 diastereomers) afforded 92 mg (88%) of the title compound as a colorless oil. MS m/e (%): 455 ([M−H]−, 100).

EXAMPLE 85

(R)-1-[2-[4-[2-[(R)-2-Carboxy-pyrrolidin-1-yl]-1-methyl-2-oxo-ethyl]-phenyl]-propionyl]-pyrrolidine-2-carboxylic Acid (Mixture of the 3 Diastereomers)

a) (4-Benzyloxycarbonylmethyl-phenyl)-acetic Acid Benzyl Ester

To a suspension of 10.0 g (51.5 mmol) benzene-1,4-diacetic acid, 0.94 g (7.73 mmol) 4-dimethylaminopyridine and 5.33 ml (51.5 mmol) benzyl alcohol in 150 ml dichloromethane at 0° C. was added 11.85 g (61.8 mmol) N-(3-dimethylaminopropyl)-N'-ethylcarbodiimide and stirring continued at 0° C. for 2 h and then at room temperature for 16 h. The reaction mixture was then washed sequentially with 1 M hydrochloric acid, saturated sodium bicarbonate solution and finally with saturated brine, and the aqueous phases back-extracted with dichloromethane. The combined organic extracts were dried over sodium sulphate and concentrated in vacuo. Flash chromatography (50% EtOAc in hexane) then afforded the title compound as a light yellow oil which crystallised on standing. MS m/e (%): 374 ($M^+$, 10), 283 ($[M-Bn]^+$, 16), 239 ($[M-Bn-CO_2]^+$, 18), 91 ($Bn^+$, 100).

b) Mixture of (R)-2-[4-[(S)- and (RS)-2-[4-[(RS)-1-benzyloxycarbonyl-ethyl]-phenyl]-propionic Acid Benzyl Ester To a stirred solution of 2.0 g (5.3 mmol) (4-benzyloxycarbonylmethyl-phenyl)-acetic acid benzyl ester in 80 ml THF was added 1.35 g (32 mmol) anhydrous lithium chloride and the resulting suspension cooled to −78° C. 10.7 ml (21.4 mmol) of a 2 M solution of LDA in THF was added dropwise and stirring continued for 45 min. 1.33 ml (21.3 mmol) methyl iodide was then added and stirring continued for. 15 min at −78° C., then 20 min at 0° C. The reaction was quenched at this temperature by addition of saturated ammonium chloride solution and the mixture extracted three times with ether. The combined organic phases were dried over sodium sulphate, and concentrated in vacuo. Flash chromatography (EtOAc) afforded 2.1 g (100%) of the title compound as a brown oil. MS m/e (%): 420 ($[M+NH_4]^+$, 100).

c) Mixture of (R)-2-[4-[(S)- and (RS)-2-[4-[(RS)-1-carboxy-ethyl)-phenyl]propionic Acid A solution of 230 mg (0.57 mmol) mixture of (R)-2-[4-[(S)- and (RS)-2-[4[(RS)-1-benzylcarbonly-ethyl]-phenyl]-propionic acid benzyl ester in 20 ml ethanol was stirred with 5 wt % of 10% palladium on charcoal under 1 atm of hydrogen for 16 h at room temperature. After filtration to remove the catalyst, the reaction mixture was concentrated in vacuo to afford 70 mg (55%) of the title compound as a white crystalline solid. MS m/e (%): 222 ($M^+$, 23), 177 ($[M-CO_2H]^-$, 100), 131.

d) (R)-1-[2-[4-[2-[(R)-2-Benzyloxycarbonyl-pyrrolidin-1-yl]-1-methyl-2-oxoethyl]-phenyl]-propionyl]-pyrrolidine-2-carboxylic Acid Benzyl Ester (Mixture of the 3 Diastereomers)

Using General Procedure A with 370 mg (1.53 mmol) DProline benzyl ester hydrochloride and 170 mg (0.77 mmol) mixture of (R)-2-[4-[(S)- and (RS)-2-[4-[(RS)-1-carboxy-ethyl)-phenyl]-propionic acid afforded, after flash chromatography (EtOAc), 170 mg (38%) of the title compound as a colorless oil. MS m/e (%): 614 ($M+NH_4^+$, 100), 597 ($M+H^+$, 60).

e) (R)-1-[2-[4-[2-[(R)-2-Carboxy-pyrrolidin-1-yl]-1-methyl-2-oxo-ethyl]-phenyl]-propionyl]-pyrrolidine-2-carboxylic Acid (Mixture of the 3 Diastereomers)

Using General Procedure B with 170 mg (0.29 mmol) (R)-1-[2-[4-[2-[(R)-2-benzyloxycarbonyl-pyrrolidin-1-yl]-1-methyl-2-oxo-ethyl]-phenyl]-propionyl]-pyrrolidine-2-carboxylic acid benzyl ester (mixture of the 3 diastereomers) afforded 50 mg (42%) of the title compound as a white foam. MS m/e (%): 415 ($[M-H]^-$, 100)

EXAMPLE 86

(2 E,4E)-(R)-1-[6-[(R)-2-Carboxy-pyrrolidin-1-yl]-2,5-dimethyl-6-oxo-hexa-2,4-dienoly]-pyrrolidine-2-carboxylic Acid a) (2E,4E)-(R)-1-[6-[(R)-2-Benzyloxycarbonyl-pyrrolidin-1-yl]-2,5-dimethyl-6-oxo-hexa-2,4-dienoyl]-pyrrolidine-2-carboxylic Acid Benzyl Ester To a stirred suspension of 0.91 g (5.32 mmol) 2,5-dimethyl-hex-2,4-dien-1,6-dioic acid in 80 ml dichloromethane containing two drops of pyridine was added dropwise at room temperature 0.77 ml (10.6 mmol) thionyl chloride and the reaction mixture was then heated at 50° C. for 2 h. The resulting solution was cooled to 0° C. and added dropwise to a solution of 2.57 g (10.6 mmol) D-Proline benzyl ester hydrochloride and 3.0 ml (21.5 mmol) triethylamine in 50 ml dichloromethane at 0° C. Stirring was continued for 2 h at 0° C. and then 24 h at room temperate The reaction mixture was then washed sequentially with 1 M hydrochloric acid and with water, and the aqueous phases back-extracted with dichloromethane. The combined organic extracts were dried over sodium sulphate and concentrated in vacuo. Flash chromatography (EtOAc) afforded 2.79 g (96%) of the title compound as a colorless oil. MS mie (%): 562 ($M+NH_4^+$, 100), 545 ($M+H^+$, 5).

b) (2E,4E)-(R)-1-[6-[(R)-2-Carboxy-pyrrolidin-1-yl]-2,5-dimethyl-6-oxo-hexa-2,4-dienoyl]-pyrrolidine-2-carboxylic Acid Using General Procedure B with 1.14 9 (2.09 mmol) (2 E,4 E)-(R)-1-[6-[(R)-2-Benzyloxycarbonyl-pyrrolidin-1-yl]-2,5-dimethyl-6-oxo-hexa-2,4-dienoyl]-pyrrolidine-2-carboxylic acid benzyl ester and with dioxane as solvent afforded 127 mg (16%) of the title compound as a white solid. MS mie (%): 365 ($M+H^+$, 100).

EXAMPLE 87

(R)-1-[6-[(R)-2-Carboxy-pyrrolidin-1-yl)-2,5-dimethyl-6-oxo-hexanoyl]-pyrrolidine-2-carboxylic Acid (Mixture of 3 Diastereomers)

A solution of 593 mg (1.09 mmol) (2E,4E)-(R)-1-[6-[(R)-2-benzyloxycarbonyl-pyrrolidin-1-yl]-2,5-dimethyl-6-oxo-hexa-2,4-dienoyl]-pyrrolidine-2-carboxylic acid benzyl ester in 15 ml dioxane was stirred with 25 mg (0.11 mmol) platinum (IV) oxide under 1 atm of hydrogen for 72 h at room temperature. After filtration to remove the catalyst, the reaction mixture was concentrated in vacuo and azeotroped three times with chloroform on a rotary evaporator to remove last traces of dioxane, then triturated in ether to afford 400 mg (100%) of the title compound as a white foam. MS m/e (%): 369 ($M+H^+$, 100).

EXAMPLE 88

Mixture of (R)-1-[(3R,4R)- and -[(3S,4S)-3,4-dihydroxy-6-[(R)-2-carboxy-pyrrolidin-1-yl]-6-oxo-hexanoyl]-pyrrolidine-2-carboxylic Acid a) (R)-1-[6-[(R)-2-Benzyloxycarbonyl-pyrrolidine-1-carbonyl]-pyridine-2-carbonyl]-pyrrolidine-2-carboxylic Acid Benzyl Ester Using General Procedure A with 5.0 g (20.6 mmol) DProline benzyl ester hydrochloride and 1.5 g (10.3 mmol)

trans-3-hexenedioic acid afforded, after flash chromatography (EtOAc), 3.15 g (59%) of the title compound as a light yellow oil. MS m/e (%): 536 (M+NH$_4^+$, 100), 519 (M+H$^+$, 80).

b) Mixture of (R)-1-[(3R,4R)- and -[(3 S,4 S)-6-[(R)-2-Benzyloxycarbonyl-pyrrolidin-1-yl]-3,4-dihydroxy-6-oxo-hexanoyl]-pyrrolidine-2-carboxylic Acid Benzyl Ester To a stirred solution of 3.13 g (6.04 mmol) (R)-1-[6-[(R)-2-benzyloxycarbonyl-pyrrolidine-1-carbonyl]-pyridine-2-carbonyl]-pyrrolidine-2-carboxylic acid benzyl ester in 10 ml acetone and 10 ml water were added 980 mg (7.25 mmol) 4-methylmorpholine-4-oxide and 0.6 ml of a 2.5% solution of osmium tetroxide in tert-butanol and stirring continued for 72 h at room temperature. 50 ml of 38% sodium hydrogensulphite solution was then added at 0° C. and stirring continued for a further 15 min. The reaction mixture was then filtered and extracted three times with ethyl acetate. The combined organic extracts were washed sequentially with 1 M hydrochloric acid and saturated brine, dried over sodium sulphate, and concentrated in vacuo to afford 3.34 g (100%) of the title compound as a colorless oil. MS m/e (%): 575 (M+Na$^+$, 35), 570 (M+NH$_4^+$, 55), 553 (M+H$^+$, 100).

c) Mixture of (R)-1-(3R,4R)- and -[(3S,4S)-3,4-dihydroxy-6-[(R)-2-carboxy-pyrrolidin-1-yl]-6-oxo-hexanoyl]-pyrrolidine-2-carboxylic Acid Using General Procedure B with 506 mg (0.92 mmol) mixture of (R)-1[(3R,4R)-1-[(3R,4R)-and -[(3S,4S)-6-[(R)-2-benzyloxycarbonyl-pyrrolidin-1-yl]-3,4-dihydroxy-6-oxo-hexanoyl]-pyrrolidine-2-carboxylic acid benzyl ester afforded 341 mg (100%) of the title compound as a white solid. MS m/e (%): 395 (M+NH$_4^+$, 55), 373 (M+H$^+$, 100).

EXAMPLE 89

(E)-(R)-1-[6-[(R)-2-Carboxy-pyrrolidin-1-yl]-6-oxo-hex-3-enoyl]-pyrrolidine-2-carboxylic Acid a) (E)-(R)-1-[6-[(R)-2-tert-Butoxycarbonyl-pyrrolidin-1-yl)-6-oxo-hex-3-enoyl]-pyrrolidine-2-carboxylic Acid tert-Butyl Ester Using General Procedure A with 1.5 g (8.76 mmol) DProline tert-butyl ester and 630 mg (4.37 mmol) trans-3-hexenedioic acid afforded, after flash chromatography (10% EtOH in EtOAc), 1.59 g (77%) of the title compound as a white crystalline solid. MS m/e (%): 568 (M+NH$_4^+$, 35), 451 (M+H$^+$, 100), 395 ([M+H–C$_3$H$_8$]$^+$, 32), 339 ([M+H–2C$_3$H$_8$]$^+$, 40).

b) (E)-(R)-1-[6-[(R)-2-Carboxy-pyrrolidin-1-yl)-6-oxo-hex-3-enoyl]-pyrrolidine2-carboxylic Acid To a stirred solution of 600 mg (1.33 mmol) (E)-(R)-1-[6-[(R)-2-tert-butoxycarbonyl-pyrrolidin-1-yl)-6-oxo-hex-3-enoyl]-pyrrolidine-2-carboxylic acid tert-butyl ester in 15 ml dichloromethane at 0° C. was added dropwise 4.4 ml (57.8 mmol) trifluoroacetic acid and stirring continued for 16 h at room temperature. Concentration in vacuo and azeotroping three times with chloroform on a rotary evaporator afforded 402 mg (90%) of the title compound as a white foam. MS m/e (%): 339 (M+H$^+$, 100).

EXAMPLE 90

(R)-1-[3-[[3-[(R)-2-Carboxy-pyrrolidin-1-yl]-3-oxo-propyl]-propyl-amino]-propionyl]-pyrrolidine-2-carboxylic Acid a) (R)-1-Acryloyl-pyrrolidine-2-carboxylic Acid Benzyl Ester To a stirred solution of 390 mg (1.6 mmol) DProline benzyl ester hydrochloride and 0.47 ml (3.4 mmol) triethylamine in 20 ml dichloromethane at 0° C. was added dropwise 0.2 ml (2.4 mmol) acryloyl chloride and stirring continued for 24 h at room temperature. The reaction mixture was then washed sequentially with water, 1 M hydrochloric acid and once more with water, and the aqueous phases back-extracted with dichloromethane. The combined organic e acts were dried over sodium sulpha nd concentrated in vacuo to afford 420 mg (100%) of the title compound as a colorless oil. MS m/e (%): 259 (M$^+$, 25), 124 (100), 91 (25), 70 (21).

b) (R)-1-[3-[[3-[(R)-2-Benzyloxycarbonyl-pyrrolidin-1-yl]-3-oxo-propyl]-propyl-amino]-propionyl]-pyrrolidine-2-carboxylic Acid Benzyl Ester A solution of 400 mg (1.5 mmol) (R)-1-acryloyl-pyrrolidine-2-carboxylic acid benzyl ester and 63 ml (0.75 mmol) propylamine in 5 ml acetonitrile was stirred for 16 h at room temperature, then for 6 h at 45° C., and finally for 16 h at 80° C. Concentration in vacuo and flash chromatography (20% H$_2$O in acetone) afforded 84 mg (19%) of the title compound as a pale yellow oil. MS m/e (%): 578 (M+H$^+$, 100).

c) (R)-1-[3-[[3-[(R)-2-Carboxy-pyrrolidin-1-yl]-3-oxo-propyl]-propyl-amino]-propionyl]-pyrrolidine-2-carboxylic Acid A solution of 84 mg (0.15 mmol) (R)-1-[3-[[3-[(R)-2-benzyloxycarbonyl-pyrrolidin-1-yl]-3-oxo-propyl]-propyl-amino]-propionyl]-pyrrolidine-2-carboxylic acid benzyl ester in 3 ml ethanol was stirred with 10 mg 10% palladium on charcoal under I atm of hydrogen for 16 h at room temperature. After filtration to remove the catalyst, concentration in vacuo afforded 58 mg (100%) of the title compound as a white solid. MS m/e (%): 398 (M+H$^+$, 100).

EXAMPLE 91

(R)-1-[3-[[3-[(R)-2-Carboxy-pyrrolidin-1-yl]-3-oxo-propyl]-cyclopropylmethyl-amino]-propionyl]-pyrrolidine-2-carboxylic Acid a) (R)-1-[3-[[3-[(R)-2-Benzyloxycarbonyl-pyrrolidin-1-yl]-3-oxo-propyl]cyclopropylmethyl-amino]-propionyl]-pyrrolidine-2-carboxylic Acid Benzyl Ester A solution of 444 mg (1.71 mmol) (R)-1-acryloyl-pyrrolidine-2-carboxylic acid benzyl ester and 74 ml (0.85 mmol) cyclopropylmethylamine in 5 ml acetonitrile was stirred for 1 h at room temperature, then for 16 h at 80° C. Concentration in vacuo and flash chromatography (gradient: 0–100% MeOH in EtOAc) afforded 220 mg (44%) of the title compound as a yellow oil. MS m/e (%): 590 (M+H$^+$, 100).

b) (R)-1-[3-[[3-[(R)-2-Carboxy-pyrrolidin-1-yl]-3-oxo-propyl]-cyclopropylmethyl-aminol]-propionyl]-pyrrolidine-2-carboxylic Acid A solution of 220 mg (0.37 mmol) (R)-1-[3-[[3-[(R)-2-benzyloxycarbonyl-pyrrolidin-1-yl]-3-oxo-propyl]-cyclopropylmethyl-amino]-propionyl]-pyrrolidine2-carboxylic acid benzyl ester in 20 ml isopropanol was stirred with 10 mg 10% palladium on charcoal under 1 atm of hydrogen for 16 h at room temperature. After filtration to remove the catalyst, concentration in vacuo afforded 153 mg (100%) of the title compound as a yellow solid. MS m/e (%): 408 ([M–H]$^-$, 100).

EXAMPLE 92

(R)-1-[3-[(3,4-Dimethoxy-benzyl)-[3-[(R)-2-carboxy-pyrrolidin-1-yl]-3-oxo-propyl]-amino]-propionyl]-pyrrolidine-2-carboxylic acid trifluoroacetate (1:1)

a) (R)-1-Acryloyl-pyrrolidine-2-carboxylic acid tert-Butyl Ester

To a stirred solution of 5.0 g (29.2 mmol) DProline tert-butyl ester and 4.5 ml (32.1 mmol) triethylamine in 180 ml dichloromethane at 0° C. was added dropwise 3.6 ml (43.8 mmol) acryloyl chloride and stirring continued for 48 h at room temperature. The reaction mixture was then washed sequentially with water, saturated ammonium chloride solution, once more with water and then with saturated brine, and the aqueous phases back-extracted with dichloromethane. The combined organic extracts were dried over sodium sulphate and concentrated in vacuo to afford 6.6 g (100%) of the title compound as a yellow oil. MS m/e (%): 243 (M+NH$_4^+$, 33), 226 (M+H$^+$, 100).

b) (R)-1-[3-[[3-[(R)-2-tert-Butoxycarbonyl-pyrrolidin-1-yl]-3-oxo-propyl]-(3,4-dimethoxy-benzyl)-amino]-propionyl]-pyrrolidine-2-carboxylic Acid tert-Butyl Ester A solution of 1.0 g (4.44 mmol) (R)-1-acryloyl-pyrrolidine-2-carboxylic acid tert-butyl ester and 0.33 ml (2.22 mmol) veratrylamine in 25 ml acetonitrile was stirred for 16 h at 80° C. Concentration in vacuo and flash chromatography (gradient: 0–10% MeOH in EtOAc) afforded 150 mg (10%) of the title compound as a light brown oil. MS m/e (%): 618 (M+H$^+$, 100).

c) (R)-1-[3-[(3,4-Dimethoxy-benzyl)-[3-[(R)-2-carboxy-pyrrolidin-1-yl]-3-oxo-propyl]-amino]-propionyl]-pyrrolidine-2-carboxylic Acid Trifluoroacetate (1:1)

To a stirred solution of 150 mg (0.24 mmol) (R)-1-[3-[[3-[(R)-2-tert-butoxycarbonyl-pyrrolidin-1-yl]-3-oxo-propyl]-(3,4-dimethoxy-benzyl)-amino]propionyl]-pyrrolidine-2-carboxylic acid tert-butyl ester in 5 ml dichloromethane at 0° C. was added dropwise 1.0 ml trifluoroacetic acid and stirring continued for 16 h at room temperature. Concentration in vacuo and azeotroping three times with chloroform on a rotary evaporator afforded, after trituration in ether, 130 mg (87%) of the title compound as a yellow crystalline solid. MS m/e (%): 506 (M+H$^+$, 100).

EXAMPLE 93

(R)-1-[3-[[3-[(R)-2-Carboxy-pyrrolidin-1-yl]-3-oxo-propyl]-(2-methoxy-ethyl)-amino]-propionyl]-pyrrolidine-2-carboxylic Acid Trifluoroacetate (1:1)

a) (R)-1-[3-[[3-[(R)-2-tert-Butoxycarbonyl-pyrrolidin-1-yl]-3-oxo-propyl]-(2-methoxy-ethyl)-amino]-propionyl]-pyrrolidine-2-carboxylic Acid tert-Butyl Ester A solution of 1.0 g (4.44 mmol) (R)-1-acryloyl-pyrrolidine-2-carboxylic acid tert-butyl ester and 0.19 ml (2.22 mmol) 2-methoxyethylamine in 25 ml acetonitrile was stirred for 16 h at 80° C. Concentration in vacuo and flash chromatography (gradient: 0–10% MeOH in EtOAc) afforded 300 mg (23%) of the title compound as a light brown oil. MS m/e (%): 526 (M+H$^+$, 100).

b) (R)-1-[3-[[3-[(R)-2-Carboxy-pyrrolidin-1-yl]-3-oxo-propyl]-(2-methoxy-ethyl)-amino]-propionyl]-pyrrolidine-2-carboxylic Acid Trifluoroacetate (1:1)

To a stirred solution of 150 mg (0.29 mmol) (R)-1-[3-[[3-[(R)-2-tert-butoxycarbonyl-pyrrolidin-1-yl]-3-oxo-propyl]-(2-methoxy-ethyl)-amino]-propionyl]-pyrrolidine-2-carboxylic acid tert-butyl ester in 5 ml dichloromethane at 0° C. was added dropwise 1.0 ml trifluoroacetic acid and stirring continued for 16 h at room temperature. Concentration in vacuo and azeotroping three times with chloroform on a rotary evaporator afforded, after resuspension in water and subsequent lyophilisation, 100 mg (67%) of the title compound as a yellow oil. MS m/e (%): 436 (M+Na$^+$, 35), 414 (M+H$^+$, 100).

EXAMPLE 94

(R)-1-[3-[Benzyl-[3-[(R)-2-carboxy-pyrrolidin-1-yl]-3-oxo-propyl]-amino]-propionyl]-pyrrolidine-2-carboxylic Acid Trifluoroacetate (1:1)

a) (R)-1-[3-[Benzyl-[3-[(R)-2-tert-butoxycarbonyl-pyrrolidin-1-yl]-3-oxo-propyl]-amino]-propionyl]-pyrrolidine-2-carboxylic Acid tert-Butyl Ester A solution of 1.0 g (4.44 mmol) (R)-1-acryloyl-pyrrolidine-2-carboxylic acid tert-butyl ester and 0.24 ml (2.22 mmol) benzylamine in 25 ml acetonitrile was stirred for 16 h at 80° C. Concentration in vacuo and flash chromatography (gradient: 0–10% MeOH in EtOAc) afforded 470 mg (34%) of the title compound as a yellow oil. MS m/e (%): 558 (M+H$^+$, 100).

b) (R)-1-[3-[Benzyl-[3-[(R)-2-carboxy-pyrrolidin-1-yl]-3-oxo-propyl]-amino]-propionyl]-pyrrolidine-2-carboxylic Acid Trifluoroacetate (1:1)

To a stirred solution of 200 mg (0.36 mmol) (R)-1-[3-[benzyl-[3-[(R)-2-tert-butoxycarbonyl-pyrrolidin-1-yl]-3-oxo-propyl]-amino]-propionyl]-pyrrolidine-2-carboxylic acid tert-butyl ester in 5 ml dichloromethane at 0° C. was added dropwise 1.0 ml trifluoroacetic acid and stirring continued for 16 h at room temperature. Concentration in vacuo and azeotroping three times with chloroform on a rotary evaporator afforded, after trituration in ether, 160 mg (80%) of the title compound as a yellow crystalline solid. MS m/e (%): 468 (M+Na$^+$, 30), 446 (M+H$^+$, 100).

EXAMPLE 95

(R)-1-[3-[3-[(R)-2-Carboxy-pyrrolidin-1-yl]-3-oxo-propylamino]-propionyl]-pyrrolidine-2-carboxylic Acid Trifluoroacetate (1:1)

a) (R)-1-[3-[[3-[(R)-2-tert-Butoxycarbonyl-pyrrolidin-1-yl]-3-oxo-propyl]-(4-trifluoromethyl-benzyl)-amino]-propionyl]-pyrrolidine-2-carboxylic Acid tert-Butyl Ester A solution of 1.0 g (4.44 mmol) (R)-1-acryloyl-pyrrolidine-2-carboxylic acid tert-butyl ester and 0.32 ml (2.22 mmol) para-trifluoromethylbenzylamine in 25 ml acetonitrile was stirred for 16 h at 80° C. Concentration in vacuo and flash chromatography (gradient: 0–10% MeOH in EtOAc) afforded 480 mg (31%) of the title compound as a light brown oil. MS m/e (%): 626 (M+H$^+$, 100). ps b) (R)-1-[3-[3-[(R)-2-tert-Butoxycarbonyl-pyrrolidin-1-yl]-3-oxo-propylamino]-propionyl]-pyrrolidine-2-carboxylic Acid tert-Butyl Ester and (R)-1-[3-[[3-[(R)-2-tert-Butoxycarbonyl-pyrrolidin-1-yl]-3-oxo-propyl]-ethyl-amino]-propionyl]-pyrrolidine-2-carboxylic Acid tert-Butyl Ester A solution of 290 mg (0.46 mmol) (R)-1-[3-[[3-[(R)-2-tert-butoxycarbonyl-pyrrolidin-1-yl]-3-oxo-propyl]-(4-trifluoromethyl-benzyl)-amino]-propionyl]-pyrrolidine-2-carboxylic acid tert-butyl ester in 50 ml ethanol was stirred with 30 mg 10% palladium on charcoal under 1 atm of hydrogen for 72 h at room temperature. After filtration to remove the catalyst, concentration in vacuo and flash chromatography (gradient: 0–100% MeOH in EtOAc containing 1% Et$_3$N) afforded 36 mg (17%) of the title compound (R)-1-[3-[3-[(R)-2-tert-Butoxycarbonyl-pyrrolidin-1-yl]-3-oxo-propylamino]-propionyl]-pyrrolidine-2-carboxylic acid tert-butyl ester as a yellow oil. MS m/e (%): 468 (M+H$^+$, 100). Further flash chromatography of the less polar fractions (gradient: 0–20% MeOH in EtOAc containing 1% Et$_3$N) afforded 87 mg (38%) of the by-product (R)-1-[3-[[3-[(R)-2-tert-butoxycarbonyl-pyrrolidin-1-yl]-3-oxo-propyl]-ethyl-amino]-propionyl]-pyrrolidine-2-carboxylic acid tert-butyl ester as a yellow oil. MS m/e (%): 496 (M+H$^+$, 100).

c) (R)-1-[3-[3-[(R)-2-Carboxy-pyrrolidin-1-yl]-3-oxo-propylamino]-propionyl]-pyrrolidine-2-carboxylic Acid Trifluoroacetate (1:1)

To a stirred solution of 33 mg (0.07 mmol) (R)-1-[3-[3-[(R)-2-tert-butoxycarbonyl-pyrrolidin-1-yl]-3-oxo-propylamino]-propionyl]-pyrrolidine-2-carboxylic acid tert-butyl ester in 5 ml dichloromethane at 0° C. was added dropwise 1.0 ml trifluoroacetic acid and stirring continued for 16 h at room temperature. Concentration in vacuo and azeotroping three times with chloroform on a rotary evaporator afforded, after resuspension in water and subsequent lyophilization, 19 mg (76%) of the title compound as a yellow glassy solid. MS m/e (%): 354 ([M–H]$^-$, 100).

EXAMPLE 96

(R)-1-[3-[Ethyl-[3-[(R)-2-carboxy-pyrrolidin-1-yl]-3-oxo-propyl]-amino]-propionyl]-pyrrolidine-2-carboxylic Acid Trifluoroacetate (1:1)

To a stirred solution of 85 mg (0.17 mmol) (R)-1-[3-[[3-[(R)-2-tert-butoxycarbonyl-pyrrolidin-1-yl]-3-oxo-propyl]-ethyl-amino]-propionyl]-pyrrolidine-2-carboxylic acid tert-butyl ester in 5 ml dichloromethane at 0° C. was added dropwise 1.0 ml trifluoroacetic acid and stirring continued for 16 h at room temperature. Concentration in vacuo and azeotroping three times with chloroform on a rotary evaporator afforded, after resuspension in water and lyophilization, 63 mg (97%) of the title compound as a yellow crystalline solid. MS m/e (%): 442 ([M+OAc]$^-$, 35), 382 ([M–H]$^-$, 100).

EXAMPLE 97

(R)-1-[3-[[3-[(R)-2-Carboxy-pyrrolidin-1-yl]-3-oxo-propyl]-(4-trifluoromethylbenzyl)-amino]-propionyl]-pyrrolidine-2-carboxylic Acid Trifluoroacetate (1:1)

To a stirred solution of 200 mg (0.32 mmol) (R)-1-[3-[[3-[(R)-2-tertbutoxycarbonyl-pyrrolidin-1-yl]-3-oxo-propyl]-(4-trifluoromethylbenzyl)-amino]-propionyl]-pyrrolidine-2-carboxylic acid tert-butyl ester in 5 ml dichloromethane at 0° C. was added dropwise 1.0 ml trifluoroacetic acid and stirring continued for 16 h at room temperature. Concentration in vacuo and azeotroping three times with chloroform on a rotary evaporator afforded, after trituration in ether, 150 mg (75%) of the title compound as a yellow crystalline solid. MS m/e (%): 536 (M+Na$^+$, 20), 514 (M+H$^+$, 100).

EXAMPLE 98

Mixture of (R)-1-[6-[(S)- and (RS)-1-[6-[(RS)-2-Carboxy-pyrrolidin-1-yl]-6-oxo-hexanoyl]-pyrrolidine-2-carboxylic Acid a) 1H-Pyrrole-2-carboxylic Acid Benzyl Ester Lit. J. Org. Chem., 44:975 (1979). To a stirred solution of 5.0 g (45.0 mmol) pyrrole-2-carboxylic acid and 31.3 ml (225 mmol) triethylamine in 100 ml DMF was added dropwise 26 ml (225 mmol) benzyl bromide and stirring continued for 72 h at room temperature. The reaction mixture was then concentrated in vacuo and the residue resuspended in dichloromethane and washed twice with saturated sodium bicarbonate solution and twice with water, and the aqueous phases back-extracted with dichloromethane. The combined organic extracts were dried over sodium sulphate and concentrated in vacuo. Flash chromatography (25% EtOAc in hexane) afforded 8.23 g (90%) of the title compound as a yellow oil. MS m/e (%): 201 (M$^+$, 33), 94 ([M–OBn]$^+$, 22), 91 (Bn$^+$, 100).

b) 1-[6-(2-Benzyloxycarbonyl-pyrrol-1-yl)-6-oxo-hexanoyl]-1H-pyrrole-2-carboxylic Acid Benzyl Ester To a stirred solution of 1.0 g (4.97 mmol) 1H-pyrrole-2-carboxylic acid benzyl ester, 0.06 g (0.50 mmol) 4-dimethylaminopyridine and 0.82 ml (5.47 mmol) 1,8-diazabicyclo[5.4.0]undec-7-ene in 40 ml dichloromethane at 0° C. was added dropwise 0.36 ml (2.49 mmol) adipoyl chloride and stirring continued for 1 h at room temperature. The reaction mixture was then washed sequentially with 1 M hydrochloric acid, saturated sodium bicarbonate solution and finally with saturated brine, and the aqueous phases back-extracted with dichloromethane. The combined organic extracts were dried over sodium sulphate and concentrated in vacuo. Flash chromatography (25% EtOAc in hexane) afforded 450 mg (35%) of the title compound as a white crystalline solid. MS m/e (%): 530 (M+NH$_4^+$, 100).

c) Mixture of (R)-1-[6-[(S)- and (RS)-1-[6-[(RS)-2-carboxy-pyrrolidin-1-yl]-6-oxo-hexanoyl]-pyrrolidine-2-carboxylic Acid Using General Procedure B with 800 mg (1.56 mmol) 1-[6-(2-benzyloxycarbonyl-pyrrol-1-yl)-6-oxo-hexanoyl]-1H-pyrrole-2-carboxylic acid benzyl ester afforded 470 mg (91%) of the title compound as a white crystalline solid. MS m/e (%): 339 ([M–H]$^-$, 100).

EXAMPLE 99

1-[6-(2-Carboxy-pyrrol-1-yl)-6-oxo-hexanoyl]-1H-pyrrole-2-carboxylic Acid a) 1H-Pyrrole-2-carboxylic Acid tert-Butyl Ester Lit. Tetrahedron, 41:5633 (1985). To a stirred solution of 10.0 g (90.0 mmol) pyrrole-2-carboxylic acid in 180 ml dioxane was added dropwise at 0° C. 18 ml concentrated sulphuric acid 2-methylpropene was then condensed into the reaction flask over the course of 1 h, using a dry-ice condenser, and stirring continued for 16 h at 0° C. while the dry-ice condenser was periodically refilled so as to maintain a slow reflux of 2-methylpropene. The reaction mixture was then poured cautiously into an ice-cooled mixture of 400 ml ether and 150 ml 2 M sodium hydroxide solution. The phases were separated and the aqueous phase extracted twice more with ether. The combined organic phases were washed successively with 2 M sodium hydroxide solution, water and finally with saturated brine, then dried over sodium sulphate and concentrated in vacuo to afford 9.07 g (60%) of the title compound as a colorless oil which still contained some dioxane. $^1$H NMR d (250 MHz, CDCl$_3$) 9.60 (1H, br s), 6.90 (1H, m), 6.83 (1H, m), 6.22 (1H, m), 1.56 (9H, s).

b) 1-[6-(2-tert-Butoxycarbonyl-pyrrol-1-yl)-6-oxo-hexanoyl]-1H-pyrrole-2-carboxylic Acid tert-Butyl Ester To a stirred solution of 1.3 g (7.77 mmol) 1H-pyrrole-2-carboxylic acid tert-butyl ester, 95 mg (0.78 mmol) 4-dimethylaminopyridine and 1.28 ml (8.56 mmol) 1,8-diazabicyclo[5.4.0]undec-7-ene in 40 ml dichloromethane at 0° C. was added dropwise 0.57 ml (3.91 mmol) adipoyl chloride and stirring continued for 16 h at room temperature. A further 95 mg (0.78 mmol) 4-dimethylaminopyridine and 1.28 ml (8.56 mmol) 1,8-diazabicyclo[5.4.0]undec-7-were added and stirring continued for a further 4 h at room temperature. The reaction mixture was then washed sequentially with 1 M hydrochloric acid, saturated sodium bicarbonate solution and finally with saturated brine, and the aqueous phases back-extracted with dichloromethane. The combined organic extracts were dried over sodium sulphate and concentrated in vacuo. Flash chromatography (gradient: 10–20% EtOAc in hexane) afforded 464 mg (13%) of the title compound as a light yellow crystalline solid. MS m/e (%): 462 (M+NH$_4^+$, 100).

c) 1-[6-(2-Carboxy-pyrrol-1-yl)-6-oxo-hexanoyl]-1H-pyrrole-2-carboxylic Acid

To a stirred solution of 55 mg (0.12 mmol) 1-[6-(2-tert-butoxycarbonyl-pyrrol-1-yl)-6-oxo-hexanoyl]-1H-pyrrole-2-carboxylic acid tert-butyl ester in 8 ml dichloromethane at 0° C. was added dropwise 0.15 ml (1.97 mmol) trifluoroacetic acid and stirring continued for 16 h at room temperature. Concentration in vacuo and azeotroping three times with chloroform on a rotary evaporator afforded 39 mg (95%) of the title compound as an off-white crystalline solid. MS m/e (%): 350 (M+NH$_4^+$, 100).

EXAMPLE 100

(R)-1-[6-[(R)-2-Carboxy-4,4-difluoro-pyrrolidin-1-yl]-6-oxo-hexanoyl]-4,4-difluoropyrrolidine-2-carboxylic Acid a) (2R)-4-Oxo-pyrrolidine-1,2-dicarboxylic Acid 2-Benzyl Ester 1-tert-Butyl Ester A solution of 15.6 ml (0.22 mol) dimethylsulfoxide in 50 ml dichloromethane was given to 9.60 ml oxalylchloride in 150 ml dichloromethane at minus 65° C. during a period of 10 minutes. After 5 minutes at −65° C. 32.1 g (0.1 mol) (2R,2R)-4-hydroxy-pyrrolidine-1,2-dicarboxylic acid 2-benzyl ester 1-tert-butyl ester in 100 ml dichloromethane were added and after additional 15 minutes 24.4 ml (0.18 mol) triethylamine. The cooling bath was removed, stirring was continued over night, and then the mixture was poured into ice-water. Extraction with dichloromethane, followed by washing with 0.05 N HCl, bicarbonate and water and chromatography over silicagel with dichloromethane/ethylacetate 98:2 gave 11.1 g (35%) (2R)-4-oxo-pyrrolidine-1,2-dicarboxylic acid 2-benzyl ester 1-tert-butyl ester as a colorless liquid. MS m/e (%): 263(M-isobutylene, 7), 219 (8), 184 (24), 128 (14), 91 (58), 84 (40), 57 (100); $[\alpha]_D$=+1.1° (c=1% in methanol).

b) (2R)-4,4-Difluoro-pyrrolidine-1,2-dicarboxylic Acid 2-Benzyl Ester 1-tert-Butyl Ester A solution of 0.64 g (0.002 mol) (2R)-4-oxo-pyrrolidine-1,2-dicarboxylic acid 2-benzyl ester 1-tert-butyl ester in 3 ml dichloromethane was treated at 0° C. with 0.79 ml (0.006 mol) diethylaminosulfur trifluoride, stirring was continued at room temperature for 32 hours and then the mixture was poured on ice. Extraction with dichloromethane and filtration over silicagel with hexane followed by elution with dichloromethane gave 0.62 g (90%) (2R)-4,4-difluoropyrrolidine-1,2-dicarboxylic acid 2-benzyl ester 1-tert-butyl ester as light yellow oil.

MS m/e (%): 285(1), 206 (6), 106 (33), 91 (35), 57 (100); $[\alpha]_D$=+43.0° (c=1% in methanol).

c) (2R)-4,4-Difluoro-pyrrolidine-2-carboxylic Acid Benzyl Ester Hydrochloride (1:1)

100 ml of dry HCl in diethylether was added to a solution of 7.51 g (0.022 mol) (2R)-4,4-difluoro-pyrrolidine-1,2-dicarboxylic acid 2-benzyl ester 1-tert-butyl ester in a mixture 100 ml diethylether and 20 ml dichloromethane. After stirring for two days 5.84 g (96%) (2R)-4,4-difluoro-pyrrolidine-2-carboxylic acid benzyl ester hydrochloride (1:1) were isolated by filtration and dried under reduced pressure. Mp.: 118–120° C.; $[\alpha]_D$=+29.3° (c=1% in methanol).

d) (R)-1-[6-[(R)-2-Benzyloxycarbonyl-4,4-difluoro-pyrrolidin-1-yl]-6-oxo-hexanoyl]-4,4-difluoropyrrolidine-2-carboxylic Acid Benzyl Ester To a suspension of 1.11 g (0.004 mol) (2R)-4,4-difluoropyrrolidine-2-carboxylic acid benzyl ester hydrochloride (1:1) in 20 ml dichloromethane were added 1.17 ml (0.008 mol) triethylamine, and 0.29 ml (0.002 mol) adipoyidichloride in 5 ml dichloromethane. After stirring at room temperature over night the mixture was extracted with 1N HCl, water and aqueous sodiumbicarbonate and dried with sodiumsulfate. Chromatogaphy over silicagel with dichloromethane/ethylacetate 8:2 gave 0.79 g (66%) (R)-1-[6-[(R)-2-benzyloxycarbonyl-4,4-difluoro-pyrrolidin-1-yl]-6-oxo-hexanoyl]-4,4-difluoropyrrolidine-2-carboxylic acid benzyl ester as colorless oil. ISP-MS: 593 (MH)$^+$; $[\alpha]_D$=+67.3° (c=1% in methanol).

e) (R)-1-[6-[(R)-2-Carboxy-4,4-difluoro-pyrrolidin-1-yl]-6-oxo-hexanoyl]-4,4-difluoropyrrolidine-2-carboxylic Acid 0.59 g (0.001 mol) (R)-1-[6-[(R)-2-Benzyloxycarbonyl-4,4-difluoro-pyrrolidin-1-yl]-6-oxo-hexanoyl]-4,4-difluoropyrrolidine-2-carboxylic acid benzyl ester in 20 ml ethanol were hydrogenated at room temperature and atmospheric pressure in the presence of 0.12 g 5% palladium/carbon. After completion of the reaction the catalyst was filtered off, the solvent was distilled off, and the residue was dissolved in dichloromethane. Evaporation gave 0.4 g (97%) (R)-1-[6-[(R)-2-carboxy-4,4-difluoro-pyrrolidin-1-yl]-6-oxo-hexanoyl]-4,4-difluoropyrrolidine-2-carboxylic acid as a white foam. ISP-MS: 413 (MH)$^+$; $[\alpha]_D$=+54.2° (c=1% in dimethylsulfoxide).

EXAMPLE 101

(R)-1-[[2-[2-[(R)-2-Carboxy-4,4-difluoropyrrolidin-1-yl]-2-oxo-ethoxyl]-phenoxy]acetyl]-4,4-difluoropyrrolidine-2-carboxylic Acid a) (R)-1-[[2-[2-[(R)-2-Benzyloxycarbonyl-4,4-difluoropyrrolidin-1-yl]-2-oxo-ethoxyl]-phenoxy]acetyl]-4,4-difluoropyrrolidine-2-carboxylic Acid Benzyl Ester To a mixture of 1.11 g (0.004 mol) (2R)-4,4-difluoropyrrolidine-2-carboxylic acid benzyl ester hydrochloride (1:1), 0.45 g (0.002 mol) 1,2-phenylenedioxydiacetic acid, 1.21 g (0.012 mol) N-methylmorpholine, and 0.61 g (0.004 mol) 1-hydroxybenzotriazole hydrate in 90 ml dichloromethane were added 0.77 g (0.004 mol) 1-(3-dimethylaminopropyl)-3-ethylcarbodiimid hydrochloride. After stirring at room temperature for 18 hours the mixture was extracted with 1N HCl, water, 10% aqueous sodium bicarbonate and again water. Chromatography over silicagel with dichloromethane/ethylacetate 9:1 yielded 0.52 g (39%) (R)-1-[[2-[2-[(R)-2-benzyloxycarbonyl-4,4-difluoropyrrolidin-1-yl]-2-oxo-ethoxyl]-phenoxy]acetyl]4,4-difluoropyrrolidine-2-carboxylic acid benzyl ester as colorless oil. ISP-MS: 673 (MH)$^+$; $[\alpha]_D$=+68.4° (c=1% in methanol).

b) (R)-1-[[2-[2-[(R)-2-Carboxy-4,4-difluoropyrrolidin-1-yl]-2-oxo-ethoxyl]-phenoxy]acetyl]-4,4-difluoropyrrolidine-2-carboxylic Acid 0.47 g (0.0007 mol) (R)-1-[[2-[2-[(R)-2-Benzyloxycarbonyl-4,4-difluoropyrrolidin-1-yl]-2-oxo-ethoxyl]-phenoxy]acetyl]-4,4-difluoropyrrolidine-2-carboxylic acid benzyl ester in 20 ml ethanol were hydrogenated at room temperature and atmospheric pressure in the presence of 0.09 g 5% palladium/carbon. After completion of the reaction the catalyst was filtered off, the solvent was distilled off, and the residue was dissolved in dichloromethane. Evaporation gave 0.32 g (94%) (R)-1-[[2-[2-[(R)-2-carboxy-4,4-difluoropyrrolidin-1-yl]-2-oxoethoxyl]-phenoxy]acetyl]-4,4-difluoropyrrolidine-2-carboxylic acid as a light yellow foam. ISP-MS: 493 (MH)$^+$; $[\alpha]_D$=+46.8° (c=1% in dimethylsulfoxide).

EXAMPLE 102

(R)-1-[[4-[2-[(R)-2-Carboxy-4,4-difluoropyrrolidin-1-yl]-2-oxo-ethyl]-phenyl]-acetyl]-4,4-difluoropyrrolidine-2-carboxylic Acid a) (R)-1-[[4-[2-[(R)-2-Benzyloxycarbonyl-4,4-difluoropyrrolidin-1-yl]-2-oxo-ethyl]-phenyl]-acetyl]-4,4-difluoropyrrolidine-2-carboxylic Acid Benzyl Ester To a mixture of 1.11 g (0.004 mol) (2R)-4,4-difluoropyrrolidine-2-carboxylic acid benzyl ester hydrochloride (1:1), 0.39 g (0.002 mol) 1,4-phenylenediacetic acid, 1.21 g (0.012 mol) N-methylmorpholine, and 0.61 g (0.004 mol) 1-hydroxybenzotriazole hydrate in 90 ml dichloromethane were added 0.77 g (0.004 mol) 1-(3-dimethylaminopropyl)-3-ethylcarbodiimid hydrochloride. After stirring at room temperature for 18 hours the mixture was extracted with 1N HCl, water, 10% aqueous sodium bicarbonate and again water. Chromatography over silicagel with dichloromethane/ethylacetate 9:1 yielded 0.72 g (56%) (R)-1-[[4-[2-[(R)-2-benzyloxycarbonyl-4,4-difluoropyrrolidin-1-yl]-2-oxo-ethyl]-phenyl]-acetyl]-4,4-difluoropyrrolidine-2-carboxylic acid benzyl ester as colorless oil. ISP-MS: 658 (MNH$_4$)$^+$; $[\alpha]_D$=+55.5° (c=1% in methanol).

b) (R)-1-[[4-[2-[(R)-2-Carboxy-4,4-difluoropyrrolidin-1-yl]-2-oxo-ethyl]-phenyl]-acetyl]-4,4-difluoropyrrolidine-2-carboxylic Acid 0.64 g (0.001 mol) (R)-1-[[4-[2-[(R)-2-Benzyloxycarbonyl-4,4-difluoropyrrolidin-yl]-2-oxo-ethyl]-phenyl]-acetyl]-4,4-difluoropyrrolidine-2-carboxlic acid benzyl ester in 20 ml ethanol were hydrogenated at room temperature and atmospheric pressure in the presence of 0.13 g 5% palladium/carbon. After completion of the reaction the catalyst was filtered off, the solvent was distilled off, and the residue was dissolved in dichloromethane. Evaporation gave 0.28 g (61%) (R)-1-[[4-[2-[(R)-2-carboxy-4,4-difluoropyrrolidin-1-yl]-2-oxo-ethyl]-phenyl]-acetyl]-4,4-difluoropyrrolidine-2-carboxylic acid as a light yellow foam. ISP-MS: 478 (MNH$_4$)$^+$; $[\alpha]_D$=+50.3° (c=0.33% in dimethylsulfoxide).

EXAMPLE 103

(R)-1-[6-[(R)-2-Carboxy-2,5-dihydropyrrole-1-yl]-6-oxo-hexanoyl]-2,5-dihydropyrrole-2-carboxylic Acid a) (2R,4R)-4-(Toluene-4-sulfonyloxy)-pyrrolidine-1,2-dicarboxylic Acid 2-Benzyl Ester 1-tert-Butyl Ester A solution of 2.35 g (0.007 mol) (2R,2R)-4-hydroxypyrrolidine-1,2-dicarboxylic acid 2-benzyl-ester 1-tert-butyl ester in 22 ml pyridine were treated at 5° C. with 1.53 g (0.008 mol) p-toluenesulfonyl chloride and kept in the refrigerator for 15 days. The pyridine was then distilled off in vacuo and the residue was purified by chromatography on silicagel with dichloromethane/ethylacetate 95:5 to yield 2.81 g (81%) (2R,4R)-4-(toluene-4-sulfonyloxy)-pyrrolidine-1,2-dicarboxylic acid 2-benzyl ester 1-tert-butyl ester as colorless liquid. MS m/e (%): 376 (2), 340 (10), 284 (6), 240 (21), 91 (48), 68 (100), 57 (63); $[\alpha]_D$=+24.5° (c=1% in methanol).

b) (2R,4S)-4-Phenylselanyl-pyrrolidine-1,2-dicarboxylic Acid 1-tert-Butyl Ester 2-Ethyl Ester A solution of 7.99 g (0.026 mol) diphenyl diselenide in 250 ml ethanol was treated with 1.59 g (0.042 mol) sodium borohydride and stirring was continued until the yellow solution turned colorless. After addition of 20.0 g (0.042 mol) (2R,4R)-4-(toluene-4-sulfonyloxy)-pyrrolidine-1,2-dicarboxylic acid 2-benzyl ester 1-tert-butyl ester the mixture was refluxed for 2.5 hours. A white precipitate was filtered off and the solvent was removed in vacuo. Chromatography on silicagel with dichloromethane/methanol 98:2 gave 8.48 g (51%) (2R,4S)-4-Phenylselanyl-pyrrolidine-1,2-dicarboxylic acid 1-tert-butyl ester 2-ethyl ester as a colorless oil. MS m/e (%): 399 (7), 326 (13), 270 (18), 226 (38), 186 (35), 68 (60), 57 (100), 41 (28). $[\alpha]_D$=+40.4° (c=1% in methanol). Also isolated was 0.6 g (2R,4S)-4-phenylselanyl-pyrrolidine-1,2-dicarboxylic acid 2-benzyl ester 1-tert-butyl ester as colorless oil. MS m/e (%): 461 (7), 326 (21), 270 (37), 248 (48), 226 (49), 209 (30), 91 (100), 68 (54), 57 (96). $[\alpha]_D$=+33.2° (c=1% in methanol).

c) (R)-2,5-Dihydro-pyrrole-1,2-dicarboxylic Acid 1-tert-Butyl Ester 2-Ethyl Ester To a solution of 7.35 g (0.016 mol) (2R,4S)-4-phenylselanyl-pyrrolidine-1,2-dicarboxylic acid 1-tert-butyl ester 2-ethyl ester in 80 ml dichloromethane were added at 0–5° C. 1.93 ml (0.024 mol) pyridine and 4.6 ml 30% hydrogen peroxide and stirring was continued for 1.5 hours. The mixture was extracted with 5% aqueous HCl, saturated aqueous sodium carbonate, and water. Chromatography on silicagel with ethylacetate/hexane 1:5 yielded 2.99 g (77%) (R)-2,5-dihydro-pyrrole-1,2-dicarboxylic acid 1-tert-butyl ester 2-ethyl ester as colorless oil. MS m/e (%): 186 (11), 168 (48), 140 (32), 112 (100), 68 (85), 57 (58). $[\alpha]_D$=+242° (c=1% in chloroform).

d) (R)-2,5-Dihydro-1H-pyrrole-2-carboxylic Acid Ethyl Ester Trifluoroacetate (1:1) 1.5 g (0.006 mol) (R)-2,5-dihydro-pyrrole-1,2-dicarboxylic acid 1-tert-butyl ester 2-ethyl ester were dissolved at 5° C. in 10 ml trifluoroacetic acid and stirring was continued at room temperature for 3 hours. Evaporation of the solvent in vacuo gave 2.05 g (quant.) of (R)-2,5-dihydro-1H-pyrrole-2-carboxylic acid ethyl ester trifluoroacetate (1:1) as a yellow oil. MS m/e (%): 142 (1), 68 (100), 45 (10), 41 (15). $[\alpha]_D$=+95.4° (c=1% in methanol).

e) (R)-1-[6-[(R)-2-Ethyloxycarbonyl-2,5-dihydropyrrole-1-yl]-6-oxo-hexanoyl]-2,5-dihydropyrrole-2-carboxylic Acid Ethyl Ester To a suspension of 0.99 g (0.003 mol(R)-2,5-dihydro-1H-pyrrole-2-carboxylic acid ethyl ester trifluoroacetate (1:1) in 20 ml dichloromethane were added 1.3 ml (0.009 mol) triethylamine, and 0.22 ml (0.0015 mol) adipolydichloride in 5 ml dichloromethane. After stirring at room temperature over night the mixture was extracted with 1N HCl, water and aqueous sodiumbicarbonate and dried with sodiumsulfate. Chromatogaphy over silicagel with ethylacetate gave 0.37 g (32%) (R)-1-[6-[(R)-2-ethyloxycarbonyl-2,5-dihydropyrrole-1-yl]-6-oxo-hexanoyl]-2,5-dihydropyrrole-2-carboxylic acid ethyl ester as yellow oil. ISP-MS: 393 (MH)$^+$.

f) (R)-1-[6-[(R)-2-Carboxy-2,5-dihydropyrrole-1-yl]-6-oxo-hexanoyl]-2,5-dihydropyrrole-2-carboxylic Acid 0.09 g (0.0002 mol) (R)-1-[6-[(R)-2-ethyloxycarbonyl-2,5-dihydropyrrole-1-yl]-6-oxo-hexanoyl]-2,5-dihydropyrrole-2-carboxylic acid ethyl ester were stirred with aqueous HCl at 50° C. for 3 hours. The solvent was evaporated and the residue dissolved in water and lyophilized to yield 0.08 g (97%) (R)-1-[6-[(R)-2-carboxy-2,5-dihydropyrrole-1-yl]-6-oxo-hexanoyl]-2,5-dihydropyrrole-2-carboxylic acid as light yellow foam. ISP-MS: 335 (M–H)$^-$.

EXAMPLE 104

(R)-1-[[2-[2-[(R)-2-Carboxy-2,5-dihydropyrrole-1-yl]-2-oxo-ethoxyl]-phenoxy]acetyl]-2,5-dihydropyrrole-2-carboxylic Acid a) (R)-1-[[2-[2-[(R)-2-Ethylcarbonyl-2,5-dihydropyrrole-1-yl]-2-oxo-ethoxyl]-phenoxy]acetyl]-2,5-dihydropyrrole-2-carboxylic Acid Ethyl Ester To a mixture of 0.99 g (0.003 mol) (R)-2,5-dihydro-1H-pyrrole-2-carboxylic acid ethyl ester trifluoroacetate (1:1), 0.34 g (0.0015 mol) 1,2-phenylenedioxydiacetic acid, 1.3 ml (0.012 mol) N-methylmorpholine, and 0.46 g (0.003 mol) 1-hydroxybenzotriazole hydrate in 80 ml dichloromethane were added 0.57 g (0.003 mol) 1-(3-dimethylaminopropyl)-3-ethylcarbodiimid hydrochloride. After stirring at room temperature for 18 hours the mixture was extracted with 1N HCl, water, 10% aqueous sodium bicarbonate and again water. Chromatography over silicagel with ethylacetate yielded 0.45 g (32%) (R)-1-[[2-[2-[(R)-2-ethylcarbonyl-2,5-dihydropyrrole-1-yl]-2-oxo-ethoxyl]-phenoxy]acetyl]-2,5-dihydropyrrole-2-carboxylic acid ethyl ester as colorless oil. ISP-MS: 473 (MH)$^+$.

b) (R)-1-[[2-[2-[(R)-2-Carboxy-2,5-dihydropyrrole-1-yl]-2-oxo-ethoxyl]-phenoxy]acetyl]-2,5-dihydropyrrole-2-carboxylic Acid 0.17 g (0.0004 mol) (R)-1-[[2-[2-[(R)-2-ethylcarbonyl-2,5-dihydropyrrole-1-yl]-2-oxo-ethoxyl]-phenoxy]acetyl]-2,5-dihydropyrrole-2-carboxylic acid ethyl ester were stirred with aqueous HCl at 50° C. for 3 hours. The solvent was evaporated and the residue dissolved in water and lyophilized to yield 0.13 g (86%) (R)-1-[[2-[2-[(R)-2-carboxy-2,5-dihydropyrrole-1-yl]-2-oxo-ethoxyl]-phenoxy]acetyl]-2,5-dihydropyrrole-2-carboxylic acid as white amorphous powder. ISP-MS: 417 (MH)$^+$.

EXAMPLE A

Tablets of the following composition were manufactured in the usual manner:

|  | mg/tablet |
| --- | --- |
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are manufactured in the usual manner:

|  | mg/tablet |
| --- | --- |
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are manufactured:

|  | mg/capsule |
| --- | --- |
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

The subject invention has been described in terms of its preferred embodiments. Upon reading the present specification certain alternative embodiments will become obvious to those skilled in the art. These variations are to be considered within the scope and spirit of the subject invention which is only to be limited by the claims that follow and their equivalents.

What is claimed is:

1. A D-proline compound of the formula:

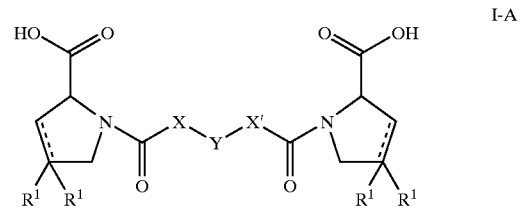

I-A wherein

R$^1$ is hydrogen or halogen;

X is —(CH$_2$)$_n$—; —CH(R$^2$)(CH$_2$)$_n$—; —CH$_2$O(CH$_2$)$_n$—; —CH$_2$NH—; benzyl; —C(R$^2$)=CH—; —CH$_2$CH(OH)—; or thiazol-2,5-diyl;

Y is 2,5-furanyl or 2,5-thienyl;

X' is —(CH$_2$)$_n$—; —(CH$_2$)$_n$CH(R$^2$)—; —(CH$_2$)$_n$OCH$_2$—; —NHCH$_2$—; benzyl; —CH=C(R$^2$)—; —CH(OH)CH$_2$—; or thiazol-2,5-diyl;

R$^2$ is lower alkyl, lower alkoxy, or benzyl;

=== is a single or a double bond; and n is 0–3, or a pharmaceutically acceptable salt, monoester, or diester thereof.

2. The compound according to claim 1, wherein the compound is of the formula:

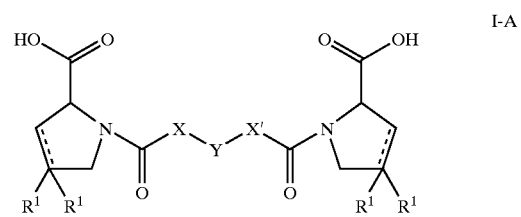

I-A wherein $R^1$ is hydrogen or halogen;

X is —(CH$_2$)$_n$—; —CH(R$^2$)(CH$_2$)$_n$—; —CH$_2$O(CH$_2$)$_n$—; —CH$_2$NH—; benzyl; —C(R$^2$)=CH—; —CH$_2$CH(OH)—; or thiazol-2,5-diyl;

Y is 2,5-furanyl or 2,5-thienyl;

X' is —(CH$_2$)$_n$—; —(CH$_2$)$_n$CH(R$^2$)—; —(CH$_2$)$_n$OCH$_2$—; —NHCH$_2$—; benzyl; —CH=C(R$^2$)—; —CH(OH)CH$_2$—; or thiazol-2,5-diyl;

$R^2$ is lower alkyl, lower alkoxy, or benzyl;

=== is a single or a double bond; and n is 0–3, or a pharmaceutically acceptable salt, monoester, or diester thereof.

3. The compound according to claim 2, wherein X is —CH(R$^2$)(CH$_2$)$_n$—, $R^2$ is methyl or methoxy, and n is 0 or 1.

4. The compound of claim 2, wherein X is —CH$_2$NH—.

5. A process for preparing a compound of the formula:

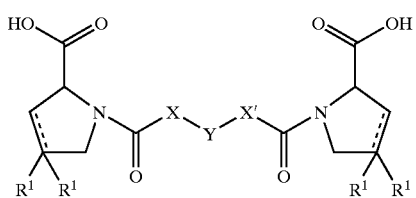

I-A wherein $R^1$ is hydrogen or halogen;

X is —(CH$_2$)$_n$—; —CH(R$^2$)(CH$_2$)n—; —CH$_2$O(CH$_2$)$_n$—; —CH$_2$NH—; benzyl; —C(R$^2$)=CH—; —CH$_2$CH(OH)—; or thiazol-2,5-diyl;

Y is 2,5-furanyl or 2,5-thienyl;

X' is —(CH$_2$)$_n$—; —(CH$_2$)$_n$CH(R$^2$)—; —(CH$_2$)$_n$OCH$_2$—; —NHCH$_2$—; benzyl; —CH=C(R$^2$)—; —CH(OH)CH$_2$—; or thiazol-2,5-diyl;

$R^2$ is lower alkyl, lower alkoxy, or benzyl;

=== is a single or a double bond; and n is 0–3;

which process comprises cleaving off the protecting group from a compound of formula:

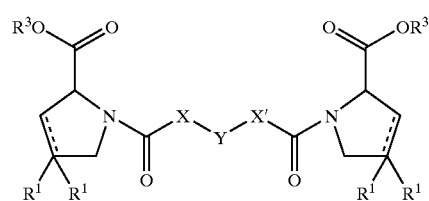

III wherein $R^1$, X, Y and X' are as above, and $R^3$ is a protecting group.

6. A method of treating diseases having amyloidosis, which comprises administering to a subject in need of such treatment an effective amount of a compound of the formula:

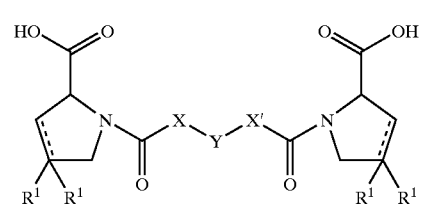

I-A wherein $R^1$ is hydrogen or halogen;

X is —(CH$_2$)$_n$—; —CH(R$^2$)(CH$_2$)n—; —CH$_2$O(CH$_2$)$_n$—; —CH$_2$NH—; benzyl; —C(R$^2$)=CH—; —CH$_2$CH(OH)—; or thiazol-2,5-diyl;

Y is 2,5-furanyl or 2,5-thienyl;

X' is —(CH$_2$)$_n$—; —(CH$_2$)$_n$CH(R$^2$)—; —(CH$_2$)$_n$OCH$_2$—; —NHCH$_2$—; benzyl; —CH=C(R$^2$)—; —CH(OH)CH$_2$—; or thiazol-2,5-diyl;

$R^2$ is lower alkyl, lower alkoxy, or benzyl;

=== is a single or a double bond; and n is 0–3, or a pharmaceutically acceptable salt, monoester, or diester thereof.

7. The method according to claim 6, wherein the disease is Alzheimer's disease, maturity onset diabetes mellitus, familial amyloid polyneuropathy, scrapie, or Kreuzfeld-Jacob disease.

8. The method according to claim 7, wherein the disease is Alzheimer's disease.

9. The compound according to claim 1 which is (R)-1-[5-[(R)-2-carboxy-pyrrolidine-1-carbonyl]-thiophene-2-carbonyl]-pyrrolidine-2-carboxylic acid.

10. The compound according to claim 1 which is (R)-1-[5-[(R)-2-carboxy-pyrrolidine-1-carbonyl]-furan-2-carbonyl]-pyrrolidine-2-carboxylic acid.

11. The compound according to claim 1 which is (R)-1-[[5-[2-[(R)-2-carboxy-pyrrolidin-1-yl]-2-oxo-ethyl]-thiophen-2-yl]-acetyl]-pyrrolidine-2-carboxylic acid.

* * * * *